US007126039B2

(12) United States Patent
Denning et al.

(10) Patent No.: US 7,126,039 B2
(45) Date of Patent: Oct. 24, 2006

(54) ANIMAL TISSUE WITH CARBOHYDRATE ANTIGENS COMPATIBLE FOR HUMAN TRANSPLANTATION

(75) Inventors: Chris Denning, Loughborough (GB); A. John Clark, Midlothian (GB); J. Michael Schiff, Menlo Park, CA (US)

(73) Assignee: Geron Corporation, Menlo Park, CA (US)

( * ) Notice: Subject to any disclaimer, the term of this patent is extended or adjusted under 35 U.S.C. 154(b) by 412 days.

(21) Appl. No.: 10/105,963

(22) Filed: Mar. 21, 2002

(65) Prior Publication Data

US 2003/0068818 A1  Apr. 10, 2003

Related U.S. Application Data

(60) Provisional application No. 60/277,811, filed on Mar. 21, 2001.

(51) Int. Cl.
*A01K 67/027* (2006.01)
*C12N 15/00* (2006.01)
*C12N 5/00* (2006.01)

(52) U.S. Cl. .......................... 800/17; 800/24; 435/325

(58) Field of Classification Search ................ 800/24, 800/25, 14–18; 435/1.1, 325, 354, 352
See application file for complete search history.

(56) References Cited

U.S. PATENT DOCUMENTS

| | | | | |
|---|---|---|---|---|
| 4,959,317 | A | 9/1990 | Sauer | 435/172.3 |
| 5,068,191 | A | 11/1991 | Clausen et al. | 435/193 |
| 5,326,857 | A | 7/1994 | Yamamoto et al. | 536/23.2 |
| 5,614,396 | A | 3/1997 | Bradley et al. | 435/172.3 |
| 5,821,117 | A | 10/1998 | Sandrin et al. | 435/320.1 |
| 5,849,991 | A | 12/1998 | d'Apice et al. | 800/2 |
| 5,929,301 | A | 7/1999 | Baszcynski et al. | 800/278 |
| 6,147,276 | A | 11/2000 | Campbell et al. | 800/24 |
| 6,200,806 | B1 | 3/2001 | Thomson | 435/366 |
| 6,252,133 | B1 | 6/2001 | Campbell et al. | 800/24 |
| 6,261,836 | B1 | 7/2001 | Cech et al. | 435/325 |

FOREIGN PATENT DOCUMENTS

| | | |
|---|---|---|
| WO | WO 95/28412 | 10/1995 |
| WO | WO 95/33828 | 12/1995 |
| WO | WO 95/34202 | 12/1995 |
| WO | WO 96/28967 | 9/1996 |
| WO | WO 97/12035 | 4/1997 |
| WO | WO 99/20741 | 4/1999 |
| WO | WO 99/21415 | 5/1999 |
| WO | WO 01/42421 | 6/2001 |
| WO | WO 01/51616 | 7/2001 |

OTHER PUBLICATIONS

Clark, A. J. et al. Gene Targeting in Livestock: A Preview. Transgenic Research. 2000, vol. 9, pp. 263-275.*
Denning, C. et al. Gene Targeting in Primary Fetal Fibroblasts from Sheep and Pig. Cloning and Stem Cells. 2001, vol. 3, O. 4, pp. 221-231.*
Meirelles et al. Complete Replacement of the Mitochondrial Genotype in a Bos indicus Calf Reconstructed by Nuclear Transfer to a Bos taurus Oocyte. Genetics 2001, vol. 158, pp. 351-356.*
Fehilly et al. Cytogenetic and Blood Group Studies of Sheep/Goat Chimaeras. J. Reproduct. Fertility. 1985, vol. 74, pp. 215-221.*
Wheeler, M. B. et al. Transgenic Technology and Applications in Swine. Theriogenelogy. 2001, vol. 56, pp. 1345-1369.*
Prelle, K. et al. Establishment of Pluripotent Cell Lines from Vertebrate Species—Present Status and Future Prospects. Cells Tissues Organs. 1999, vol. 165, pp. 220-236.*
Moreadith, R. W. Gene Targeting in Embryonic Stem Cells: the New Physiology and Metabolism. J. Molecular Med. 1997, vol. 75, pp. 208-216.*
Gardner, R. L. et al. Reflections on the Biology of Embryonic Stem Cells. Internat. J. Devel. 1997, vol. 41, pp. 235-243.*
(Cameron, E.R. Recent Advances in Transgenic Technology, Molec. Biotech. 1997, vol. 7, pp. 253-265.*
Sigmund, C.D. Viewpoint: Are Studies in Genetically Altered Mice Out of Control. Arteroscler. Throm. Vasc. Biol. 2000, vol. 20, pp. 1425-1429.*
Niemann, H. Transgenic Farm Animals Get Off the Ground. Transg. Res. 1998, vol. 7, pp. 73-75.*
Gugenheim, J. et al. Liver Transplantation Across ABO Blood Group Barriers. The Lancet. Sep. 1, 1990, vol. 336, pp. 519-523.*
Chen, C-G. et al. Transgenic Expression of Human Alpha 1,2-Fucosyltransferase Prolongs Mouse Heart Survival in an Ex Vivo Model of Xenograft Rejection. Transplantation. Mar. 6, 1997, vol. 65, pp. 832-837.*
Shinkel, T. A. et al. Changes in Cell Surface Glycosylation in Alpha 1,3-Galactosyltransferase Knockout and Alpha 1,2-Fucosyltransferase Transgenic Mice. Transplantation. Jul. 27, 1998, vol. 64, pp. 197-204.*
Sharma et al. Pig Cells that Lack the Gene for Alpha1,3-Galactosyltransferase Express Low Levels of the Gal Antigen. Transplantation. Feb. 27, 2003, vol. 75, No. 4, pp. 430-436.*
Schroeder et al. Hyperacute Rejection is Attenuated in GalT Knockout Swine Lungs Perfused Ex Vivo with Human Blood. Transplantation Proceedings. 2005, vol. 37, pp. 512-513.*

(Continued)

*Primary Examiner*—Deborah Crouch
(74) *Attorney, Agent, or Firm*—Finnegan, Henderson, Farabow, Garrett & Dunner, LLP

(57) ABSTRACT

This disclosure provides a system for generating animal tissue with carbohydrate antigens that are compatible for transplantation into human patients. The tissue is inactivated homozygously for expression of $\alpha(1,3)$galactosyltransferase, and comprises a transgene for $\alpha(1,2)$fucosyltransferase. As a result, cell-surface N-acetyl lactosamine is not converted to the Gal$\alpha(1,3)$Gal xenoantigen. Instead, it is converted to Fuc$\alpha(1,2)$Gal, which is H substance, a self-antigen in humans. The tissue may also contain A or B-transferase, which will cause H substance to be converted into other ABO blood group antigens for compatibility with patients of the same blood type. This invention improves transplant compatibility of the xenograft tissue by lessening the risk of reactions resulting from xenoantigen and unconverted N-acetyl lactosamine acceptor determinants.

15 Claims, 7 Drawing Sheets

OTHER PUBLICATIONS

Tseng et al. Bone Marrow Transplantation from Alpha-1,3-Galactosyltransferase Gene-Knockout Pigs in Baboons. Xenotransplantation, 2004, vol. 11, pp. 361-370.*

Bodnar, et al., Extension of life-span by introduction of telomerase into normal human cells, Science 279:349 (1998).

Chen, et al., Transgenic expression of human alpha 1,2-fucosyltransferase (H-transferase) prolongs mouse heart survival in an ex vivo model of xenograft rejection, Transplantation 65:832 (1998).

Costa, et al., Comparative analysis of three genetic modifications designed to inhibit human serum-mediated cytolysisexion, Xenotransplantion 6:6 (1999).

Cowley, A Pig May Someday Save Your Life, Newsweek, Jan. 1 (2000).

Denning, et al., Deletion of the a(1,3)galactosylt transferase (GGTA1) gene and the prion protein (PrP) gene in sheep, Nature Biol. 19:559 (2001).

Galili, et al, Gene sequences suggest inactivation of a-1,3-galactosyltransferase in catarrhines after the divergence of apes from monkeys, Proc. Natl. Acad. Sci. USA 88:7401 (1991).

Gustafsson, Alpha 1,3galactosyltransferase: a target for in vivo genetic manipulation in xenotransplantation, et al., Immunol. Rev. 141:59 (1994).

Gabius, Animal lectins, Eur. J. Biochem 243:543 (1997).

Hayashi, et al., Adenovirus-mediated gene transfer of antisense ribozyme for alpha (1,3)galactosyltransferase gene and alpha (1,2)fucosyltansferase gene in xenotransplantation, Transplant Proc. 29:2213 (1997).

Hayes, et al., An alpha-D-galactosyl-binding lectin from *Bandeiraea siplicifolia* seeds. Isolation by affinity chromatography and characterization., J Biol. Chem. 294:1904 (1974).

Henion, et al., Defining the minimal size of catalytically active primate a1,3 galactosyltransferase, Glycobiology 4:193 (1994).

Jiang et al., Telomerase expression in human somatic cells does not induce changes associated with a transformed phenotype, Nat. Genet. 21:111 (1999).

Joziasse, et al., Mammalian glycosyltransferases: genomic organization and protein structure, Glycobiology 2:271 (1992) Review.

Joziasse, et al., Xenotransplantation: the importance of the Galalpha1,3Gal epitope in hyperacute vascular rejection, Biochim. Biophys. Acta 1455:403 (1999).

Joziasse, et al., Bovine alpha 1—3 galactosyltransferase: isolation and characterization of a cDNA clone. Identification of homologous sequences in human genomic DNA, J. Biol. Chem. 264:14290 (1989).

Joziasse, et al., Characterization of an a1-3-galactosyltransferase homologue on human chromosome 12 that is organized as a processed pseudogene, J. Biol. Chem. 266:6991 (1991).

Joziasse, et al., Murine alpha 1,3-galactosyltransferase, A single gene locus specifies four isoforms of the enzyme by alternative splicing, J. Biol. Chem. 267: 5534 (1992).

Katayama, et al., Direct gene replacement of the mouse a(1,3)-galactosyltransferase gene with human a(1,2)-fucosyltransferase gene, Xenotransplantation 4:147 (1997).

Katayama, et al., Porcine alpha-1,3-galactosyltransferase: full length cDNA cloning, genomic organization, and analysis of splicing variants, Glycoconjugate J. 15:583 (1998).

Larsen, et al., Isolation of a cDNA encoding a murine UDPgalactose:beta-D-galactosyl- 1,4-N-acetyl-D-glucosaminide alpha-1,3-galactosyltransferase: expression cloning by gene transfer, Proc. Natl. Acad. Sci. USA 86:8227 (1989).

Larsen, et al., Frameshift and nonsense mutations in a human genomic sequence homologous to a murine UDP-Gal:beta-D-Gal(1,4)-D-GlcNAc alpha(1,3)-galactosyltransferase cDNA, J. Biol. Chem. 265:7055 (1990).

Lavitrano, et al., Xenotransplantation: state of the art, Forum Genova 9:74 (1999).

Matsumoto, et al., Purification and characterization of an anti-H(O) phytohemagglutinin of Ulex europeus, Biochim. Biophys. Acta 194:180 (1969).

McKenzie, et al., Distribution of the major xenoantigen (gal (alpha 1-3)gal) for pig to human xenografts, Transpl. Immunol. 2:81 (1994).

Osman, et al., Switching amino-terminal cytoplasmic domains of a(1,2)fucosyltransferase and a(1,3)galactosyltransferase alters the expression of H substance and Gala(1,3)Gal*, Proc. Natl. Acad. Sci. USA 23:4677 (1997).

Perillo, et al., Galectins: versatile modulators of cell adhesion, cell proliferation, and cell death, J. Mol Med. 76:402 (1998).

Rabinovitch, Galectins: an evolutionarily conserved family of animal lectins with multifunctional properties; a trip from the gene to clinical therapy, Cell Death Differ. 6:711 (1999).

Romans, et al., Monogamous bivalency of 1gG antibodies, J. Immun. 124:2807 (1980).

Sandrin, et al., Transgenic approaches for the reduction in Expressionof Gala(1,3)Gal for xenotransplantation, Frontiers Biosci. 2:e1-11 (1997).

Shinkel, et al., Changes in cell surface glycosylation ion a1,3-galactosyltransferase knockout and a 1,2-fucosyltransferase transgenic mice, Transplantation, 64:197 (1997).

Strahan, et al., cDNA sequence and chromosome localization of pig alpha 1,3 galactosyltransferase, Immunogenetics 41:101 (1995).

Chen, et al., Reduction in Gal- α1,3-Gal epitope expression in transgenic mice expressing human H-transferase Xenotransplantation 3:69 (1996).

Ramscondar JJ, Machaly Z, Costa C, Williams BL, Fodor WL. Bondloll KR. Production of alpha 1,3-galactosyltransferase-knockout cloned pigs expressing human alpha 1,2-fucosylosyltransferase. Biol Reprod. Aug. 2003;69(2):437-45.

* cited by examiner

DAPI UEA-rhodamine 293 human cells

B9 telomerized sheep cells expressing α1,2FT

C9 telomerized sheep cells expressing α1,2FT

SEQUENCE LISTING

<160> NUMBER OF SEQ ID NOS: 40

<210> SEQ ID NO 1
<211> LENGTH: 4015
<212> TYPE: DNA
<213> ORGANISM: Homo sapiens
<220> FEATURE:
<221> NAME/KEY: CDS
<222> LOCATION: (56)..(3454)
<223> OTHER INFORMATION:

<400> SEQUENCE: 1

```
gcagcgctgc gtcctgctgc gcacgtggga agccctggcc ccggccaccc ccgcg atg        58
                                                             Met
                                                             1 ccg cgc gct ccc cgc tgc cga gcc gtg cgc tcc ctg ctg cgc agc cac        106
Pro Arg Ala Pro Arg Cys Arg Ala Val Arg Ser Leu Leu Arg Ser His
        5                  10                  15 tac cgc gag gtg ctg ccg ctg gcc acg ttc gtg cgg cgc ctg ggg ccc        154
Tyr Arg Glu Val Leu Pro Leu Ala Thr Phe Val Arg Arg Leu Gly Pro
     20                  25                  30 cag ggc tgg cgg ctg gtg cag cgc ggg gac ccg gcg gct ttc cgc gcg        202
Gln Gly Trp Arg Leu Val Gln Arg Gly Asp Pro Ala Ala Phe Arg Ala
 35                  40                  45 ctg gtg gcc cag tgc ctg gtg tgc gtg ccc tgg gac gca cgg ccg ccc        250
Leu Val Ala Gln Cys Leu Val Cys Val Pro Trp Asp Ala Arg Pro Pro
50                  55                  60                  65 ccc gcc gcc ccc tcc ttc cgc cag gtg tcc tgc ctg aag gag ctg gtg        298
Pro Ala Ala Pro Ser Phe Arg Gln Val Ser Cys Leu Lys Glu Leu Val
                 70                  75                  80 gcc cga gtg ctg cag agg ctg tgc gag cgc ggc gcg aag aac gtg ctg        346
Ala Arg Val Leu Gln Arg Leu Cys Glu Arg Gly Ala Lys Asn Val Leu
             85                  90                  95 gcc ttc ggc ttc gcg ctg ctg gac ggg gcc cgc ggg ggc ccc ccc gag        394
Ala Phe Gly Phe Ala Leu Leu Asp Gly Ala Arg Gly Gly Pro Pro Glu
        100                 105                 110 gcc ttc acc acc agc gtg cgc agc tac ctg ccc aac acg gtg acc gac        442
Ala Phe Thr Thr Ser Val Arg Ser Tyr Leu Pro Asn Thr Val Thr Asp
    115                 120                 125 gca ctg cgg ggg agc ggg gcg tgg ggg ctg ctg ctg cgc cgc gtg ggc        490
Ala Leu Arg Gly Ser Gly Ala Trp Gly Leu Leu Leu Arg Arg Val Gly
130                 135                 140                 145 gac gac gtg ctg gtt cac ctg ctg gca cgc tgc gcg ctc ttt gtg ctg        538
Asp Asp Val Leu Val His Leu Leu Ala Arg Cys Ala Leu Phe Val Leu
                150                 155                 160 gtg gct ccc agc tgc gcc tac cag gtg tgc ggg ccg ccg ctg tac cag        586
Val Ala Pro Ser Cys Ala Tyr Gln Val Cys Gly Pro Pro Leu Tyr Gln
            165                 170                 175 ctc ggc gct gcc act cag gcc cgg ccc ccg cca cac gct agt gga ccc        634
Leu Gly Ala Ala Thr Gln Ala Arg Pro Pro Pro His Ala Ser Gly Pro
        180                 185                 190 cga agg cgt ctg gga tgc gaa cgg gcc tgg aac cat agc gtc agg gag        682
```

|   |   |
|---|---|
| Arg Arg Arg Leu Gly Cys Glu Arg Ala Trp Asn His Ser Val Arg Glu<br>195                        200                        205 |   |
| gcc ggg gtc ccc ctg ggc ctg cca gcc ccg ggt gcg agg agg cgc ggg<br>Ala Gly Val Pro Leu Gly Leu Pro Ala Pro Gly Ala Arg Arg Arg Gly<br>210                      215                   220                 225 | 730 |
| ggc agt gcc agc cga agt ctg ccg ttg ccc aag agg ccc agg cgt ggc<br>Gly Ser Ala Ser Arg Ser Leu Pro Leu Pro Lys Arg Pro Arg Arg Gly<br>                      230                   235                 240 | 778 |
| gct gcc cct gag ccg gag cgg acg ccc gtt ggg cag ggg tcc tgg gcc<br>Ala Ala Pro Glu Pro Glu Arg Thr Pro Val Gly Gln Gly Ser Trp Ala<br>               245                   250                   255 | 826 |
| cac ccg ggc agg acg cgt gga ccg agt gac cgt ggt ttc tgt gtg gtg<br>His Pro Gly Arg Thr Arg Gly Pro Ser Asp Arg Gly Phe Cys Val Val<br>          260                   265                   270 | 874 |
| tca cct gcc aga ccc gcc gaa gaa gcc acc tct ttg gag ggt gcg ctc<br>Ser Pro Ala Arg Pro Ala Glu Glu Ala Thr Ser Leu Glu Gly Ala Leu<br>275                       280                   285 | 922 |
| tct ggc acg cgc cac tcc cac cca tcc gtg ggc cgc cag cac cac gcg<br>Ser Gly Thr Arg His Ser His Pro Ser Val Gly Arg Gln His His Ala<br>290                      295                    300               305 | 970 |
| ggc ccc cca tcc aca tcg cgg cca cca cgt ccc tgg gac acg cct tgt<br>Gly Pro Pro Ser Thr Ser Arg Pro Pro Arg Pro Trp Asp Thr Pro Cys<br>               310                   315                   320 | 1018 |
| ccc ccg gtg tac gcc gag acc aag cac ttc ctc tac tcc tca ggc gac<br>Pro Pro Val Tyr Ala Glu Thr Lys His Phe Leu Tyr Ser Ser Gly Asp<br>          325                   330                   335 | 1066 |
| aag gag cag ctg cgg ccc tcc ttc cta ctc agc tct ctg agg ccc agc<br>Lys Glu Gln Leu Arg Pro Ser Phe Leu Leu Ser Ser Leu Arg Pro Ser<br>340                       345                   350 | 1114 |
| ctg act ggc gct cgg agg ctc gtg gag acc atc ttt ctg ggt tcc agg<br>Leu Thr Gly Ala Arg Arg Leu Val Glu Thr Ile Phe Leu Gly Ser Arg<br>355                        360                   365 | 1162 |
| ccc tgg atg cca ggg act ccc cgc agg ttg ccc cgc ctg ccc cag cgc<br>Pro Trp Met Pro Gly Thr Pro Arg Arg Leu Pro Arg Leu Pro Gln Arg<br>370                      375                   380               385 | 1210 |
| tac tgg caa atg cgg ccc ctg ttt ctg gag ctg ctt ggg aac cac gcg<br>Tyr Trp Gln Met Arg Pro Leu Phe Leu Glu Leu Leu Gly Asn His Ala<br>                      390                   395                 400 | 1258 |
| cag tgc ccc tac ggg gtg ctc ctc aag acg cac tgc ccg ctg cga gct<br>Gln Cys Pro Tyr Gly Val Leu Leu Lys Thr His Cys Pro Leu Arg Ala<br>          405                   410                   415 | 1306 |
| gcg gtc acc cca gca gcc ggt gtc tgt gcc cgg gag aag ccc cag ggc<br>Ala Val Thr Pro Ala Ala Gly Val Cys Ala Arg Glu Lys Pro Gln Gly<br>420                       425                   430 | 1354 |
| tct gtg gcg gcc ccc gag gag gag gac aca gac ccc gtt cgc ctg gtg<br>Ser Val Ala Ala Pro Glu Glu Glu Asp Thr Asp Pro Arg Arg Leu Val<br>435                       440                   445 | 1402 |
| cag ctg ctc cgc cag cac agc agc ccc tgg cag gtg tac ggc ttc gtg<br>Gln Leu Leu Arg Gln His Ser Ser Pro Trp Gln Val Tyr Gly Phe Val<br>450                      455                   460               465 | 1450 |
| cgg gcc tgc ctg cgc cgg ctg gtg ccc cca ggc ctc tgg ggc tcc agg<br>Arg Ala Cys Leu Arg Arg Leu Val Pro Pro Gly Leu Trp Gly Ser Arg<br>                      470                   475                 480 | 1498 |
| cac aac gaa cgc cgc ttc ctc agg aac acc aag aag ttc atc tcc ctg<br>His Asn Glu Arg Arg Phe Leu Arg Asn Thr Lys Lys Phe Ile Ser Leu<br>               485                   490                   495 | 1546 |
| ggg aag cat gcc aag ctc tcg ctg cag gag ctg acg tgg aag atg agc<br>Gly Lys His Ala Lys Leu Ser Leu Gln Glu Leu Thr Trp Lys Met Ser<br>          500                   505                   510 | 1594 |

```
                                             -continued
gtg cgg gac tgc gct tgg ctg cgc agg agc cca ggg gtt ggc tgt gtt      1642
Val Arg Asp Cys Ala Trp Leu Arg Arg Ser Pro Gly Val Gly Cys Val
515                 520                 525 ccg gcc gca gag cac cgt ctg cgt gag gag atc ctg gcc aag ttc ctg      1690
Pro Ala Ala Glu His Arg Leu Arg Glu Glu Ile Leu Ala Lys Phe Leu
530                 535                 540                 545 cac tgg ctg atg agt gtg tac gtc gtc gag ctg ctc agg tct ttc ttt      1738
His Trp Leu Met Ser Val Tyr Val Val Glu Leu Leu Arg Ser Phe Phe
                550                 555                 560 tat gtc acg gag acc acg ttt caa aag aac agg ctc ttt ttc tac cgg      1786
Tyr Val Thr Glu Thr Thr Phe Gln Lys Asn Arg Leu Phe Phe Tyr Arg
            565                 570                 575 aag agt gtc tgg agc aag ttg caa agc att gga atc aga cag cac ttg      1834
Lys Ser Val Trp Ser Lys Leu Gln Ser Ile Gly Ile Arg Gln His Leu
        580                 585                 590 aag agg gtg cag ctg cgg gag ctg tcg gaa gca gag gtc agg cag cat      1882
Lys Arg Val Gln Leu Arg Glu Leu Ser Glu Ala Glu Val Arg Gln His
595                 600                 605 cgg gaa gcc agg ccc gcc ctg ctg acg tcc aga ctc cgc ttc atc ccc      1930
Arg Glu Ala Arg Pro Ala Leu Leu Thr Ser Arg Leu Arg Phe Ile Pro
610                 615                 620                 625 aag cct gac ggg ctg cgg ccg att gtg aac atg gac tac gtc gtg gga      1978
Lys Pro Asp Gly Leu Arg Pro Ile Val Asn Met Asp Tyr Val Val Gly
                630                 635                 640 gcc aga acg ttc cgc aga gaa aag agg gcc gag cgt ctc acc tcg agg      2026
Ala Arg Thr Phe Arg Arg Glu Lys Arg Ala Glu Arg Leu Thr Ser Arg
            645                 650                 655 gtg aag gca ctg ttc agc gtg ctc aac tac gag cgg gcg cgg cgc ccc      2074
Val Lys Ala Leu Phe Ser Val Leu Asn Tyr Glu Arg Ala Arg Arg Pro
        660                 665                 670 ggc ctc ctg ggc gcc tct gtg ctg ggc ctg gac gat atc cac agg gcc      2122
Gly Leu Leu Gly Ala Ser Val Leu Gly Leu Asp Asp Ile His Arg Ala
675                 680                 685 tgg cgc acc ttc gtg ctg cgt gtg cgg gcc cag gac ccg ccg cct gag      2170
Trp Arg Thr Phe Val Leu Arg Val Arg Ala Gln Asp Pro Pro Pro Glu
690                 695                 700                 705 ctg tac ttt gtc aag gtg gat gtg acg ggc gcg tac gac acc atc ccc      2218
Leu Tyr Phe Val Lys Val Asp Val Thr Gly Ala Tyr Asp Thr Ile Pro
                710                 715                 720 cag gac agg ctc acg gag gtc atc gcc agc atc atc aaa ccc cag aac      2266
Gln Asp Arg Leu Thr Glu Val Ile Ala Ser Ile Ile Lys Pro Gln Asn
            725                 730                 735 acg tac tgc gtg cgt cgg tat gcc gtg gtc cag aag gcc gcc cat ggg      2314
Thr Tyr Cys Val Arg Arg Tyr Ala Val Val Gln Lys Ala Ala His Gly
        740                 745                 750 cac gtc cgc aag gcc ttc aag agc cac gtc tct acc ttg aca gac ctc      2362
His Val Arg Lys Ala Phe Lys Ser His Val Ser Thr Leu Thr Asp Leu
755                 760                 765 cag ccg tac atg cga cag ttc gtg gct cac ctg cag gag acc agc ccg      2410
Gln Pro Tyr Met Arg Gln Phe Val Ala His Leu Gln Glu Thr Ser Pro
770                 775                 780                 785 ctg agg gat gcc gtc gtc atc gag cag agc tcc tcc ctg aat gag gcc      2458
Leu Arg Asp Ala Val Val Ile Glu Gln Ser Ser Ser Leu Asn Glu Ala
                790                 795                 800 agc agt ggc ctc ttc gac gtc ttc cta cgc ttc atg tgc cac cac gcc      2506
Ser Ser Gly Leu Phe Asp Val Phe Leu Arg Phe Met Cys His His Ala
            805                 810                 815 gtg cgc atc agg ggc aag tcc tac gtc cag tgc cag ggg atc ccg cag      2554
Val Arg Ile Arg Gly Lys Ser Tyr Val Gln Cys Gln Gly Ile Pro Gln
        820                 825                 830
```

-continued

| | |
|---|---|
| ggc tcc atc ctc tcc acg ctg ctc tgc agc ctg tgc tac ggc gac atg<br>Gly Ser Ile Leu Ser Thr Leu Leu Cys Ser Leu Cys Tyr Gly Asp Met<br>835                      840                    845 | 2602 |
| gag aac aag ctg ttt gcg ggg att cgg cgg gac ggg ctg ctc ctg cgt<br>Glu Asn Lys Leu Phe Ala Gly Ile Arg Arg Asp Gly Leu Leu Leu Arg<br>850                      855                    860                    865 | 2650 |
| ttg gtg gat gat ttc ttg ttg gtg aca cct cac ctc acc cac gcg aaa<br>Leu Val Asp Asp Phe Leu Leu Val Thr Pro His Leu Thr His Ala Lys<br>                    870                    875                    880 | 2698 |
| acc ttc ctc agg acc ctg gtc cga ggt gtc cct gag tat ggc tgc gtg<br>Thr Phe Leu Arg Thr Leu Val Arg Gly Val Pro Glu Tyr Gly Cys Val<br>885                      890                    895 | 2746 |
| gtg aac ttg cgg aag aca gtg gtg aac ttc cct gta gaa gac gag gcc<br>Val Asn Leu Arg Lys Thr Val Val Asn Phe Pro Val Glu Asp Glu Ala<br>        900                    905                    910 | 2794 |
| ctg ggt ggc acg gct ttt gtt cag atg ccg gcc cac ggc cta ttc ccc<br>Leu Gly Gly Thr Ala Phe Val Gln Met Pro Ala His Gly Leu Phe Pro<br>915                      920                    925 | 2842 |
| tgg tgc ggc ctg ctg ctg gat acc cgg acc ctg gag gtg cag agc gac<br>Trp Cys Gly Leu Leu Leu Asp Thr Arg Thr Leu Glu Val Gln Ser Asp<br>930                      935                    940                    945 | 2890 |
| tac tcc agc tat gcc cgg acc tcc atc aga gcc agt ctc acc ttc aac<br>Tyr Ser Ser Tyr Ala Arg Thr Ser Ile Arg Ala Ser Leu Thr Phe Asn<br>                    950                    955                    960 | 2938 |
| cgc ggc ttc aag gct ggg agg aac atg cgt cgc aaa ctc ttt ggg gtc<br>Arg Gly Phe Lys Ala Gly Arg Asn Met Arg Arg Lys Leu Phe Gly Val<br>                    965                    970                    975 | 2986 |
| ttg cgg ctg aag tgt cac agc ctg ttt ctg gat ttg cag gtg aac agc<br>Leu Arg Leu Lys Cys His Ser Leu Phe Leu Asp Leu Gln Val Asn Ser<br>        980                    985                    990 | 3034 |
| ctc cag acg gtg tgc acc aac atc tac aag atc ctc ctg ctg cag gcg<br>Leu Gln Thr Val Cys Thr Asn Ile Tyr Lys Ile Leu Leu Leu Gln Ala<br>995                      1000                  1005 | 3082 |
| tac agg ttt cac gca tgt gtg ctg cag ctc cca ttt cat cag caa<br>Tyr Arg Phe His Ala Cys Val Leu Gln Leu Pro Phe His Gln Gln<br>1010                      1015                  1020 | 3127 |
| gtt tgg aag aac ccc aca ttt ttc ctg cgc gtc atc tct gac acg<br>Val Trp Lys Asn Pro Thr Phe Phe Leu Arg Val Ile Ser Asp Thr<br>1025                      1030                  1035 | 3172 |
| gcc tcc ctc tgc tac tcc atc ctg aaa gcc aag aac gca ggg atg<br>Ala Ser Leu Cys Tyr Ser Ile Leu Lys Ala Lys Asn Ala Gly Met<br>1040                      1045                  1050 | 3217 |
| tcg ctg ggg gcc aag ggc gcc gcc ggc cct ctg ccc tcc gag gcc<br>Ser Leu Gly Ala Lys Gly Ala Ala Gly Pro Leu Pro Ser Glu Ala<br>1055                      1060                  1065 | 3262 |
| gtg cag tgg ctg tgc cac caa gca ttc ctg ctc aag ctg act cga<br>Val Gln Trp Leu Cys His Gln Ala Phe Leu Leu Lys Leu Thr Arg<br>1070                      1075                  1080 | 3307 |
| cac cgt gtc acc tac gtg cca ctc ctg ggg tca ctc agg aca gcc<br>His Arg Val Thr Tyr Val Pro Leu Leu Gly Ser Leu Arg Thr Ala<br>1085                      1090                  1095 | 3352 |
| cag acg cag ctg agt cgg aag ctc ccg ggg acg acg ctg act gcc<br>Gln Thr Gln Leu Ser Arg Lys Leu Pro Gly Thr Thr Leu Thr Ala<br>1100                      1105                  1110 | 3397 |
| ctg gag gcc gca gcc aac ccg gca ctg ccc tca gac ttc aag acc<br>Leu Glu Ala Ala Ala Asn Pro Ala Leu Pro Ser Asp Phe Lys Thr<br>1115                      1120                  1125 | 3442 |
| atc ctg gac tga tggccacccg cccacagcca ggccgagagc agacaccagc<br>Ile Leu Asp | 3494 |

-continued

```
1130
agccctgtca cgccgggctc tacgtcccag ggagggaggg gcggcccaca cccaggcccg      3554
caccgctggg agtctgaggc ctgagtgagt gtttggccga ggcctgcatg tccggctgaa      3614
ggctgagtgt ccggctgagg cctgagcgag tgtccagcca agggctgagt gtccagcaca      3674
cctgccgtct tcacttcccc acaggctggc gctcggctcc accccagggc cagcttttcc      3734
tcaccaggag cccggcttcc actccccaca taggaatagt ccatcccag attcgccatt      3794 gttcaccctt cgccctgccc tcctttgcct tccacccca ccatccaggt ggagaccctg      3854
agaaggaccc tgggagctct gggaatttgg agtgaccaaa ggtgtgccct gtacacaggc      3914
gaggaccctg cacctggatg ggggtccctg tgggtcaaat tgggggagg tgctgtggga      3974 gtaaaatact gaatatatga gttttttcagt tttgaaaaa a                         4015
```

<210> SEQ ID NO 2
<211> LENGTH: 1132
<212> TYPE: PRT
<213> ORGANISM: Homo sapiens

<400> SEQUENCE: 2

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270
```

```
Val Ser Pro Ala Arg Pro Ala Glu Glu Ala Thr Ser Leu Glu Gly Ala
    275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
    435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
    675                 680                 685

Ala Trp Arg Thr Phe Val Leu Arg Val Arg Ala Gln Asp Pro Pro Pro
```

-continued

```
            690                 695                 700
Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
                755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
                835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
                915                 920                 925

Pro Trp Cys Gly Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
                980                 985                 990

Ser Leu Gln Thr Val Cys Thr Asn Ile Tyr Lys Ile Leu Leu Leu Gln
                995                 1000                1005

Ala Tyr Arg Phe His Ala Cys Val Leu Gln Leu Pro Phe His Gln
   1010                1015                1020

Gln Val Trp Lys Asn Pro Thr Phe Phe Leu Arg Val Ile Ser Asp
   1025                1030                1035

Thr Ala Ser Leu Cys Tyr Ser Ile Leu Lys Ala Lys Asn Ala Gly
   1040                1045                1050

Met Ser Leu Gly Ala Lys Gly Ala Ala Gly Pro Leu Pro Ser Glu
   1055                1060                1065

Ala Val Gln Trp Leu Cys His Gln Ala Phe Leu Leu Lys Leu Thr
   1070                1075                1080

Arg His Arg Val Thr Tyr Val Pro Leu Leu Gly Ser Leu Arg Thr
   1085                1090                1095

Ala Gln Thr Gln Leu Ser Arg Lys Leu Pro Gly Thr Thr Leu Thr
   1100                1105                1110
```

Ala Leu Glu Ala Ala Ala Asn Pro Ala Leu Pro Ser Asp Phe Lys
    1115                1120                1125

Thr Ile Leu Asp
    1130

<210> SEQ ID NO 3
<211> LENGTH: 1303
<212> TYPE: DNA
<213> ORGANISM: Ovis aries
<220> FEATURE:
<221> NAME/KEY: CDS
<222> LOCATION: (194)..(1303)
<223> OTHER INFORMATION:

<400> SEQUENCE: 3

| | |
|---|---|
| agccgaggac gccgccgggg agccgaggct ccggccagcc cccagcgcgc ccagcttctg | 60 |
| cagatcagga gtcagaacgc tgcaccttcg cttcctccca gccctgcctc cttctgcaaa | 120 |
| acggagctca atagaacttg gtacttttgc cttttactct gggaggagag aagcagacga | 180 |

| | | |
|---|---|---|
| tgaggagaaa ata atg aat gtc aaa gga aaa gtg att ctg tca atg ctg<br>             Met Asn Val Lys Gly Lys Val Ile Leu Ser Met Leu<br>              1             5                  10 | 229 |
| gtt gtc tca act gtc att gtt gtg ttt tgg gaa tat atc cac agc cca<br>Val Val Ser Thr Val Ile Val Val Phe Trp Glu Tyr Ile His Ser Pro<br>        15                  20                  25 | 277 |
| gaa ggc tct ttg ttc tgg ata aac cca tca aga aac cca gaa gtc agt<br>Glu Gly Ser Leu Phe Trp Ile Asn Pro Ser Arg Asn Pro Glu Val Ser<br> 30                  35                  40 | 325 |
| ggc ggc agc agc att cag aag ggc tgg tgg ttt ccg aga tgg ttt aac<br>Gly Gly Ser Ser Ile Gln Lys Gly Trp Trp Phe Pro Arg Trp Phe Asn<br>45                50                  55                  60 | 373 |
| aat ggt tac caa gaa gaa gat gaa gac gta gac gaa gaa aag gaa caa<br>Asn Gly Tyr Gln Glu Glu Asp Glu Asp Val Asp Glu Glu Lys Glu Gln<br>               65                  70                  75 | 421 |
| aga aag gaa gac aaa agc aag ctt aag cta tcg gac tgg ttc aac cca<br>Arg Lys Glu Asp Lys Ser Lys Leu Lys Leu Ser Asp Trp Phe Asn Pro<br>            80                  85                  90 | 469 |
| ttt aaa cgc cct gag gtt gtg act atg aca gat tgg aag gca ccc gtg<br>Phe Lys Arg Pro Glu Val Val Thr Met Thr Asp Trp Lys Ala Pro Val<br>       95                  100               105 | 517 |
| gtg tgg gaa ggc act tac aac aga gcc gtc tta gac gat tac tac gcc<br>Val Trp Glu Gly Thr Tyr Asn Arg Ala Val Leu Asp Asp Tyr Tyr Ala<br>     110                  115               120 | 565 |
| aag cag aaa att acc gtc ggc ctg acg gtt ttc gcc gtc gga aga tac<br>Lys Gln Lys Ile Thr Val Gly Leu Thr Val Phe Ala Val Gly Arg Tyr<br>125               130                 135               140 | 613 |
| att gag cat tac ttg gag gag ttc tta acg tct gct aat aag cac ttc<br>Ile Glu His Tyr Leu Glu Glu Phe Leu Thr Ser Ala Asn Lys His Phe<br>                145                 150               155 | 661 |
| atg gtt ggc cac cga gtc atc ttt tac gtc atg gtg gac gac gtc tcc<br>Met Val Gly His Arg Val Ile Phe Tyr Val Met Val Asp Asp Val Ser<br>            160                  165               170 | 709 |
| agg atg cct ttg ata gag ctg ggc cct ctg cgc tcc ttc aaa gtg ttt<br>Arg Met Pro Leu Ile Glu Leu Gly Pro Leu Arg Ser Phe Lys Val Phe<br>      175                180               185 | 757 |
| gag gtc aag cct gag agg agg tgg cag gac gtc agc atg gtg cgc atg<br>Glu Val Lys Pro Glu Arg Arg Trp Gln Asp Val Ser Met Val Arg Met<br>    190                  195               200 | 805 |
| aag acc atc ggg gag cac atc gtg gcc cac atc cag cgt gag gtt gac<br>Lys Thr Ile Gly Glu His Ile Val Ala His Ile Gln Arg Glu Val Asp | 853 |

```
                205                 210                 215                 220
ttc ctc ttc tgc atg gac gtg gac cag gtc ttc caa gac gag ttc ggg                901
Phe Leu Phe Cys Met Asp Val Asp Gln Val Phe Gln Asp Glu Phe Gly
                    225                 230                 235 gtg gag acc ctg ggt gag tcg gtg gcc cag cta cag gcc tgg tgg tac                949
Val Glu Thr Leu Gly Glu Ser Val Ala Gln Leu Gln Ala Trp Trp Tyr
        240                 245                 250 aag gca gat ccc gat gag ttt acc tac gag agg cgc aag gag tct gca                997
Lys Ala Asp Pro Asp Glu Phe Thr Tyr Glu Arg Arg Lys Glu Ser Ala
            255                 260                 265 gca tac att ccc ttc ggc gaa ggg gat ttt tat tac cac gca gcc att                1045
Ala Tyr Ile Pro Phe Gly Glu Gly Asp Phe Tyr Tyr His Ala Ala Ile
        270                 275                 280 ttt ggg gga aca ccc act cag gtc ctt aac atc acc cag gaa tgc ttc                1093
Phe Gly Gly Thr Pro Thr Gln Val Leu Asn Ile Thr Gln Glu Cys Phe
285                 290                 295                 300 aaa gga atc ctc aag gac aag aaa aat gac ata gaa gcc caa tgg cat                1141
Lys Gly Ile Leu Lys Asp Lys Lys Asn Asp Ile Glu Ala Gln Trp His
            305                 310                 315 gat gag agc cat cta aac aag tat ttc ctt ctc aac aaa ccc act aaa                1189
Asp Glu Ser His Leu Asn Lys Tyr Phe Leu Leu Asn Lys Pro Thr Lys
        320                 325                 330 atc tta tcc ccg gaa tac tgc tgg gat tat cat ata ggc cta cct gcg                1237
Ile Leu Ser Pro Glu Tyr Cys Trp Asp Tyr His Ile Gly Leu Pro Ala
    335                 340                 345 gat att aag ctt gtc aag atg tct tgg cag aca aaa gag tat aat gtg                1285
Asp Ile Lys Leu Val Lys Met Ser Trp Gln Thr Lys Glu Tyr Asn Val
350                 355                 360 gtt aga aat aac gtc tga                                                        1303
Val Arg Asn Asn Val
365

<210> SEQ ID NO 4
<211> LENGTH: 369
<212> TYPE: PRT
<213> ORGANISM: Ovis aries

<400> SEQUENCE: 4

Met Asn Val Lys Gly Lys Val Ile Leu Ser Met Leu Val Val Ser Thr
1               5                   10                  15

Val Ile Val Val Phe Trp Glu Tyr Ile His Ser Pro Glu Gly Ser Leu
            20                  25                  30

Phe Trp Ile Asn Pro Ser Arg Asn Pro Glu Val Ser Gly Gly Ser Ser
        35                  40                  45

Ile Gln Lys Gly Trp Trp Phe Pro Arg Trp Phe Asn Asn Gly Tyr Gln
    50                  55                  60

Glu Glu Asp Glu Asp Val Asp Glu Lys Glu Gln Arg Lys Glu Asp
65                  70                  75                  80

Lys Ser Lys Leu Lys Leu Ser Asp Trp Phe Asn Pro Phe Lys Arg Pro
                85                  90                  95

Glu Val Val Thr Met Thr Asp Trp Lys Ala Pro Val Val Trp Glu Gly
            100                 105                 110

Thr Tyr Asn Arg Ala Val Leu Asp Asp Tyr Tyr Ala Lys Gln Lys Ile
        115                 120                 125

Thr Val Gly Leu Thr Val Phe Ala Val Gly Arg Tyr Ile Glu His Tyr
    130                 135                 140

Leu Glu Glu Phe Leu Thr Ser Ala Asn Lys His Phe Met Val Gly His
145                 150                 155                 160
```

-continued

```
Arg Val Ile Phe Tyr Val Met Val Asp Asp Val Ser Arg Met Pro Leu
                165                 170                 175
Ile Glu Leu Gly Pro Leu Arg Ser Phe Lys Val Phe Glu Val Lys Pro
            180                 185                 190
Glu Arg Arg Trp Gln Asp Val Ser Met Val Arg Met Lys Thr Ile Gly
        195                 200                 205
Glu His Ile Val Ala His Ile Gln Arg Glu Val Asp Phe Leu Phe Cys
    210                 215                 220
Met Asp Val Asp Gln Val Phe Gln Asp Glu Phe Gly Val Glu Thr Leu
225                 230                 235                 240
Gly Glu Ser Val Ala Gln Leu Gln Ala Trp Trp Tyr Lys Ala Asp Pro
                245                 250                 255
Asp Glu Phe Thr Tyr Glu Arg Arg Lys Glu Ser Ala Ala Tyr Ile Pro
                260                 265                 270
Phe Gly Glu Gly Asp Phe Tyr Tyr His Ala Ala Ile Phe Gly Gly Thr
            275                 280                 285
Pro Thr Gln Val Leu Asn Ile Thr Gln Glu Cys Phe Lys Gly Ile Leu
        290                 295                 300
Lys Asp Lys Lys Asn Asp Ile Glu Ala Gln Trp His Asp Glu Ser His
305                 310                 315                 320
Leu Asn Lys Tyr Phe Leu Leu Asn Lys Pro Thr Lys Ile Leu Ser Pro
                325                 330                 335
Glu Tyr Cys Trp Asp Tyr His Ile Gly Leu Pro Ala Asp Ile Lys Leu
                340                 345                 350
Val Lys Met Ser Trp Gln Thr Lys Glu Tyr Asn Val Val Arg Asn Asn
            355                 360                 365
Val

<210> SEQ ID NO 5
<211> LENGTH: 1617
<212> TYPE: DNA
<213> ORGANISM: Bos taurus
<220> FEATURE:
<221> NAME/KEY: CDS
<222> LOCATION: (469)..(1575)
<223> OTHER INFORMATION:

<400> SEQUENCE: 5
ccgggggccg ggccgagctg ggagcgtcga gcccgctgcc cagcgcccgc cggctccctc      60
gcgcccctgc ccgccgcccc ggaggagcgc ccggcggccg ccgacgggag agcagcggc     120 acacccccgcc ccggcacgcc cgcggggctc gggaggaggc agcgcgccga ctgttccggc   180
agccgaggac gccgccgggg agccgaggcg ccggccagcc cccagcgcgc ccagcttctg    240
cggatcaggg aaaccacgtg tcctcaagtg gccagccagc tgtccccaag aggaacttgc    300
ctggcatttg cacggaaaga cgagacactt cacaaaatca acggagtcag aaggctgcac    360
cttcgcttcc tcccagccct gcctccttct gcagaacgga gctcagtaga acttggtact    420
tttgcctttt actctaggag gagagaagca gacgatgagg agaaaata atg aat gtc    477
                                                        Met Asn Val
                                                          1
aaa gga aaa gtg att ctg tca atg ctg gtt gtc tca act gtc att gtt    525
Lys Gly Lys Val Ile Leu Ser Met Leu Val Val Ser Thr Val Ile Val
      5                  10                 15
gtg ttt tgg gaa tat atc cac agc cca gaa ggc tct ttg ttc tgg ata    573
Val Phe Trp Glu Tyr Ile His Ser Pro Glu Gly Ser Leu Phe Trp Ile
 20                  25                 30                 35
```

```
aac cca tca aga aac cca gaa gtt ggt ggc agc agc att cag aag ggc    621
Asn Pro Ser Arg Asn Pro Glu Val Gly Gly Ser Ser Ile Gln Lys Gly
            40                  45                  50 tgg tgg ctt ccg aga tgg ttt aac aat ggt tac cat gaa gaa gat gga    669
Trp Trp Leu Pro Arg Trp Phe Asn Asn Gly Tyr His Glu Glu Asp Gly
        55                  60                  65 gac ata aac gaa gaa aag gaa caa aga aac gaa gac gaa agc aag ctt    717
Asp Ile Asn Glu Glu Lys Glu Gln Arg Asn Glu Asp Glu Ser Lys Leu
    70                  75                  80 aag cta tcg gac tgg ttc aac cca ttt aaa cgc ccc gag gtt gtg acc    765
Lys Leu Ser Asp Trp Phe Asn Pro Phe Lys Arg Pro Glu Val Val Thr
85                  90                  95 atg acg aag tgg aag gct cca gtg gtg tgg gaa ggc act tac aac aga    813
Met Thr Lys Trp Lys Ala Pro Val Val Trp Glu Gly Thr Tyr Asn Arg
100                 105                 110                 115 gcc gtc tta gac aat tat tat gcc aag cag aaa att acc gtc ggc ctg    861
Ala Val Leu Asp Asn Tyr Tyr Ala Lys Gln Lys Ile Thr Val Gly Leu
                120                 125                 130 acg gtt ttc gcc gtc gga aga tac att gag cat tac ttg gag gag ttc    909
Thr Val Phe Ala Val Gly Arg Tyr Ile Glu His Tyr Leu Glu Glu Phe
            135                 140                 145 tta acg tct gct aat aag cac ttc atg gtg ggc cac cca gtc atc ttt    957
Leu Thr Ser Ala Asn Lys His Phe Met Val Gly His Pro Val Ile Phe
        150                 155                 160 tat atc atg gta gat gat gtc tcc agg atg cct ttg ata gag ttg ggt   1005
Tyr Ile Met Val Asp Asp Val Ser Arg Met Pro Leu Ile Glu Leu Gly
    165                 170                 175 cct ctg cgc tcc ttc aaa gtg ttt aag atc aag cct gag aag agg tgg   1053
Pro Leu Arg Ser Phe Lys Val Phe Lys Ile Lys Pro Glu Lys Arg Trp
180                 185                 190                 195 cag gac atc agc atg atg cgc atg aag act atc ggg gag cac att gtg   1101
Gln Asp Ile Ser Met Met Arg Met Lys Thr Ile Gly Glu His Ile Val
                200                 205                 210 gcc cac atc cag cat gag gtt gac ttc ctt ttc tgc atg gat gtg gac   1149
Ala His Ile Gln His Glu Val Asp Phe Leu Phe Cys Met Asp Val Asp
            215                 220                 225 cag gtc ttc caa gac aag ttt ggg gtg gag acc ctg ggc gag tcg gtg   1197
Gln Val Phe Gln Asp Lys Phe Gly Val Glu Thr Leu Gly Glu Ser Val
        230                 235                 240 gcc cag cta caa gcc tgg tgg tac aag gca gat ccc aat gac ttc acc   1245
Ala Gln Leu Gln Ala Trp Trp Tyr Lys Ala Asp Pro Asn Asp Phe Thr
    245                 250                 255 tac gag agg cgg aag gag tct gca gca tac att ccc ttc ggc gaa ggg   1293
Tyr Glu Arg Arg Lys Glu Ser Ala Ala Tyr Ile Pro Phe Gly Glu Gly
260                 265                 270                 275 gat ttt tat tac cat gca gcc att ttt ggg gga aca ccc act cag gtc   1341
Asp Phe Tyr Tyr His Ala Ala Ile Phe Gly Gly Thr Pro Thr Gln Val
                280                 285                 290 ctt aac atc acc cag gaa tgc ttc aaa gga atc ctc aag gac aag aaa   1389
Leu Asn Ile Thr Gln Glu Cys Phe Lys Gly Ile Leu Lys Asp Lys Lys
            295                 300                 305 aat gac ata gaa gcc caa tgg cat gat gaa agc cat cta aac aag tat   1437
Asn Asp Ile Glu Ala Gln Trp His Asp Glu Ser His Leu Asn Lys Tyr
        310                 315                 320 ttc ctt ctc aac aaa cct act aaa atc tta tcc ccg gaa tac tgc tgg   1485
Phe Leu Leu Asn Lys Pro Thr Lys Ile Leu Ser Pro Glu Tyr Cys Trp
    325                 330                 335 gat tat cac ata ggc cta cct gcg gat att aag ctt gtc aag atg tct   1533
Asp Tyr His Ile Gly Leu Pro Ala Asp Ile Lys Leu Val Lys Met Ser
```

```
                340              345              350              355
tgg cag aca aaa gag tat aat gtg gtt aga aat aat gtc tga                    1575
Trp Gln Thr Lys Glu Tyr Asn Val Val Arg Asn Asn Val
            360                              365 ctttgtgcca gtacatttct gaatttgaga gagtattatt ct                             1617
```

<210> SEQ ID NO 6
<211> LENGTH: 368
<212> TYPE: PRT
<213> ORGANISM: Bos taurus

<400> SEQUENCE: 6

```
Met Asn Val Lys Gly Lys Val Ile Leu Ser Met Leu Val Val Ser Thr
1               5                   10                  15

Val Ile Val Val Phe Trp Glu Tyr Ile His Ser Pro Glu Gly Ser Leu
            20                  25                  30

Phe Trp Ile Asn Pro Ser Arg Asn Pro Glu Val Gly Ser Ser Ile
        35                  40                  45

Gln Lys Gly Trp Trp Leu Pro Arg Trp Phe Asn Asn Gly Tyr His Glu
    50                  55                  60

Glu Asp Gly Asp Ile Asn Glu Glu Lys Glu Gln Arg Asn Glu Asp Glu
65                  70                  75                  80

Ser Lys Leu Lys Leu Ser Asp Trp Phe Asn Pro Phe Lys Arg Pro Glu
                85                  90                  95

Val Val Thr Met Thr Lys Trp Lys Ala Pro Val Val Trp Glu Gly Thr
            100                 105                 110

Tyr Asn Arg Ala Val Leu Asp Asn Tyr Tyr Ala Lys Gln Lys Ile Thr
        115                 120                 125

Val Gly Leu Thr Val Phe Ala Val Gly Arg Tyr Ile Glu His Tyr Leu
    130                 135                 140

Glu Glu Phe Leu Thr Ser Ala Asn Lys His Phe Met Val Gly His Pro
145                 150                 155                 160

Val Ile Phe Tyr Ile Met Val Asp Asp Val Ser Arg Met Pro Leu Ile
                165                 170                 175

Glu Leu Gly Pro Leu Arg Ser Phe Lys Val Phe Lys Ile Lys Pro Glu
            180                 185                 190

Lys Arg Trp Gln Asp Ile Ser Met Met Arg Met Lys Thr Ile Gly Glu
        195                 200                 205

His Ile Val Ala His Ile Gln His Glu Val Asp Phe Leu Phe Cys Met
    210                 215                 220

Asp Val Asp Gln Val Phe Gln Asp Lys Phe Gly Val Glu Thr Leu Gly
225                 230                 235                 240

Glu Ser Val Ala Gln Leu Gln Ala Trp Trp Tyr Lys Ala Asp Pro Asn
                245                 250                 255

Asp Phe Thr Tyr Glu Arg Arg Lys Glu Ser Ala Ala Tyr Ile Pro Phe
            260                 265                 270

Gly Glu Gly Asp Phe Tyr Tyr His Ala Ala Ile Phe Gly Gly Thr Pro
        275                 280                 285

Thr Gln Val Leu Asn Ile Thr Gln Glu Cys Phe Lys Gly Ile Leu Lys
    290                 295                 300

Asp Lys Lys Asn Asp Ile Glu Ala Gln Trp His Asp Glu Ser His Leu
305                 310                 315                 320

Asn Lys Tyr Phe Leu Leu Asn Lys Pro Thr Lys Ile Leu Ser Pro Glu
                325                 330                 335
```

```
Tyr Cys Trp Asp Tyr His Ile Gly Leu Pro Ala Asp Ile Lys Leu Val
            340                 345                 350

Lys Met Ser Trp Gln Thr Lys Glu Tyr Asn Val Val Arg Asn Asn Val
        355                 360                 365

<210> SEQ ID NO 7
<211> LENGTH: 1269
<212> TYPE: DNA
<213> ORGANISM: Sus scrofa
<220> FEATURE:
<221> NAME/KEY: CDS
<222> LOCATION: (16)..(1131)
<223> OTHER INFORMATION:

<400> SEQUENCE: 7
catgaggaga aaata atg aat gtc aaa gga aga gtg gtt ctg tca atg ctg        51
                 Met Asn Val Lys Gly Arg Val Val Leu Ser Met Leu
                  1               5                  10 ctt gtc tca act gta atg gtt gtg ttt tgg gaa tac atc aac agc cca        99
Leu Val Ser Thr Val Met Val Val Phe Trp Glu Tyr Ile Asn Ser Pro
         15                  20                  25 gaa ggt tct ttg ttc tgg ata tac cag tca aaa aac cca gaa gtt ggc       147
Glu Gly Ser Leu Phe Trp Ile Tyr Gln Ser Lys Asn Pro Glu Val Gly
     30                  35                  40 agc agt gct cag agg ggc tgg tgg ttt ccg agc tgg ttt aac aat ggg       195
Ser Ser Ala Gln Arg Gly Trp Trp Phe Pro Ser Trp Phe Asn Asn Gly
 45                  50                  55                  60 act cac agt tac cac gaa gaa gaa gac gct ata ggc aac gaa aag gaa       243
Thr His Ser Tyr His Glu Glu Glu Asp Ala Ile Gly Asn Glu Lys Glu
                 65                  70                  75 caa aga aaa gaa gac aac aga gga gag ctt ccg cta gtg gac tgg ttt       291
Gln Arg Lys Glu Asp Asn Arg Gly Glu Leu Pro Leu Val Asp Trp Phe
             80                  85                  90 aat cct gag aaa cgc cca gag gtc gtg acc ata acc aga tgg aag gct       339
Asn Pro Glu Lys Arg Pro Glu Val Val Thr Ile Thr Arg Trp Lys Ala
         95                 100                 105 cca gtg gta tgg gaa ggc act tac aac aga gcc gtc tta gat aat tat       387
Pro Val Val Trp Glu Gly Thr Tyr Asn Arg Ala Val Leu Asp Asn Tyr
    110                 115                 120 tat gcc aaa cag aaa att acc gtg ggc ttg acg gtt ttt gct gtc gga       435
Tyr Ala Lys Gln Lys Ile Thr Val Gly Leu Thr Val Phe Ala Val Gly
125                 130                 135                 140 aga tac att gag cat tac ttg gag gag ttc tta ata tct gca aat aca       483
Arg Tyr Ile Glu His Tyr Leu Glu Glu Phe Leu Ile Ser Ala Asn Thr
                145                 150                 155 tac ttc atg gtt ggc cac aaa gtc atc ttt tac atc atg gtg gat gat       531
Tyr Phe Met Val Gly His Lys Val Ile Phe Tyr Ile Met Val Asp Asp
            160                 165                 170 atc tcc agg atg cct ttg ata gag ctg ggt cct ctg cgt tcc ttt aaa       579
Ile Ser Arg Met Pro Leu Ile Glu Leu Gly Pro Leu Arg Ser Phe Lys
        175                 180                 185 gtg ttt gag atc aag tcc gag aag agg tgg caa gac atc agc atg atg       627
Val Phe Glu Ile Lys Ser Glu Lys Arg Trp Gln Asp Ile Ser Met Met
    190                 195                 200 cgc atg aag acc atc ggg gag cac atc ctg gcc cac atc cag cac gag       675
Arg Met Lys Thr Ile Gly Glu His Ile Leu Ala His Ile Gln His Glu
205                 210                 215                 220 gtg gac ttc ctc ttc tgc atg gac gtg gat cag gtc ttc caa aac aac       723
Val Asp Phe Leu Phe Cys Met Asp Val Asp Gln Val Phe Gln Asn Asn
                225                 230                 235 ttt ggg gtg gag acc ctg ggc cag tcg gtg gct cag cta cag gcc tgg       771
```

-continued

```
Phe Gly Val Glu Thr Leu Gly Gln Ser Val Ala Gln Leu Gln Ala Trp
            240                 245                 250 tgg tac aag gca cat cct gac gag ttc acc tac gag agg cgg aag gag      819
Trp Tyr Lys Ala His Pro Asp Glu Phe Thr Tyr Glu Arg Arg Lys Glu
        255                 260                 265 tcc gca gcc tac att ccg ttt ggc cag ggg gat ttt tat tac cac gca      867
Ser Ala Ala Tyr Ile Pro Phe Gly Gln Gly Asp Phe Tyr Tyr His Ala
    270                 275                 280 gcc att ttt ggg gga aca ccc act cag gtt cta aac atc act cag gag      915
Ala Ile Phe Gly Gly Thr Pro Thr Gln Val Leu Asn Ile Thr Gln Glu
285                 290                 295                 300 tgc ttc aag gga atc ctc cag gac aag gaa aat gac ata gaa gcc gag      963
Cys Phe Lys Gly Ile Leu Gln Asp Lys Glu Asn Asp Ile Glu Ala Glu
                305                 310                 315 tgg cat gat gaa agc cat cta aac aag tat ttc ctt ctc aac aaa ccc     1011
Trp His Asp Glu Ser His Leu Asn Lys Tyr Phe Leu Leu Asn Lys Pro
            320                 325                 330 act aaa atc tta tcc cca gaa tac tgc tgg gat tat cat ata ggc atg     1059
Thr Lys Ile Leu Ser Pro Glu Tyr Cys Trp Asp Tyr His Ile Gly Met
        335                 340                 345 tct gtg gat att agg att gtc aag ata gct tgg cag aaa aaa gag tat     1107
Ser Val Asp Ile Arg Ile Val Lys Ile Ala Trp Gln Lys Lys Glu Tyr
    350                 355                 360 aat ttg gtt aga aat aac atc tga ctttaaattg tgccagcagt tttctgaatt    1161
Asn Leu Val Arg Asn Asn Ile
365                 370 tgaaagagta ttactctggc tacttctcca gagaagtagc acttaatttt aactttttaaa  1221 aaaatactaa caaaatacca acacagtaag tacatattat tcttcctt                1269

<210> SEQ ID NO 8
<211> LENGTH: 371
<212> TYPE: PRT
<213> ORGANISM: Sus scrofa

<400> SEQUENCE: 8

Met Asn Val Lys Gly Arg Val Val Leu Ser Met Leu Leu Val Ser Thr
1               5                   10                  15

Val Met Val Val Phe Trp Glu Tyr Ile Asn Ser Pro Glu Gly Ser Leu
            20                  25                  30

Phe Trp Ile Tyr Gln Ser Lys Asn Pro Glu Val Gly Ser Ser Ala Gln
        35                  40                  45

Arg Gly Trp Trp Phe Pro Ser Trp Phe Asn Asn Gly Thr His Ser Tyr
    50                  55                  60

His Glu Glu Glu Asp Ala Ile Gly Asn Glu Lys Glu Gln Arg Lys Glu
65                  70                  75                  80

Asp Asn Arg Gly Glu Leu Pro Leu Val Asp Trp Phe Asn Pro Glu Lys
                85                  90                  95

Arg Pro Glu Val Val Thr Ile Thr Arg Trp Lys Ala Pro Val Val Trp
            100                 105                 110

Glu Gly Thr Tyr Asn Arg Ala Val Leu Asp Asn Tyr Tyr Ala Lys Gln
        115                 120                 125

Lys Ile Thr Val Gly Leu Thr Val Phe Ala Val Gly Arg Tyr Ile Glu
    130                 135                 140

His Tyr Leu Glu Glu Phe Leu Ile Ser Ala Asn Thr Tyr Phe Met Val
145                 150                 155                 160

Gly His Lys Val Ile Phe Tyr Ile Met Val Asp Asp Ile Ser Arg Met
                165                 170                 175
```

```
Pro Leu Ile Glu Leu Gly Pro Leu Arg Ser Phe Lys Val Phe Glu Ile
            180                 185                 190

Lys Ser Glu Lys Arg Trp Gln Asp Ile Ser Met Met Arg Met Lys Thr
            195                 200                 205

Ile Gly Glu His Ile Leu Ala His Ile Gln His Glu Val Asp Phe Leu
            210                 215                 220

Phe Cys Met Asp Val Asp Gln Val Phe Gln Asn Asn Phe Gly Val Glu
225                 230                 235                 240

Thr Leu Gly Gln Ser Val Ala Gln Leu Gln Ala Trp Trp Tyr Lys Ala
            245                 250                 255

His Pro Asp Glu Phe Thr Tyr Glu Arg Arg Lys Glu Ser Ala Ala Tyr
            260                 265                 270

Ile Pro Phe Gly Gln Gly Asp Phe Tyr Tyr His Ala Ala Ile Phe Gly
            275                 280                 285

Gly Thr Pro Thr Gln Val Leu Asn Ile Thr Gln Glu Cys Phe Lys Gly
            290                 295                 300

Ile Leu Gln Asp Lys Glu Asn Asp Ile Glu Ala Glu Trp His Asp Glu
305                 310                 315                 320

Ser His Leu Asn Lys Tyr Phe Leu Leu Asn Lys Pro Thr Lys Ile Leu
            325                 330                 335

Ser Pro Glu Tyr Cys Trp Asp Tyr His Ile Gly Met Ser Val Asp Ile
            340                 345                 350

Arg Ile Val Lys Ile Ala Trp Gln Lys Lys Glu Tyr Asn Leu Val Arg
            355                 360                 365

Asn Asn Ile
370

<210> SEQ ID NO 9
<211> LENGTH: 3373
<212> TYPE: DNA
<213> ORGANISM: Homo sapiens
<220> FEATURE:
<221> NAME/KEY: CDS
<222> LOCATION: (104)..(1201)
<223> OTHER INFORMATION:

<400> SEQUENCE: 9
gcctggcgtt ccaggggcgg ccggatgtgg cctgcctttg cggagggtgc gctccggcca      60
cgaaaagcgg actgtggatc tgccacctgc aagcagctcg gcc atg tgg ctc cgg      115
                                              Met Trp Leu Arg
                                                1 agc cat cgt cag ctc tgc ctg gcc ttc ctg cta gtc tgt gtc ctc tct      163
Ser His Arg Gln Leu Cys Leu Ala Phe Leu Leu Val Cys Val Leu Ser
 5                  10                  15                  20 gta atc ttc ttc ctc cat atc cat caa gac agc ttt cca cat ggc cta      211
Val Ile Phe Phe Leu His Ile His Gln Asp Ser Phe Pro His Gly Leu
                25                  30                  35 ggc ctg tcg atc ctg tgt cca gac cgc gcg ctg gtg aca ccc cca gtg      259
Gly Leu Ser Ile Leu Cys Pro Asp Arg Arg Leu Val Thr Pro Pro Val
            40                  45                  50 gcc atc ttc tgc ctg ccg ggt act gcg atg ggc ccc aac gcc tcc tct      307
Ala Ile Phe Cys Leu Pro Gly Thr Ala Met Gly Pro Asn Ala Ser Ser
        55                  60                  65 tcc tgt ccc cag cac cct gct tcc ctc tcc ggc acc tgg act gtc tac      355
Ser Cys Pro Gln His Pro Ala Ser Leu Ser Gly Thr Trp Thr Val Tyr
    70                  75                  80 ccc aat ggc cgg ttt ggt aat cag atg gga cag tat gcc acg ctg ctg      403
```

|  |  |  |  |  |  |  |  |  |  |  |  |  |  |  |  |
|---|---|---|---|---|---|---|---|---|---|---|---|---|---|---|---|
| Pro | Asn | Gly | Arg | Phe | Gly | Asn | Gln | Met | Gly | Gln | Tyr | Ala | Thr | Leu | Leu |
| 85 |  |  |  | 90 |  |  |  | 95 |  |  |  | Ala | Thr | Leu | 100 |

| gct | ctg | gcc | cag | ctc | aac | ggc | cgc | cgg | gcc | ttt | atc | ctg | cct | gcc | atg | 451 |
|---|---|---|---|---|---|---|---|---|---|---|---|---|---|---|---|---|
| Ala | Leu | Ala | Gln | Leu | Asn | Gly | Arg | Arg | Ala | Phe | Ile | Leu | Pro | Ala | Met |  |
|  |  |  |  | 105 |  |  |  | 110 |  |  |  |  | 115 |  |  |  |

| cat | gcc | gcc | ctg | gcc | ccg | gta | ttc | cgc | atc | acc | ctg | ccc | gtg | ctg | gcc | 499 |
|---|---|---|---|---|---|---|---|---|---|---|---|---|---|---|---|---|
| His | Ala | Ala | Leu | Ala | Pro | Val | Phe | Arg | Ile | Thr | Leu | Pro | Val | Leu | Ala |  |
|  |  | 120 |  |  |  |  | 125 |  |  |  | 130 |  |  |  |  |  |

| cca | gaa | gtg | gac | agc | cgc | acg | ccg | tgg | cgg | gag | ctg | cag | ctt | cac | gac | 547 |
|---|---|---|---|---|---|---|---|---|---|---|---|---|---|---|---|---|
| Pro | Glu | Val | Asp | Ser | Arg | Thr | Pro | Trp | Arg | Glu | Leu | Gln | Leu | His | Asp |  |
|  |  | 135 |  |  |  | 140 |  |  |  |  | 145 |  |  |  |  |  |

| tgg | atg | tcg | gag | gag | tac | gcg | gac | ttg | aga | gat | cct | ttc | ctg | aag | ctc | 595 |
|---|---|---|---|---|---|---|---|---|---|---|---|---|---|---|---|---|
| Trp | Met | Ser | Glu | Glu | Tyr | Ala | Asp | Leu | Arg | Asp | Pro | Phe | Leu | Lys | Leu |  |
|  | 150 |  |  |  | 155 |  |  |  |  | 160 |  |  |  |  |  |  |

| tct | ggc | ttc | ccc | tgc | tct | tgg | act | ttc | ttc | cac | cat | ctc | cgg | gaa | cag | 643 |
|---|---|---|---|---|---|---|---|---|---|---|---|---|---|---|---|---|
| Ser | Gly | Phe | Pro | Cys | Ser | Trp | Thr | Phe | Phe | His | His | Leu | Arg | Glu | Gln |  |
| 165 |  |  |  | 170 |  |  |  |  | 175 |  |  |  |  | 180 |  |  |

| atc | cgc | aga | gag | ttc | acc | ctg | cac | gac | cac | ctt | cgg | gaa | gag | gcg | cag | 691 |
|---|---|---|---|---|---|---|---|---|---|---|---|---|---|---|---|---|
| Ile | Arg | Arg | Glu | Phe | Thr | Leu | His | Asp | His | Leu | Arg | Glu | Glu | Ala | Gln |  |
|  |  |  |  | 185 |  |  |  |  | 190 |  |  |  |  | 195 |  |  |

| agt | gtg | ctg | ggt | cag | ctc | cgc | ctg | ggc | cgc | aca | ggg | gac | cgc | ccg | cgc | 739 |
|---|---|---|---|---|---|---|---|---|---|---|---|---|---|---|---|---|
| Ser | Val | Leu | Gly | Gln | Leu | Arg | Leu | Gly | Arg | Thr | Gly | Asp | Arg | Pro | Arg |  |
|  |  | 200 |  |  |  |  | 205 |  |  |  | 210 |  |  |  |  |  |

| acc | ttt | gtc | ggc | gtc | cac | gtg | cgc | cgt | ggg | gac | tat | ctg | cag | gtt | atg | 787 |
|---|---|---|---|---|---|---|---|---|---|---|---|---|---|---|---|---|
| Thr | Phe | Val | Gly | Val | His | Val | Arg | Arg | Gly | Asp | Tyr | Leu | Gln | Val | Met |  |
|  |  | 215 |  |  |  |  | 220 |  |  |  | 225 |  |  |  |  |  |

| cct | cag | cgc | tgg | aag | ggt | gtg | gtg | ggc | gac | agc | gcc | tac | ctc | cgg | cag | 835 |
|---|---|---|---|---|---|---|---|---|---|---|---|---|---|---|---|---|
| Pro | Gln | Arg | Trp | Lys | Gly | Val | Val | Gly | Asp | Ser | Ala | Tyr | Leu | Arg | Gln |  |
| 230 |  |  |  |  | 235 |  |  |  |  | 240 |  |  |  |  |  |  |

| gcc | atg | gac | tgg | ttc | cgg | gca | cgg | cac | gaa | gcc | ccc | gtt | ttc | gtg | gtc | 883 |
|---|---|---|---|---|---|---|---|---|---|---|---|---|---|---|---|---|
| Ala | Met | Asp | Trp | Phe | Arg | Ala | Arg | His | Glu | Ala | Pro | Val | Phe | Val | Val |  |
| 245 |  |  |  |  | 250 |  |  |  |  | 255 |  |  |  |  | 260 |  |

| acc | agc | aac | ggc | atg | gag | tgg | tgt | aaa | gaa | aac | atc | gac | acc | tcc | cag | 931 |
|---|---|---|---|---|---|---|---|---|---|---|---|---|---|---|---|---|
| Thr | Ser | Asn | Gly | Met | Glu | Trp | Cys | Lys | Glu | Asn | Ile | Asp | Thr | Ser | Gln |  |
|  |  |  |  | 265 |  |  |  |  | 270 |  |  |  |  | 275 |  |  |

| ggc | gat | gtg | acg | ttt | gct | ggc | gat | gga | cag | gag | gct | aca | ccg | tgg | aaa | 979 |
|---|---|---|---|---|---|---|---|---|---|---|---|---|---|---|---|---|
| Gly | Asp | Val | Thr | Phe | Ala | Gly | Asp | Gly | Gln | Glu | Ala | Thr | Pro | Trp | Lys |  |
|  |  |  | 280 |  |  |  |  | 285 |  |  |  |  | 290 |  |  |  |

| gac | ttt | gcc | ctg | ctc | aca | cag | tgc | aac | cac | acc | att | atg | acc | att | ggc | 1027 |
|---|---|---|---|---|---|---|---|---|---|---|---|---|---|---|---|---|
| Asp | Phe | Ala | Leu | Leu | Thr | Gln | Cys | Asn | His | Thr | Ile | Met | Thr | Ile | Gly |  |
|  |  | 295 |  |  |  |  | 300 |  |  |  |  | 305 |  |  |  |  |

| acc | ttc | ggc | ttc | tgg | gct | gcc | tac | ctg | gct | ggc | gga | gac | act | gtc | tac | 1075 |
|---|---|---|---|---|---|---|---|---|---|---|---|---|---|---|---|---|
| Thr | Phe | Gly | Phe | Trp | Ala | Ala | Tyr | Leu | Ala | Gly | Gly | Asp | Thr | Val | Tyr |  |
|  | 310 |  |  |  |  | 315 |  |  |  |  | 320 |  |  |  |  |  |

| ctg | gcc | aac | ttc | acc | ctg | cca | gac | tct | gag | ttc | ctg | aag | atc | ttt | aag | 1123 |
|---|---|---|---|---|---|---|---|---|---|---|---|---|---|---|---|---|
| Leu | Ala | Asn | Phe | Thr | Leu | Pro | Asp | Ser | Glu | Phe | Leu | Lys | Ile | Phe | Lys |  |
| 325 |  |  |  |  | 330 |  |  |  |  | 335 |  |  |  |  | 340 |  |

| ccg | gag | gcg | gcc | ttc | ctg | ccc | gag | tgg | gtg | ggc | att | aat | gca | gac | ttg | 1171 |
|---|---|---|---|---|---|---|---|---|---|---|---|---|---|---|---|---|
| Pro | Glu | Ala | Ala | Phe | Leu | Pro | Glu | Trp | Val | Gly | Ile | Asn | Ala | Asp | Leu |  |
|  |  |  | 345 |  |  |  |  | 350 |  |  |  |  | 355 |  |  |  |

| tct | cca | ctc | tgg | aca | ttg | gct | aag | cct | tga | gagccaggga | gactttctga |  |  |  |  | 1221 |
|---|---|---|---|---|---|---|---|---|---|---|---|---|---|---|---|---|
| Ser | Pro | Leu | Trp | Thr | Leu | Ala | Lys | Pro |  |  |  |  |  |  |  |  |
|  | 360 |  |  |  |  |  | 365 |  |  |  |  |  |  |  |  |  | agtagcctga tctttctaga gccagcagta cgtggcttca gaggcctggc atcttctgga       1281 gaagcttgtg gtgttcctga agcaaatggg tgcccgtatc cagagtgatt ctagttggga       1341 gagttggaga gaaggggggac gtttctggaa ctgtctgaat attctagaac tagcaaaaca      1401 tctttttcctg atggctggca ggcagttcta gaagccacag tgcccacctg ctcttcccag      1461

-continued

```
cccatatcta cagtacttcc agatggctgc ccccaggaat ggggaactct ccctctggtc    1521
tactctagaa gagggttac ttctcccctg gtcctccaa agactgaagg agcatatgat      1581
tgctccagag caagcattca ccaagtcccc ttctgtgttt ctggagtgat tctagaggga    1641
gacttgttct agagaggacc aggtttgatg cctgtgaaga accctgcagg gcccttatgg    1701
acaggatggg gttctggaaa tccagataac taaggtgaag aatctttta gtttttttt     1761
tttttttttg agacagggt ctcgctctgt tgcccaggct ggagtgcagt ggcgtgatct    1821
tggctcactg caacttccgc ctcctgtgtt caagcgattc tcctgtctca gcctcctgag   1881
tagatgggac tacaggcaca ggccattatg cctggctaat ttttgtattt ttagtagaga   1941
cagggtttca ccatgttggc cgggatggtc tcgatctcct gaccttgtca tccacctgtc   2001
ttggcctccc aaagtgctgg gattactggc atgagccact gtgcccagcc cggatatttt   2061
tttttaatta tttatttatt tatttattta ttgagacgga gtcttgctct gtagcccagg   2121
ccagagtgca gtggcgcgat ctcagctcac tgcaagctct gcctcccggg ttcatgccat   2181
tctgcctcag cctcctgagt agctgggact acaggcgccc gccaccacgc ccggctaatt   2241
tttttttgtat tttagtaga cgggggtttt catcgtgtta accaggatgg tctcgatctc   2301
ctgacctcgt gatctgccca cctcggcctc ccacagtgct gggattaccg gcgtgagcca   2361
ccatgcctgg cccggataat ttttttttaat ttttgtagag acgaggtctt gtgatattgc  2421
ccaggctgtt cttcaactcc tgggctcaag cagtcctccc accttggcct cccagaatgc   2481
tgggtttata gatgtgagcc agcacaccgg gccaagtgaa gaatctaatg aatgtgcaac   2541
ctaattgtag catctaatga atgttccacc attgctggaa aaattgagat ggaaaacaaa   2601
ccatctctag ttggccagcg tcttgctctg ttcacagtct ctggaaaagc tggggtagtt   2661
ggtgagcaga gcgggactct gtccaacaag ccccacagcc cctcaaagac tttttttgt   2721
ttgttttgag cagacaggct aaaatgtgaa cgtgggtga gggatcactg ccaaaatggt    2781
acagcttctg gagcagaact ttccagggat ccagggacac ttttttttaa agctcataaa   2841
ctgccaagag ctccatatat tgggtgtgag ttcaggttgc ctctcacaat gaaggaagtt   2901
ggtctttgtc tgcaggtggg ctgctgaggg tctgggatct gttttctgga agtgtgcagg   2961
tataaacaca ccctctgtgc ttgtgacaaa ctggcaggta ccgtgctcat tgctaaccac   3021
tgtctgtccc tgaactccca gaaccactac atctggcttt gggcaggtct gagataaaac   3081
gatctaaagg taggcagacc ctggacccag cctcagatcc aggcaggagc acgaggtctg   3141
gccaaggtgg acgggttgt cgagatctca ggagcccctt gctgttttt ggagggtgaa    3201
agaagaaacc ttaaacatag tcagctctga tcacatcccc tgtctactca tccagacccc   3261
atgcctgtag gcttatcagg gagttacagt tacaattgtt acagtactgt tcccaactca   3321
gctgccacgg gtgagagagc aggaggtatg aattaaaagt ctacagcact aa           3373
```

<210> SEQ ID NO 10
<211> LENGTH: 365
<212> TYPE: PRT
<213> ORGANISM: Homo sapiens

<400> SEQUENCE: 10

Met Trp Leu Arg Ser His Arg Gln Leu Cys Leu Ala Phe Leu Leu Val
1               5                   10                  15

Cys Val Leu Ser Val Ile Phe Phe Leu His Ile His Gln Asp Ser Phe
            20                  25                  30

Pro His Gly Leu Gly Leu Ser Ile Leu Cys Pro Asp Arg Arg Leu Val

|     |     |     |     | 35  |     |     |     |     | 40  |     |     |     |     | 45  |     |
|-----|-----|-----|-----|-----|-----|-----|-----|-----|-----|-----|-----|-----|-----|-----|-----|

Thr Pro Pro Val Ala Ile Phe Cys Leu Pro Gly Thr Ala Met Gly Pro
    50                55                60

Asn Ala Ser Ser Cys Pro Gln His Pro Ala Ser Leu Ser Gly Thr
65               70               75               80

Trp Thr Val Tyr Pro Asn Gly Arg Phe Gly Asn Gln Met Gly Gln Tyr
            85               90              95

Ala Thr Leu Leu Ala Leu Ala Gln Leu Asn Gly Arg Arg Ala Phe Ile
           100            105           110

Leu Pro Ala Met His Ala Ala Leu Ala Pro Val Phe Arg Ile Thr Leu
        115            120           125

Pro Val Leu Ala Pro Glu Val Asp Ser Arg Thr Pro Trp Arg Glu Leu
  130               135           140

Gln Leu His Asp Trp Met Ser Glu Glu Tyr Ala Asp Leu Arg Asp Pro
145              150            155           160

Phe Leu Lys Leu Ser Gly Phe Pro Cys Ser Trp Thr Phe Phe His His
           165            170           175

Leu Arg Glu Gln Ile Arg Arg Glu Phe Thr Leu His Asp His Leu Arg
        180            185           190

Glu Glu Ala Gln Ser Val Leu Gly Gln Leu Arg Leu Gly Arg Thr Gly
        195            200           205

Asp Arg Pro Arg Thr Phe Val Gly Val His Val Arg Arg Gly Asp Tyr
  210               215           220

Leu Gln Val Met Pro Gln Arg Trp Lys Gly Val Val Gly Asp Ser Ala
225              230            235           240

Tyr Leu Arg Gln Ala Met Asp Trp Phe Arg Ala Arg His Glu Ala Pro
           245            250           255

Val Phe Val Val Thr Ser Asn Gly Met Glu Trp Cys Lys Glu Asn Ile
        260            265           270

Asp Thr Ser Gln Gly Asp Val Thr Phe Ala Gly Asp Gly Gln Glu Ala
        275            280           285

Thr Pro Trp Lys Asp Phe Ala Leu Leu Thr Gln Cys Asn His Thr Ile
  290               295           300

Met Thr Ile Gly Thr Phe Gly Phe Trp Ala Ala Tyr Leu Ala Gly Gly
305              310            315           320

Asp Thr Val Tyr Leu Ala Asn Phe Thr Leu Pro Asp Ser Glu Phe Leu
           325            330           335

Lys Ile Phe Lys Pro Glu Ala Ala Phe Leu Pro Glu Trp Val Gly Ile
        340            345           350

Asn Ala Asp Leu Ser Pro Leu Trp Thr Leu Ala Lys Pro
        355            360           365

```
<210> SEQ ID NO 11
<211> LENGTH: 1062
<212> TYPE: DNA
<213> ORGANISM: Homo sapiens
<220> FEATURE:
<221> NAME/KEY: CDS
<222> LOCATION: (1)..(1062)
<223> OTHER INFORMATION:

<400> SEQUENCE: 11
```

| atg | gcc | gag | gtg | ttg | cgg | acg | ctg | gcc | gga | aaa | cca | aaa | tgc | cac | gca | 48 |
|-----|-----|-----|-----|-----|-----|-----|-----|-----|-----|-----|-----|-----|-----|-----|-----|----|
| Met | Ala | Glu | Val | Leu | Arg | Thr | Leu | Ala | Gly | Lys | Pro | Lys | Cys | His | Ala |    |
| 1   |     |     |     | 5   |     |     |     |     | 10  |     |     |     |     | 15  |     |    |

| ctt | cga | cct | atg | atc | ctt | ttc | cta | ata | atg | ctt | gtc | ttg | gtc | ttg | ttt | 96 |
|-----|-----|-----|-----|-----|-----|-----|-----|-----|-----|-----|-----|-----|-----|-----|-----|----|

-continued

| | | |
|---|---|---|
| Leu Arg Pro Met Ile Leu Phe Leu Ile Met Leu Val Leu Val Leu Phe<br>20 25 30 | | |
| ggt tac ggg gtc cta agc ccc aga agt cta atg cca gga agc ctg gaa<br>Gly Tyr Gly Val Leu Ser Pro Arg Ser Leu Met Pro Gly Ser Leu Glu<br>35 40 45 | 144 | |
| cgg ggg ttc tgc atg gct gtt agg gaa cct gac cat ctg cag cgc gtc<br>Arg Gly Phe Cys Met Ala Val Arg Glu Pro Asp His Leu Gln Arg Val<br>50 55 60 | 192 | |
| tcg ttg cca agg atg gtc tac ccc cag cca aag gtg ctg aca ccg tgg<br>Ser Leu Pro Arg Met Val Tyr Pro Gln Pro Lys Val Leu Thr Pro Trp<br>65 70 75 80 | 240 | |
| aag gat gtc ctc gtg gtg acc cct tgg ctg gct ccc att gtc tgg gag<br>Lys Asp Val Leu Val Val Thr Pro Trp Leu Ala Pro Ile Val Trp Glu<br>85 90 95 | 288 | |
| ggc aca ttc aac atc gac atc ctc aac gag cag ttc agg ctc cag aac<br>Gly Thr Phe Asn Ile Asp Ile Leu Asn Glu Gln Phe Arg Leu Gln Asn<br>100 105 110 | 336 | |
| acc acc att ggg tta act gtg ttt gcc atc aag aaa tac gtg gct ttc<br>Thr Thr Ile Gly Leu Thr Val Phe Ala Ile Lys Lys Tyr Val Ala Phe<br>115 120 125 | 384 | |
| ctg aag ctg ttc ctg gag acg gcg gag aag cac ttc atg gtg ggc cac<br>Leu Lys Leu Phe Leu Glu Thr Ala Glu Lys His Phe Met Val Gly His<br>130 135 140 | 432 | |
| cgt gtc cac tac tat gtc ttc acc gac cag ctg gcc gcg gtg ccc cgc<br>Arg Val His Tyr Tyr Val Phe Thr Asp Gln Leu Ala Ala Val Pro Arg<br>145 150 155 160 | 480 | |
| gtg acg ctg ggg acc ggt cgg cag ctg tca gtg ctg gag gtg cgc gcc<br>Val Thr Leu Gly Thr Gly Arg Gln Leu Ser Val Leu Glu Val Arg Ala<br>165 170 175 | 528 | |
| tac aag cgc tgg cag gac gtg tcc atg cgc cgc atg gag atg atc agt<br>Tyr Lys Arg Trp Gln Asp Val Ser Met Arg Arg Met Glu Met Ile Ser<br>180 185 190 | 576 | |
| gac ttc tgc gag cgg cgc ttc ctc agc gag gtg gat tac ctg gtg tgc<br>Asp Phe Cys Glu Arg Arg Phe Leu Ser Glu Val Asp Tyr Leu Val Cys<br>195 200 205 | 624 | |
| gtg gac gtg gac atg gag ttc cgc gac cac gtg ggc gtg gag atc ctg<br>Val Asp Val Asp Met Glu Phe Arg Asp His Val Gly Val Glu Ile Leu<br>210 215 220 | 672 | |
| act ccg ctg ttc ggc acc ctg cac ccc ggc ttc tac gga agc agc cgg<br>Thr Pro Leu Phe Gly Thr Leu His Pro Gly Phe Tyr Gly Ser Ser Arg<br>225 230 235 240 | 720 | |
| gag gcc ttc acc tac gag cgc cgg ccc cag tcc cag gcc tac atc ccc<br>Glu Ala Phe Thr Tyr Glu Arg Arg Pro Gln Ser Gln Ala Tyr Ile Pro<br>245 250 255 | 768 | |
| aag gac gag ggc gat ttc tac tac ctg ggg ggg ttc ttc ggg ggg tcg<br>Lys Asp Glu Gly Asp Phe Tyr Tyr Leu Gly Gly Phe Phe Gly Gly Ser<br>260 265 270 | 816 | |
| gtg caa gag gtg cag cgg ctc acc agg gcc tgc cac cag gcc atg atg<br>Val Gln Glu Val Gln Arg Leu Thr Arg Ala Cys His Gln Ala Met Met<br>275 280 285 | 864 | |
| gtc gac cag gcc aac ggc atc gag gcc gtg tgg cac gac gag agc cac<br>Val Asp Gln Ala Asn Gly Ile Glu Ala Val Trp His Asp Glu Ser His<br>290 295 300 | 912 | |
| ctg aac aag tac ctg ctg cgc cac aaa ccc acc aag gtg ctc tcc ccc<br>Leu Asn Lys Tyr Leu Leu Arg His Lys Pro Thr Lys Val Leu Ser Pro<br>305 310 315 320 | 960 | |
| gag tac ttg tgg gac cag cag ctg ctg ggc tgg ccc gcc gtc ctg agg<br>Glu Tyr Leu Trp Asp Gln Gln Leu Leu Gly Trp Pro Ala Val Leu Arg<br>325 330 335 | 1008 | |

```
aag ctg agg ttc act gcg gtg ccc aag aac cac cag gcg gtc cgg aac      1056
Lys Leu Arg Phe Thr Ala Val Pro Lys Asn His Gln Ala Val Arg Asn
        340                 345                 350 ccg tga                                                              1062
Pro
```

<210> SEQ ID NO 12
<211> LENGTH: 353
<212> TYPE: PRT
<213> ORGANISM: Homo sapiens

<400> SEQUENCE: 12

```
Met Ala Glu Val Leu Arg Thr Leu Ala Gly Lys Pro Lys Cys His Ala
1               5                   10                  15

Leu Arg Pro Met Ile Leu Phe Leu Ile Met Leu Val Leu Val Leu Phe
                20                  25                  30

Gly Tyr Gly Val Leu Ser Pro Arg Ser Leu Met Pro Gly Ser Leu Glu
            35                  40                  45

Arg Gly Phe Cys Met Ala Val Arg Glu Pro Asp His Leu Gln Arg Val
        50                  55                  60

Ser Leu Pro Arg Met Val Tyr Pro Gln Pro Lys Val Leu Thr Pro Trp
65                  70                  75                  80

Lys Asp Val Leu Val Val Thr Pro Trp Leu Ala Pro Ile Val Trp Glu
                85                  90                  95

Gly Thr Phe Asn Ile Asp Ile Leu Asn Glu Gln Phe Arg Leu Gln Asn
            100                 105                 110

Thr Thr Ile Gly Leu Thr Val Phe Ala Ile Lys Lys Tyr Val Ala Phe
        115                 120                 125

Leu Lys Leu Phe Leu Glu Thr Ala Glu Lys His Phe Met Val Gly His
    130                 135                 140

Arg Val His Tyr Tyr Val Phe Thr Asp Gln Leu Ala Ala Val Pro Arg
145                 150                 155                 160

Val Thr Leu Gly Thr Gly Arg Gln Leu Ser Val Leu Glu Val Arg Ala
                165                 170                 175

Tyr Lys Arg Trp Gln Asp Val Ser Met Arg Arg Met Glu Met Ile Ser
            180                 185                 190

Asp Phe Cys Glu Arg Arg Phe Leu Ser Glu Val Asp Tyr Leu Val Cys
        195                 200                 205

Val Asp Val Asp Met Glu Phe Arg Asp His Val Gly Val Glu Ile Leu
    210                 215                 220

Thr Pro Leu Phe Gly Thr Leu His Pro Gly Phe Tyr Gly Ser Ser Arg
225                 230                 235                 240

Glu Ala Phe Thr Tyr Glu Arg Arg Pro Gln Ser Gln Ala Tyr Ile Pro
                245                 250                 255

Lys Asp Glu Gly Asp Phe Tyr Tyr Leu Gly Gly Phe Phe Gly Gly Ser
            260                 265                 270

Val Gln Glu Val Gln Arg Leu Thr Arg Ala Cys His Gln Ala Met Met
        275                 280                 285

Val Asp Gln Ala Asn Gly Ile Glu Ala Val Trp His Asp Glu Ser His
    290                 295                 300

Leu Asn Lys Tyr Leu Leu Arg His Lys Pro Thr Lys Val Leu Ser Pro
305                 310                 315                 320

Glu Tyr Leu Trp Asp Gln Gln Leu Leu Gly Trp Pro Ala Val Leu Arg
                325                 330                 335

Lys Leu Arg Phe Thr Ala Val Pro Lys Asn His Gln Ala Val Arg Asn
```

340             345             350
Pro

<210> SEQ ID NO 13
<211> LENGTH: 1065
<212> TYPE: DNA
<213> ORGANISM: Homo sapiens
<220> FEATURE:
<221> NAME/KEY: CDS
<222> LOCATION: (1)..(1065)
<223> OTHER INFORMATION:

<400> SEQUENCE: 13

```
atg gcc gag gtg ttg cgg acg ctg gcc gga aaa cca aaa tgc cac gca      48
Met Ala Glu Val Leu Arg Thr Leu Ala Gly Lys Pro Lys Cys His Ala
1               5                   10                  15 ctt cga cct atg atc ctt ttc cta ata atg ctt gtc ttg gtc ttg ttt      96
Leu Arg Pro Met Ile Leu Phe Leu Ile Met Leu Val Leu Val Leu Phe
                20                  25                  30 ggt tac ggg gtc cta agc ccc aga agt cta atg cca gga agc ctg gaa     144
Gly Tyr Gly Val Leu Ser Pro Arg Ser Leu Met Pro Gly Ser Leu Glu
            35                  40                  45 cgg ggg ttc tgc atg gct gtt agg gaa cct gac cat ctg cag cgc gtc     192
Arg Gly Phe Cys Met Ala Val Arg Glu Pro Asp His Leu Gln Arg Val
        50                  55                  60 tcg ttg cca agg atg gtc tac ccc cag cca aag gtg ctg aca ccg tgt     240
Ser Leu Pro Arg Met Val Tyr Pro Gln Pro Lys Val Leu Thr Pro Cys
65                  70                  75                  80 agg aag gat gtc ctc gtg gtg acc cct tgg ctg gct ccc att gtc tgg     288
Arg Lys Asp Val Leu Val Val Thr Pro Trp Leu Ala Pro Ile Val Trp
                85                  90                  95 gag ggc acg ttc aac atc gac atc ctc aac gag cag ttc agg ctc cag     336
Glu Gly Thr Phe Asn Ile Asp Ile Leu Asn Glu Gln Phe Arg Leu Gln
                100                 105                 110 aac acc acc att ggg tta act gtg ttt gcc atc aag aaa tac gtg gct     384
Asn Thr Thr Ile Gly Leu Thr Val Phe Ala Ile Lys Lys Tyr Val Ala
            115                 120                 125 ttc ctg aag ctg ttc ctg gag acg gcg gag aag cac ttc atg gtg ggc     432
Phe Leu Lys Leu Phe Leu Glu Thr Ala Glu Lys His Phe Met Val Gly
        130                 135                 140 cac cgt gtc cac tac tat gtc ttc acc gac cag ccg gcc gcg gtg ccc     480
His Arg Val His Tyr Tyr Val Phe Thr Asp Gln Pro Ala Ala Val Pro
145                 150                 155                 160 cgc gtg acg ctg ggg acc ggt cgg cag ctg tca gtg ctg gag gtg ggc     528
Arg Val Thr Leu Gly Thr Gly Arg Gln Leu Ser Val Leu Glu Val Gly
                165                 170                 175 gcc tac aag cgc tgg cag gac gtg tcc atg cgc cgc atg gag atg atc     576
Ala Tyr Lys Arg Trp Gln Asp Val Ser Met Arg Arg Met Glu Met Ile
                180                 185                 190 agt gac ttc tgc gag cgg cgc ttc ctc agc gag gtg gat tac ctg gtg     624
Ser Asp Phe Cys Glu Arg Arg Phe Leu Ser Glu Val Asp Tyr Leu Val
            195                 200                 205 tgc gtg gac gtg gac atg gag ttc cgc gac cat gtg ggc gtg gag atc     672
Cys Val Asp Val Asp Met Glu Phe Arg Asp His Val Gly Val Glu Ile
        210                 215                 220 ctg act ccg ctg ttc ggc acc ctg cac ccc agc ttc tac gga agc agc     720
Leu Thr Pro Leu Phe Gly Thr Leu His Pro Ser Phe Tyr Gly Ser Ser
225                 230                 235                 240 cgg gag gcc ttc acc tac gag cgc cgg ccc cag tcc cag gcc tac atc     768
Arg Glu Ala Phe Thr Tyr Glu Arg Arg Pro Gln Ser Gln Ala Tyr Ile
                245                 250                 255
```

```
ccc aag gac gag ggc gat ttc tac tac atg ggg gcg ttc ttc ggg ggg      816
Pro Lys Asp Glu Gly Asp Phe Tyr Tyr Met Gly Ala Phe Phe Gly Gly
            260                 265                 270 tcg gtg caa gag gtg cag cgg ctc acc agg gcc tgc cac cag gcc atg      864
Ser Val Gln Glu Val Gln Arg Leu Thr Arg Ala Cys His Gln Ala Met
        275                 280                 285 atg gtc gac cag gcc aac ggc atc gag gcc gtg tgg cac gac gag agc      912
Met Val Asp Gln Ala Asn Gly Ile Glu Ala Val Trp His Asp Glu Ser
    290                 295                 300 cac ctg aac aag tac cta ctg cgc cac aaa ccc acc aag gtg ctc tcc      960
His Leu Asn Lys Tyr Leu Leu Arg His Lys Pro Thr Lys Val Leu Ser
305                 310                 315                 320 ccc gag tac ttg tgg gac cag cag ctg ctg ggc tgg ccc gcc gtc ctg     1008
Pro Glu Tyr Leu Trp Asp Gln Gln Leu Leu Gly Trp Pro Ala Val Leu
                325                 330                 335 agg aag ctg agg ttc act gcg gtg ccc aag aac cac cag gcg gtc cgg     1056
Arg Lys Leu Arg Phe Thr Ala Val Pro Lys Asn His Gln Ala Val Arg
            340                 345                 350 aac ccg tga                                                         1065
Asn Pro <210> SEQ ID NO 14
<211> LENGTH: 354
<212> TYPE: PRT
<213> ORGANISM: Homo sapiens

<400> SEQUENCE: 14

Met Ala Glu Val Leu Arg Thr Leu Ala Gly Lys Pro Lys Cys His Ala
1               5                   10                  15

Leu Arg Pro Met Ile Leu Phe Leu Ile Met Leu Val Leu Val Leu Phe
            20                  25                  30

Gly Tyr Gly Val Leu Ser Pro Arg Ser Leu Met Pro Gly Ser Leu Glu
        35                  40                  45

Arg Gly Phe Cys Met Ala Val Arg Glu Pro Asp His Leu Gln Arg Val
    50                  55                  60

Ser Leu Pro Arg Met Val Tyr Pro Gln Pro Lys Val Leu Thr Pro Cys
65                  70                  75                  80

Arg Lys Asp Val Leu Val Val Thr Pro Trp Leu Ala Pro Ile Val Trp
                85                  90                  95

Glu Gly Thr Phe Asn Ile Asp Ile Leu Asn Glu Gln Phe Arg Leu Gln
            100                 105                 110

Asn Thr Thr Ile Gly Leu Thr Val Phe Ala Ile Lys Lys Tyr Val Ala
        115                 120                 125

Phe Leu Lys Leu Phe Leu Glu Thr Ala Glu Lys His Phe Met Val Gly
    130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Gly
                165                 170                 175

Ala Tyr Lys Arg Trp Gln Asp Val Ser Met Arg Arg Met Glu Met Ile
            180                 185                 190

Ser Asp Phe Cys Glu Arg Arg Phe Leu Ser Glu Val Asp Tyr Leu Val
        195                 200                 205

Cys Val Asp Val Asp Met Glu Phe Arg Asp His Val Gly Val Glu Ile
    210                 215                 220

Leu Thr Pro Leu Phe Gly Thr Leu His Pro Ser Phe Tyr Gly Ser Ser
```

```
            225                 230                 235                 240
Arg Glu Ala Phe Thr Tyr Glu Arg Arg Pro Gln Ser Gln Ala Tyr Ile
                245                 250                 255

Pro Lys Asp Glu Gly Asp Phe Tyr Tyr Met Gly Ala Phe Phe Gly Gly
            260                 265                 270

Ser Val Gln Glu Val Gln Arg Leu Thr Arg Ala Cys His Gln Ala Met
        275                 280                 285

Met Val Asp Gln Ala Asn Gly Ile Glu Ala Val Trp His Asp Glu Ser
    290                 295                 300

His Leu Asn Lys Tyr Leu Leu Arg His Lys Pro Thr Lys Val Leu Ser
305                 310                 315                 320

Pro Glu Tyr Leu Trp Asp Gln Gln Leu Leu Gly Trp Pro Ala Val Leu
                325                 330                 335

Arg Lys Leu Arg Phe Thr Ala Val Pro Lys Asn His Gln Ala Val Arg
            340                 345                 350

Asn Pro

<210> SEQ ID NO 15
<211> LENGTH: 19
<212> TYPE: DNA
<213> ORGANISM: Artificial Sequence
<220> FEATURE:
<223> OTHER INFORMATION: probes and primers

<400> SEQUENCE: 15
gggaggaagc gaaggtgca                                             19

<210> SEQ ID NO 16
<211> LENGTH: 22
<212> TYPE: DNA
<213> ORGANISM: Artificial Sequence
<220> FEATURE:
<223> OTHER INFORMATION: probes and primers

<400> SEQUENCE: 16
cttgatgggt ttatccagaa ca                                         22

<210> SEQ ID NO 17
<211> LENGTH: 20
<212> TYPE: DNA
<213> ORGANISM: Artificial Sequence
<220> FEATURE:
<223> OTHER INFORMATION: probes and primers

<400> SEQUENCE: 17
tgataatccc agcagtattc                                            20

<210> SEQ ID NO 18
<211> LENGTH: 36
<212> TYPE: DNA
<213> ORGANISM: Artificial Sequence
<220> FEATURE:
<223> OTHER INFORMATION: probes and primers

<400> SEQUENCE: 18
acgtggctcc aagaattctc caggcaagag tactgg                          36

<210> SEQ ID NO 19
<211> LENGTH: 49
<212> TYPE: DNA
<213> ORGANISM: Artificial Sequence
<220> FEATURE:
```

-continued

<223> OTHER INFORMATION: probes and primers

<400> SEQUENCE: 19
catcttgttc aatggccgat cccattattt tctcctggga aaagaaaag                49

<210> SEQ ID NO 20
<211> LENGTH: 49
<212> TYPE: DNA
<213> ORGANISM: Artificial Sequence
<220> FEATURE:
<223> OTHER INFORMATION: probes and primers

<400> SEQUENCE: 20
cttttctttt cccaggagaa ataatggga tcggccattg aacaagatg                49

<210> SEQ ID NO 21
<211> LENGTH: 23
<212> TYPE: DNA
<213> ORGANISM: Artificial Sequence
<220> FEATURE:
<223> OTHER INFORMATION: probes and primers

<400> SEQUENCE: 21
caggtcgacg gatccgaaca aac                                            23

<210> SEQ ID NO 22
<211> LENGTH: 47
<212> TYPE: DNA
<213> ORGANISM: Artificial Sequence
<220> FEATURE:
<223> OTHER INFORMATION: probes and primers

<400> SEQUENCE: 22
cagatctaac gaggattcaa tgtcaaagga aaagtgattc tgtcaat                  47

<210> SEQ ID NO 23
<211> LENGTH: 27
<212> TYPE: DNA
<213> ORGANISM: Artificial Sequence
<220> FEATURE:
<223> OTHER INFORMATION: probes and primers

<400> SEQUENCE: 23
ctgaactgaa tgtttatcca ggccatc                                        27

<210> SEQ ID NO 24
<211> LENGTH: 51
<212> TYPE: DNA
<213> ORGANISM: Artificial Sequence
<220> FEATURE:
<223> OTHER INFORMATION: probes and primers

<400> SEQUENCE: 24
gcgcaccgtg ggcttgtact cggtcattat tttctcctgg gaaagaaaa g              51

<210> SEQ ID NO 25
<211> LENGTH: 34
<212> TYPE: DNA
<213> ORGANISM: Artificial Sequence
<220> FEATURE:
<223> OTHER INFORMATION: probes and primers

<400> SEQUENCE: 25
gagaaaataa tgaccgagta caagcccacg gtgc                                34

```
<210> SEQ ID NO 26
<211> LENGTH: 26
<212> TYPE: DNA
<213> ORGANISM: Artificial Sequence
<220> FEATURE:
<223> OTHER INFORMATION: probes and primers

<400> SEQUENCE: 26
ctggggatcc agacatgata agatac                                          26

<210> SEQ ID NO 27
<211> LENGTH: 22
<212> TYPE: DNA
<213> ORGANISM: Artificial Sequence
<220> FEATURE:
<223> OTHER INFORMATION: probes and primers

<400> SEQUENCE: 27
cagctgtgtg ggtatgggag gg                                              22

<210> SEQ ID NO 28
<211> LENGTH: 27
<212> TYPE: DNA
<213> ORGANISM: Artificial Sequence
<220> FEATURE:
<223> OTHER INFORMATION: probes and primers

<400> SEQUENCE: 28
ctgaactgaa tgtttatcca ggccatc                                         27

<210> SEQ ID NO 29
<211> LENGTH: 22
<212> TYPE: DNA
<213> ORGANISM: Artificial Sequence
<220> FEATURE:
<223> OTHER INFORMATION: probes and primers

<400> SEQUENCE: 29
cagctgtgtg ggtatgggag gg                                              22

<210> SEQ ID NO 30
<211> LENGTH: 27
<212> TYPE: DNA
<213> ORGANISM: Artificial Sequence
<220> FEATURE:
<223> OTHER INFORMATION: probes and primers

<400> SEQUENCE: 30
agccgattgt ctgttgtgcc cagtcat                                         27

<210> SEQ ID NO 31
<211> LENGTH: 48
<212> TYPE: DNA
<213> ORGANISM: Artificial Sequence
<220> FEATURE:
<223> OTHER INFORMATION: probes and primers

<400> SEQUENCE: 31
ctgacgatgg ctccggagcc acattatttt ctcctgggaa aagaaaag                  48

<210> SEQ ID NO 32
<211> LENGTH: 26
<212> TYPE: DNA
<213> ORGANISM: Artificial Sequence
<220> FEATURE:
<223> OTHER INFORMATION: probes and primers
```

```
<400> SEQUENCE: 32
ataatgtggc tccggagcca tcgtca                                            26

<210> SEQ ID NO 33
<211> LENGTH: 34
<212> TYPE: DNA
<213> ORGANISM: Artificial Sequence
<220> FEATURE:
<223> OTHER INFORMATION: probes and primers

<400> SEQUENCE: 33
aaaggatcct caaggcttag ccaatgtcca gagt                                   34

<210> SEQ ID NO 34
<211> LENGTH: 75
<212> TYPE: DNA
<213> ORGANISM: Artificial Sequence
<220> FEATURE:
<223> OTHER INFORMATION: probes and primers

<400> SEQUENCE: 34
gatccgggga tcggcaataa aaagacagaa taaaacgcac gggtgttggg tcgtttgttc       60
ctcgaggtcg acgat                                                        75

<210> SEQ ID NO 35
<211> LENGTH: 71
<212> TYPE: DNA
<213> ORGANISM: Artificial Sequence
<220> FEATURE:
<223> OTHER INFORMATION: probes and primers

<400> SEQUENCE: 35
atcgtcgacc tcgaggaaca aacgacccaa cacccgtgcg ttttattctg tcttttttatt     60 gccgatcccc g                                                            71

<210> SEQ ID NO 36
<211> LENGTH: 26
<212> TYPE: DNA
<213> ORGANISM: Artificial Sequence
<220> FEATURE:
<223> OTHER INFORMATION: probes and primers

<400> SEQUENCE: 36
cctatgcaaa ttaaggtaga acgcac                                            26

<210> SEQ ID NO 37
<211> LENGTH: 48
<212> TYPE: DNA
<213> ORGANISM: Artificial Sequence
<220> FEATURE:
<223> OTHER INFORMATION: probes and primers

<400> SEQUENCE: 37
ctgacgatgg ctccggagcc acattatttt ctcctgggaa aagaaaag                    48

<210> SEQ ID NO 38
<211> LENGTH: 26
<212> TYPE: DNA
<213> ORGANISM: Artificial Sequence
<220> FEATURE:
<223> OTHER INFORMATION: probes and primers

<400> SEQUENCE: 38
ataatgtggc tccggagcca tcgtca                                            26
```

```
<210> SEQ ID NO 39
<211> LENGTH: 29
<212> TYPE: DNA
<213> ORGANISM: Artificial Sequence
<220> FEATURE:
<223> OTHER INFORMATION: probes and primers

<400> SEQUENCE: 39
ctcgaggaac aaacgaccca acacccgtg                                              29

<210> SEQ ID NO 40
<211> LENGTH: 23
<212> TYPE: DNA
<213> ORGANISM: Artificial Sequence
<220> FEATURE:
<223> OTHER INFORMATION: probes and primers

<400> SEQUENCE: 40
tgacgatggc tccggagcca cat                                                    23
```

ANIMAL TISSUE WITH CARBOHYDRATE ANTIGENS COMPATIBLE FOR HUMAN TRANSPLANTATION

RELATED APPLICATIONS

This application claims priority benefit of U.S. provisional patent application 60/277,811, filed Mar. 21, 2001, pending. The priority application is hereby incorporated herein by reference in its entirety, as are U.S. Ser. No. 60/277,749 and issued U.S. Pat. Nos. 6,147,276, 6,252,133, and 6,261,836.

TECHNICAL FIELD

This invention relates generally to the fields of carbohydrate chemistry and animals engineered with a genetic knockout. It describes non-human mammals in which the enzyme α(1,3) galactosyl-transferase has been replaced with α(1,2)fucosyltransferase.

BACKGROUND

The acute shortage of human organs for transplantation provides a compelling need for the development of new sources of suitable tissue. An idea of considerable promise is to transplant patents with organs from non-human animals. The main challenge to overcome is rendering foreign tissue immunologically compatible with the patient being treated.

Tissue from most mammalian species would undergo hyperacute rejection when transplanted into humans. This is because human plasma contains natural antibodies against carbohydrate determinants of the animal tissue, thought to originate through prior immune stimulation by dietary antigen or mucosal microflora. Since the antibodies are preformed, rejection occurs within days of the transplant.

The main target for the natural antibodies mediating rejection is cell-surface oligosaccharides expressing the determinant Galα(1,3)Gal (reviewed by Joziasse et al., Biochim. Biophys. Acta 1455:403, 1999). Humans, apes and Old World monkeys differ from other mammals in that they lack α-galactosyl epitopes in complex oligosaccharides. Other mammals express the Galα(1,3)Gal epitope prominently on the surface of nucleated cells, including hepatic cells, renal cells, and vascular endothelium—which is especially problematic for xenotransplantation of whole organs.

The Galα(1,3)Gal epitope is made by a specific enzyme, α(1,3) galactosyltransferase, abbreviated in this disclosure as α1,3GT. The transferase uses UDP-galactose as a source of galactose, which it transfers specifically to an acceptor oligosaccharide, usually Galβ(1,4)GlcNAc (N-acetyl lactosamine). In mammals that don't express the Galα(1,3)Gal product, the α1,3GT locus is inactivated (Gailili et al., Proc. Natl. Acad. Sci. USA 15:7401, 1991). There are frameshift and nonsense mutations within the locus, turning it into a non-functional, processed pseudogene (Laarsen et al., J. Biol. Chem. 265:7055, 1990; Joziasse et al., J. Biol. Chem. 266:6991, 1991).

In humans, N-acetyl lactosamine acceptor oligosaccharides are processed differently. The enzyme α(1,2)fucosyltransferase builds the N-acetyl lactosamine into Fucα(1,2)Galβ(1,4)GlcNAc, which is blood group H substance. This in turn serves as an acceptor substance for blood group A GlcNAc-transferase, or blood group B Gal-transferase, forming A-substance or B-substance, respectively, depending on the blood type of the individual. Naturally occurring antibodies circulating in the blood are reactive against the alternative carbohydrate determinants that are not self-antigens.

Larsen et al. (Proc. Nat. Acad. Sci. USA 86:8227, 1989) isolated and characterized a cDNA encoding murine α1,3GT. Joziasse et al. (J. Biol. Chem. 267:5534, 1992) detected four distinct mRNA transcripts, which predict four different isoforms of the α1,3GT. The full-length mouse mRNA (including 5' untranslated mRNA) was reported to span at least 35-kb of genomic DNA, distributed over nine exons ranging from 36 base pairs to ~2600 base pairs in length. Numbering in the 5' to 3' direction, the coding region is distributed over Exons 4 to 9. The four transcripts are formed by alternative splicing of the pre-mRNA.

Joziasse et al. (J. Biol. Chem. 264:14290, 1989) isolated and characterized a cDNA encoding bovine cDNA. The coding sequence was predicted to be a membrane-bound protein with a large glycosylated COOH-terminal domain, a transmembrane domain, and a short $NH_2$ terminal domain.

The porcine α1,3GT cDNA sequence has been reported from several different laboratories: Strahan et al. (Immunogenetics 41:101, 1995); U.S. Pat. Nos. 5,821,117; 5,849,991; and International Patent Application WO 95/28412. The genomic organization of porcine α1,3GT was reported by Katayama et al. (Glycoconjugate J. 15:83, 1998). Again, the coding region spans six exons, conserving the arrangement present in the mouse genome, and extending over nearly 24-kb.

It has been reported that about 95% of the naturally occurring xenospecific antibody in humans recognize the Galα(1,3)Gal epitope (McKensie et al., Transpl. Immunol. 2:81, 1994). Antibody in human serum binds specifically to pig endothelial cells in a manner that is inhibitable by Galα(1,3)Gal, or by Galα(1, 6)Glc (melibiose). New age monkeys have the same naturally occurring antibody, and demonstrate hyperacute rejection of pig organ xenotransplants. The rejection reaction can be obviated in experimental animals by infusing the recipient with the free carbohydrate (Ye et al., Transplantation 58:330, 1994), or by adsorbing antibody from the circulation on a column of Galα(1,3)Gal or melibiose (Cooper et al., Xenotransplantation 3:102, 1996).

It has been suggested that xenotransplants of pig tissue could provide a source of various tissue components—heart valves, pancreatic islet cells, and perhaps large organs such as livers and kidneys (Cowley, Newsweek, Jan. 1, 2000). If xenotransplants from non-primates into humans is ever to become viable, then techniques need to be developed to prevent Galα(1,3)Gal mediated rejection. Possible genetic manipulation strategies are reviewed by Gustafsson et al. (Immunol. Rev. 141:59, 1994), Sandrin et al. (Frontiers Biosci. 2:e1–11, 1997), and Lavitrano et al. (Forum Genova 9:74, 1999).

One approach is to prevent the formation of Galα(1,3)Gal by providing another transferase that competes with α1,3GT for the N-acetyl lactosamine acceptor. International Patent Application WO 97/12035 (Nextran-Baxter) relates to transgenic animals that express at least one enzyme that masks or reduces the level of the xenoreactive antigens by competing with α1,3GT. The enzymes proposed are α(1,2)fucosyltransferase (that makes H antigen in humans), α(2,6)sialyltransferase, and β(1,3)N-acetylglucosaminyltransferase. It is thought that once N-acetyl lactosamine has been converted by one of these transferases, it can no longer act as an acceptor for α1,3GT. The xenotransplantation cells of Application WO 97/12035 have at least one enzyme that reduces Galα(1,3)Gal expression, and also express a complement inhibitor such as CD59, decay accelerating factor (DAF), or membrane cofactor protein (MCP). Expression of human CD59 in transgenic pig organs enhances organ survival in an ex vivo xenogeneic perfusion model (Kroshus et al., Transplantation 61:1513, 1996).

Another approach is to disassemble Galα(1,3)Gal after it is formed. International Patent Application WO 95/33828 (Diacrin) suggests modifying cells for xenogeneic transplants by treating tissue with an α-glycosidase. Osman et al. (Proc. Natl. Acad. Sci. USA 23:4677, 1997) reported that combined transgenic expression of both α-glycosidase and α(1,2)fucosyltransferase leads to optimal reduction in Galα(1,3)Gal epitope. Splenocytes from mice overexpressing human α-glycosidase showed only a 15–25% reduction in binding of natural human anti-Galα(1,3)Gal antibodies. Mice expressing human α(1,2)fucosyltransferase as a transgene showed a reduction of Galα(1,3)Gal epitopes by ~90%. Doubly transfected COS cells expressing both the glycosidase and the transferase showed negligible cell surface staining with anti-Galα(1,3)Gal, and were not susceptible to lysis by human serum containing antibody and complement.

A further alternative is to prevent Galα(1,3)Gal expression in the first place. Strahan et al. (Xenotransplantation 2:143, 1995) reported the use of antisense oligonucleotides for inhibiting pig α1,3GT, leading to a partial reduction in expression of the major target for human natural antibodies on pig vascular endothelial cells. Hayashi et al. (Transplant Proc. 29:2213, 1997) reported adenovirus-mediated gene transfer of antisense ribozyme for α1,3GT and α(1,2) fucosyltransferase genes in xenotransplantation.

U.S. Pat. No. 5,849,991 (Bresatch) describes DNA constructs based on the mouse α1,3GT sequence. They are designed to disrupt expression of functional α1,3GT by undergoing homologous recombination across Exon 4, 7, 8, or 9. The constructs contain a selectable marker such as $neo^R$, $hyg^R$ or thymidine kinase. It is proposed that such constructs be introduced into mouse embryonic stem (ES) cells, and recovering cells in which at least one α1,3GT gene is inactivated. Experiments are reported which produced mice that are homozygous for inactivated α1,3GT, resulting in lack of expression of Galα(1,3)Gal epitope, as determined by specific antibody.

U.S. Pat. No. 5,821,117 (Austin Research Inst.) report cDNA sequence data for porcine α1,3GT. This was used to probe a pig genomic DNA library, and two lambda phage clones were obtained that contain different regions of the porcine transferase gene. International Patent Application WO 95/28412 (Biotransplant) also reports cDNA sequence data for porcine α1,3GT. It is proposed that genomic DNA fragments be isolated from an isogenic DNA library, and used to develop a gene-targeting cassette including a positive or negative selectable marker.

International Patent Application WO 99/21415 (Stem Cell Sciences, Biotransplant) reports construction of a DNA library from miniature swine. A vector is obtained comprising a pgk-neo cassette, and fragments of the α1,3GT gene. This is used for homologous recombination to eliminate α1,3GT activity in porcine embryonic fibroblasts. Costa et al., Alexion Pharmaceuticals (Xenotransplantion 6:6, 1999) report experiments with transgenic mice expressing the human complement inhibitor CD59. In α1,3GT knockout mice, the CD59 gene helped prevent human serum-mediated cytolysis. It had a similar effect in mice expressing α(1,2) fucosyltransferase. Combination of all three modifications provided no additional protective effect.

There have been no reports of the use of α1,3GT inactivated tissue suitable for xenotransplantation into humans. In view of the paucity of available organs for human transplantation, there is a pressing need to develop further options.

SUMMARY

This disclosure provides technology for generating animal tissue with carbohydrate antigens that are compatible for transplantation into human patients. The tissue is inactivated homozygously for expression of α(1,3)galactosyltransferase, and comprises a transgene for α(1,2)fucosyltransferase. As a result, cell-surface N-acetyl lactosamine is not converted to the Galα(1,3)Gal antigen—but converted to Fucα(1,2)Gal, which is H substance, a self-antigen in humans.

One embodiment of this invention is a mammalian cell that is homozygous for inactivation of the α1,3GT gene (which means that the α1,3GT enzyme is not produced from either allele, whether or not the manner of inactivation is the same on both alleles). The cell also expresses an α1,2FT transgene, either by integration at a random site, or by replacing at least part of the encoding sequence in the α1,3GT gene with an α1,2FT encoding sequence (this means that the α1,3GT encoding sequence or a portion of it is no longer expressed, whether or not it is still present in the genome). In some cases, the α1,2FT encoding sequence is placed under control of the endogenous α1,3GT promoter.

In a related embodiment, the cells of this invention are adapted to express glycosyl transferase enzymes capable of synthesizing either the A determinant, the B determinant, or both, of the human ABO blood group.

Another embodiment of this invention is tissue from a mammal that has been genetically modified to be devoid of antibody-detectable Galα(1,3)Gal determinants that it would otherwise express. The tissue also expresses at least one ABO blood group substance, such as H substance, A substance, B substance, or any combination thereof, and may express other antigens such as Secretor substance or CD59. Another embodiment of this invention is tissue from a mammal that has been genetically modified to expresses α1,2FT de novo, and to suppress expression of endogenous α1,3GT.

A further embodiment of this invention is a non-human mammal that is homozygous for inactivation of the α1,3GT gene. The mammal also expresses an α1,2FT transgene, either randomly integrated into the genome, or replacing at least part of the encoding sequence in the α1,3GT gene. In a related embodiment, the mammal is transgenic for the ABO blood group A-transferase, B-transferase, or both. The genetically modified cells, tissues and animals of this invention can be from any vertebrate or mammalian species, of which sheep and pigs are exemplary.

Another embodiment of the invention is a process for making genetically modified cells by nuclear transfer. At least one allele of the α1,3GT gene in a donor cell is inactivated or replaced by any effective mechanism, as described later in this disclosure. The donor cell comprises an α1,2FT transgene, and optionally has increased telomerase activity to facilitate multiple targeting events or other genetic manipulations in a single generation. Following genetic manipulation, the nucleus of the donor cell is transferred to a recipient cell. Certain cells produced by this method can be used to create an embryo, which can be engrafted the cell into the uterus of a surrogate host to produce a birthed animal. Tissue of this invention can be harvested from the embryo, the birthed animal, or its progeny.

This invention also provides a system for selecting a cell that has undergone genetic alteration by homologous recombination from amongst a population of cells that do not have the alteration. The successfully targeted cell is identified and separated according to surface glycosylation that has changed as a result of the homologous recombination. The recombination event may inactivate an endogenous gene, or introduce a transgene, either of which may be a carbohydrate modulating enzyme, such as a glycosyltransferase or specific glycosidase in any combination. Altering carbohydrate modulating enzymes can be done for its own sake, or as a means for tracking inactivation of other endogenous genes or insertion of other genetic elements. Exemplary reagents and separation methods for use in this system are provided later in the disclosure. This cell selection system has important advantages for producing genetically altered cell types for a variety of purposes.

These and other embodiments of the invention will be apparent from the description that follows.

DRAWINGS

FIG. 1 is a map showing location of introns in the sheep α1,3GT gene. Designs are shown for targeting vectors that inactivate the sheep α1,3GT gene by homologous recombination. Each targeting vector comprises a selectable marker (neo), flanked on one side by an intron sequence of 1–2-kb, and on the other side by an intron sequence of 7–10-kb. A number of vectors have been obtained that target Exon 4, Exon 8, or Exon 9.

FIG. 2 is a set of drawings that compare the details of the targeting vectors p0054, p0079, and p0063, respectively, alongside the α1,3GT gene. These vectors are designed to replace the coding region in Exon 4 (which contain the translation start site) with the selectable marker neo or pac.

FIG. 3 is a photocopy of a gel showing PCR analysis of sheep fetal fibroblasts targeted with the p0054 vector. Using two primers for intron sequences that flank Exon 4 (upper panel), the expected product is 2.8-kb for native α1,3GT, and 2.2-kb after homologous recombination. Using a primer for the selectable marker (lower panel), amplification product is expected only after recombination. The results show that one of the samples is from a fibroblast that has successfully been targeted—replacing Exon 4 with the selectable marker. Since Exon 4 contains the translation initiation site, this would inactivate the α1,3GT gene.

Figure 6:
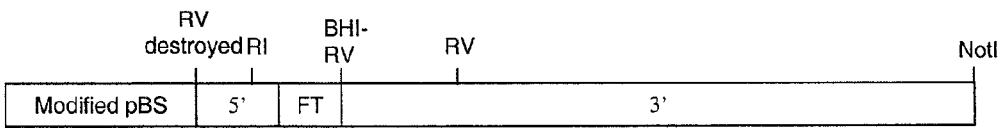
Figure 6:
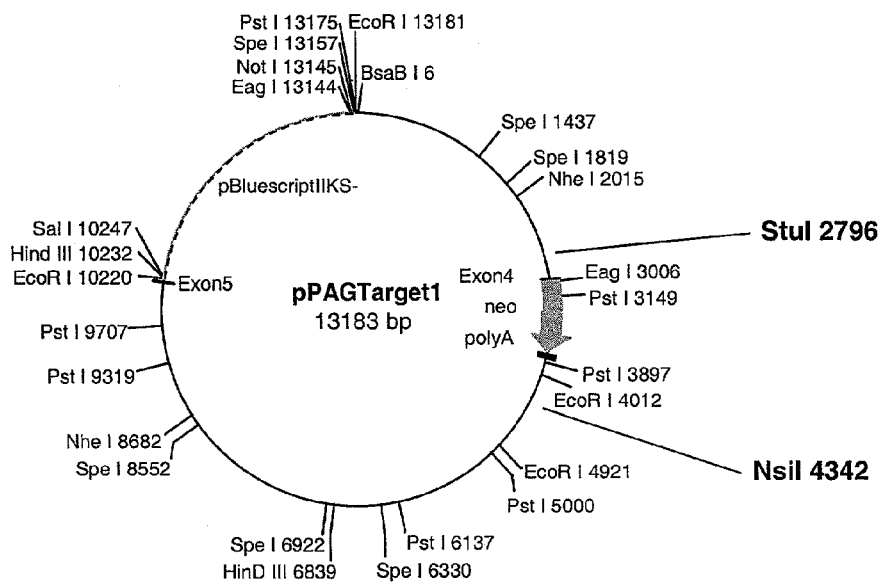
Figure 6:
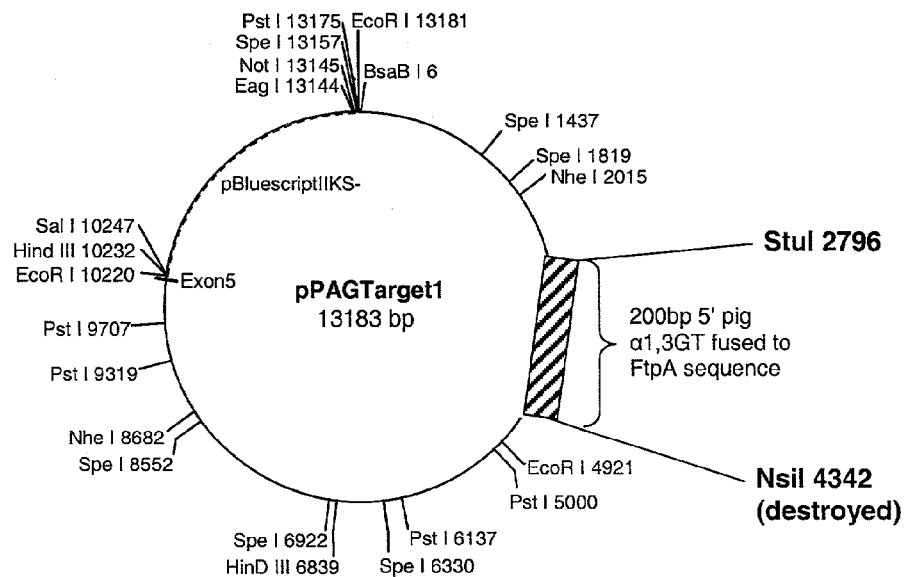

FIG. 6 is a family of maps showing targeting vectors that replace part of the α1,3GT encoding region with the full-length α1,2FT sequence. The uppermost map is a modification of the p0054 vector for inactivating the sheep α1,3GT. The human α1,2FT sequence is flanked by sequence of the α1,3GT gene that flanks the targeted region in Exon 4. The map in the center is a targeting vector for inactivating the pig α1,3GT gene, replacing the beginning of the encoding region with the drug resistance marker neo. The map at the bottom is an adaptation of the pig vector, with the human α1,2FT encoding sequence between the flanking α1,3GT sequences. Sheep or pig tissue having the α1,3GT inactivated on both alleles and replaced on at least one allele with α1,2FT will not form the Galα(1,3)Gal xenogeneic antigen. In its place, they form Fucα(1,2)Gal, which is H substance, a self-antigen in humans.

Figure 7:
Figure 7:
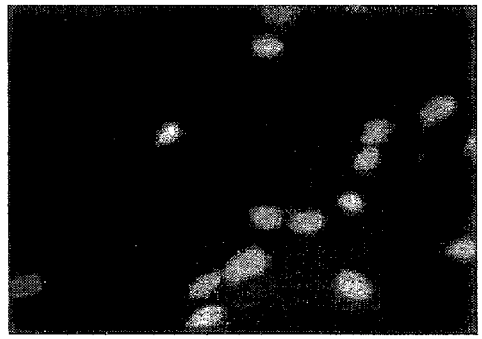
Figure 7:
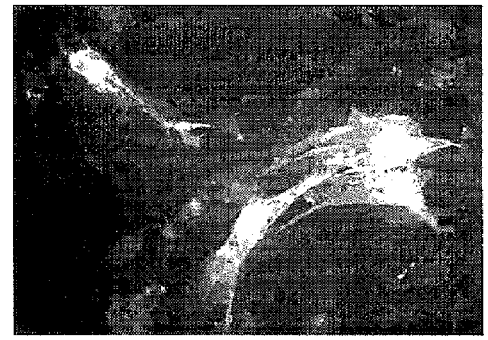
Figure 7:
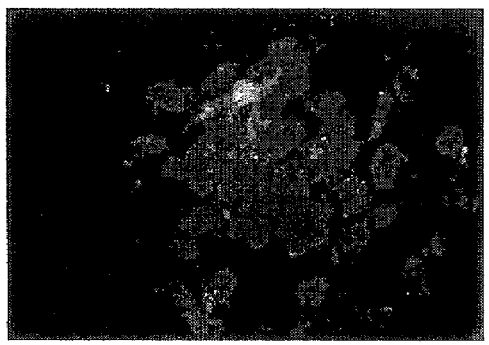
Figure 7:
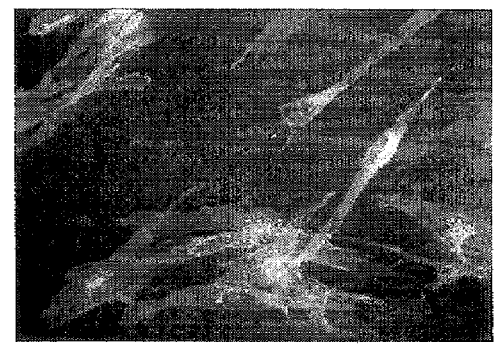

FIG. 7 is a reproduction of fluorescence micrographs, showing that expression of the human α1,2FT gene in sheep fibroblasts does indeed cause cell-surface expression of H substance carbohydrate. DAPI and Ulex Europaeus (UEA) lectin staining of human 293 cells (a positive control) is compared with telomerized sheep cells of the B9 and C9 line—both of which have been lipofected with a vector containing the human α1,2FT gene. As a result of transfection, the sheep cell lines now bind the UEA lectin, showing that the α1,2FT has synthesized H substance.

DETAILED DESCRIPTION

The cell-surface carbohydrate antigen Galα(1,3)Gal is the linchpin for hyperacute rejection of tissue xenografts from animals into humans. For this reason, considerable effort has been made to obtain animal tissue lacking α(1,3)galactosyltransferase (α1,3GT), which is responsible for the synthesis of this determinant.

It is a hypothesis of this invention that simply inactivating α1,3GT expression may be suboptimal for tissue used in xenotransplantation.

There are two reasons. First, the acceptor substance for the α1,3GT enzyme is Galβ(1,4)GlcNAc (N-acetyl lactosamine). In the absence of α1,3GT, the galactose residue is presented at the terminus of the oligosaccharide branch, making it available for galectins of a corresponding specificity. The galectins constitute a family of animal lectins that have been implicated in cell adhesion and migration, tumor cell recognition, augmentation of immune defense, cytokine production, cytotoxicity, and apoptosis (H.-J. Gabius, Eur. J. Biochem 243:543, 1997; G. A. Rabinovitch, Cell Death Differ. :711, 1999). Galectin-1 and galectin-3 are expressed pathologically in colon cancer, melanoma, fibrosarcoma, lymphoma, leukemia, HTLV-1 infected T cells, and a variety of carcinomas (Perillo et al., J. Mol Med. 76:402, 1998). It is hypothesized that a graft with unusual density of terminal galactose residues may act as a magnet for inflammatory cells, or for tumor metastases.

The second reason is that N-acetyl lactosamine is itself an epitope against which humans have naturally occurring antibodies. The antibodies of this specificity are not generally a problem, because they are cold agglutinins not reactive at body temperature. However, their presence indicates that the human immune system is immunologically primed. Display of N-acetyl lactosamine in the context of other foreign antigens on pig tissue may be sufficiently immunogenic to generate antibodies against the epitope that would mediate delayed rejection.

This invention provides a better alternative: replacing α1,3GT activity with α(1,2)fucosyltransferase (α1,2FT) activity. The transplant tissue is homozygously α1,3GT inactivated, and contains at least one copy of an α1,2FT encoding region. The α1,3GT product Galα(1,3)Gal is not synthesized. Instead, a normal proportion of the acceptor substrate is fucosylated to H-substance—rendering it inert to pathogenic activity of galectins and naturally occurring antibody in humans, since H substance is a self-antigen. The transplant tissue will have the equivalent histo blood group type O—which in terms of the ABO blood group major cross-match is the universal donor blood type.

The carbohydrate phenotype can be matched even more closely to that of the patient being treated. H substance synthesized on the tissue is in turn the precursor substance for the A and B blood group transferases. If the tissue contains an expressible copy of the gene for blood group A GlcNAc-transferase, or blood group B Gal-transferase, then it will convert a proportion of the precursor to A substance or B substance respectively. By having the appropriate glycosyltransferase enzymes present in the tissue, then animal tissue for xenotransplantation can be obtained from non-cattharine animals that have tissue type corresponding to blood group A, B, AB, and O.

This way, a xenograft can be matched exactly according to the ABO type of the patient being treated. In liver transplants, an ABO minor mismatch (such as a type O graft in a type A patient) can cause a graft-versus-host reaction, due to passenger lymphocytes in the transplanted tissue. The compositions and techniques provided in this disclosure make it possible to minimize immunological reaction either way due to mismatch of either the Galα(1,3)Gal antigen, or the ABO blood group antigens.

A series of complex genetic modifications of this nature has not previously been achieved in a large animal species. The engineering strategy provided in this description allows the skilled artisan to make all the genetic modifications required to a particular cell line as a matter of routine experimental optimization.

A particularly efficient manner of achieving α1,2FT gene replacement animals is to do the manipulations on a cell line (such as primary fetal fibroblasts) suitable for nuclear transfer and cloning into an animal. The genetic modifications and selection procedures typically involve considerable proliferation of the cells. It has been discovered that increasing telomerase activity in the cells helps preserve telomere length throughout the modifications, keeping the cells in a condition suitable for nuclear transfer. In addition, telomerizing the cell appears to increase the frequency of successfully targeted clones, and the effectiveness of nuclear transfer. It has been discovered that telomerase reverse transcriptase can be used from a different vertebrate species in order to achieve this result.

An established cell line of animal origin is first transfected with human telomerase reverse transcriptase (hTERT) to extend its replicative capacity, and provide these other beneficial effects. It is then targeted sequentially on each allele to inactivate or replace the α1,3GT gene, selecting the cells for correct targeting events. Once all genetic manipulations are complete, the nucleus of the modified cell is transferred to a suitable recipient, and an embryo is formed according to established cloning techniques. Variations and alternatives to this strategy are also effective, as described in the following sections.

Definitions

For purposes of this disclosure, the term Galα(1,3)Gal (abbreviated GAL) refers to an oligosaccharide determinant present on endothelial cells and other cells of most non-primate mammals, for which humans have a naturally occurring antibody. The usual structure is Galα(1,3)Galβ(1,4)GlcNAc, although other forms of Galα(1,3)Gal specifically detectable by the naturally occurring anti Galα(1,3)Gal in human serum of B blood type are included. Galα(1,3)Gal is distinct from the Galα(1,3)[Fucα(1,2)]-Galβ(1,4)GlcNAc determinant characteristic of the human B blood type antigen.

An "antibody detectable" determinant refers to a determinant that is present in an amount and is sufficiently accessible so that it can be detected by an antibody specific for the determinant in an appropriate immunoassay—such as an agglutination reaction, optionally developed with an antiglobulin reagent, or by immunohistochemistry.

The term "α(1,3)galactosyltransferase" and the abbreviation "α1,3GT" refer to the enzyme present in non-primate mammals that catalyzes the formation of the Galα(1,3)Gal determinant by attaching Gal in the α(1,3) position to the Galβ(1,4)GlcNAc acceptor. α1,3GT has the Enzyme Commission designation EC 2.4.1.124. α1,3GT is not naturally expressed in humans, and the term does not include the galactosyltransferase that forms the human B blood group antigen.

The term "α(1,2)fucosyltransferase" and the abbreviation "α1,2FT" refer to the enzyme present in primate mammals that catalyzes the formation of the Fucα(1,2)Gal determinant (blood group H substance, a.k.a. ABO precursor substance) by attaching fucose in the α(1,2) position to the acceptor substrate N-acetyl lactosamine. α1,2FT has the Enzyme Commission designation EC 2.4.1.69. It is also known as FUT1, to distinguish it from Secretor blood group α(1,2)fucosyltransferase (FUT2), and other fucosyltransferases.

An "acceptor" substance for α1,3GT or α1,2FT is a carbohydrate structure that can act as a substrate and become further glycosylated as a result of transferase activity. Acceptors for α1,3GT include both Galβ(1,3)GlcNAc and Galβ(1,4)GlcNAc (Basu et al., J. Biol. Chem. 248:1700, 1973; Blake et al., J. Biol. Chem. 256:5387, 1981).

A-transferase is said to be "detectably expressed" by a cell at the mRNA level when mRNA encoding the transferase can be measured in the cell by some suitable technique, such as Northern analysis or PCR-reverse transcriptase. It may also be expressed at the protein level, as detected by a specific antibody or demonstration of the characteristic enzymatic activity. Scientists skilled in the art will recognize that some cells (such as mature red blood cells) do not express any glycosyltransferases, even though they display certain oligosaccharide determinants. Inhibition of α1,3GT expression is only meaningful in cells capable of expressing other glycosyltransferase enzymes.

A gene is said to be "inactivated" when it is rendered incapable of transcribing a functional protein. For example, an inactivated gene may be missing necessary transcription or translation control elements, it may be lacking an essential part of the protein encoding region, or the encoding region may be placed out of phase. In another example, the gene may be interrupted by an inserted sequence, or mutated in such a way as to interfere with transcription or translation of the gene product. In a third example, the inactivated gene may produce a translation product that has been altered in such a way that it lacks important enzymatic activity of the native gene product. A gene is also "inactivated" when the normal encoding region is switched with an encoding region for a different gene product with a different biological function.

In the descriptions of genetic modification and inactivation in this disclosure, it is understood that changes to the genome of a cell are inherited by progeny of the cell, unless further genetic manipulation occurs. Thus, it is possible to select the modified cells, let them proliferate, and then make a subsequent modification to the progeny. A sequence of genetic modifications made to cell and its ancestors are considered equivalent to making all the modifications to the same cell, unless explicitly directed otherwise.

A cell is said to be "transfected", "genetically transformed", or "genetically altered", when the cell has been introduced with a recombinant polynucleotide, or is the progeny of such a cell. The alteration may (but need not) be integrated into the genome of the cell. Non-limiting examples include the following: 1. A cell containing a vector with a sequence encoding a protein of interest, capable of causing the protein to be expressed by the cell on a transient or inheritable fashion. 2. A cell containing a genetic construct for targeting an endogenous gene (whether or not the gene has been successfully targeted). 3. A cell containing a genetic modification introduced by recombinant means.

A cell is described as "telomerized" if it has been treated to increase the expression of telomerase reverse transcriptase (TERT) and/or functional telomerase activity by any suitable means beyond the level usually expressed by cells of the same type in the same environment. Methods for telomerizing cells are illustrated in a later section of this disclosure. The term also applies to progeny of the originally treated cell that have inherited the ability to express telomerase at an elevated level.

The terms "polynucleotide" and "oligonucleotide" are used interchangeably to refer to a polymeric form of nucleotides of any length. Included are genes and gene fragments, mRNA, cDNA, plasmids, vectors, synthetic nucleic acids, targeting constructs, nucleic acid probes, and primers.

A "control element" or "control sequence" is a nucleotide sequence involved in an interaction of molecules that contributes to the functional regulation of a polynucleotide, such as replication, duplication, transcription, splicing, or translation. Transcriptional control elements include promoters and enhancers.

The term "embryo" as it is used in this disclosure refers to an organism developing in the uterus of a species of interest at any time after fertilization or intrauterine transfer, not limited to a particular developmental period. The terms "engrafting" or "transplanting", in reference to embryo manipulation, refer to any process known in the art for artificially introducing one or more embryos into the uterus of a female animal.

The term "tissue" refers to a heterogeneous collection of cells responsible for maintaining one or more physiological functions. Of interest for certain embodiments of this invention are organs suitable for transplantation, such as a whole kidney; however, the term also includes organ fragments and other embodiments, such as a piece of connective tissue, or a collection of cells in a medical support device.

General Techniques

In general, the practice of this invention can be carried out using standard techniques of genetic engineering, protein manipulation, and cell culture. Textbooks that describe standard laboratory techniques include the current editions of "*Molecular Cloning: A Laboratory Manual*" (Sambrook et al.); "*Animal Cell Culture*" (R. I. Freshney, ed.); the series "*Methods in Enzymology*" (Academic Press, Inc.); "*Current Protocols in Molecular Biology*" (F. M. Ausubel et al., eds.); and "*Recombinant DNA Methodology II*" (R. Wu ed.). Techniques used in raising, purifying and modifying antibodies, and the design and execution of immunoassays, are described in *Handbook of Experimental Immunology* (D. M. Weir & C. C. Blackwell, eds.); *The Immunoassay Handbook* (Stockton Press N.Y.); and *Methods of Immunological Analysis* (Masseyeff et al. eds., Weinheim: VCH Verlags GmbH).

Texts that describe reproductive techniques and embryo transfer in animals include *Manual of the International Embryo Transfer Society: A procedural guide and general information for the use of embryo transfer technology emphasizing sanitary procedures*, $3^{rd}$ ed. (Stringfellow et al., Savoy, Ill.: International Embryo Transfer Society, Savoy Ill.); and *Embryo Transfer in farm animals: A review of techniques and applications* (K. J. Betteridge, ed., Agriculture Canada Monographs No. 16, Ottawa, 1977).

References for human blood group substances include *The Blood Group Antigen Factsbook* (M. E. Reid & C. Lomas-Francis, ed., Academic Press, 1997); and *Blood Cell Biochemistry: Molecular Basis of Human Blood Group Antigens* (J. P. Carton & P. Rouger, eds., Plenum Pub. Corp., 1995). The synthesis of complex oligosaccharides and carbohydrate-specific enzymes are described in *Oligosaccharides: Their Synthesis and Biological Roles* (H. M. I. Osborn & T. J. Khan, Oxford Univ. Press, 2000) and *Glycoscience: Synthesis of Oligosaccharides and Glycoconjugates* (H. Driguez & J. Thiem, Eds., Springer Verlag, 1999).

Books on the general aspects of nuclear transfer, animal cloning, and xenotransplantation include *The Second Creation: Dolly and the Age of Biological Control* (I. Wilmut et al., Farrar Straus & Giroux, 2000), and *Xeno: The Promise of Transplanting Animal Organs into Humans* (Cooper & Lanza, Oxford University Press, 2000).

Strategy for Engineering Tissue with Xenocompatible Carbohydrate Antigens

This invention provides cells, animals, and tissues in which expression of $\alpha1,3GT$ is eliminated by inactivating the endogenous gene, and expression of $\alpha1,2FT$ is induced by introducing a transgene into the genome. In order to obtain complete suppression of $Gal\alpha(1,3)Gal$ expression, the $\alpha1,3GT$ gene needs to be inactivated on both alleles. At least one copy of an expressible $\alpha1,2FT$ encoding region under control of a suitable promoter is also present to confer the desired phenotype.

A convenient method to make an animal with all these features is to perform all the genetic manipulations on a cell or cell population that is then used for cloning. To complete all the genetic manipulations, it is usually necessary to take the cell through a number of rounds of proliferation and selection. After the desired genotype has been obtained and selected, a cell selected from the population can be grown into an embryo (if it is an embryonic cell), or used as a donor for nuclear transfer into a suitable recipient cell, which in turn is used to grow the embryo.

The process can be considerably facilitated by increasing the replicative capacity of the cell population. In particular, increasing the expression of telomerase reverse transcriptase sufficiently increases replicative capacity of the nuclear donor, while minimizing risk of transformation to a malignant phenotype, and conferring other advantages described earlier.

Using this approach, genetically modified cells can be created in which the $\alpha1,3GT$ gene is modified either simultaneously or sequentially on both alleles in the same cell line. One method for generating cells modified on both alleles is to use a single targeting vector in combination with a selection process that requires double integration. The double recombination event is statistically rare, but the extended proliferative capacity of the cell population puts batch screening for such an event within the scope of routine experimentation.

Another method for generating cells modified on both alleles is to use two different targeting constructs. The constructs can each be created with different selection markers that facilitate screening for double integration. For example, the cell can be targeted with a first targeting vector containing a first drug resistance gene, and selected using the corresponding drug. After a round of proliferation, the progeny can then be targeted with a second vector containing a second drug resistance gene, and selected using the second drug. In a variation of this technique, both targeting constructs are used at once, and selection of doubly modified cells is performed in a medium containing both drugs.

The desired phenotype can be obtained by inactivating both α1,3GT alleles, and separately introducing an α1,2FT expression cassette. Alternatively, targeting vectors can be used that removes the α1,3GT start codon, and inserts the α1,2FT expression cassette simultaneously. The α1,2FT encoding region can be provided with its own transcription control elements—or it can be placed under control of the endogenous α1,3GT promoter, which may help direct expression with an appropriate tissue distribution. Once all these manipulations have been made and verified, the cell can be used for cloning the embryo.

It is also possible to arrive at the desired phenotype by making some of the genetic modifications, cloning the embryo, and then making further modifications on a cell from the cloned fetus, newborn animal, adult, or subsequent progeny. For example, the α1,3GT gene can be inactivated or replaced with α1,2FT on one allele, and an animal cloned. Cells from the clone could then be harvested for inactivating or replacing the second α1,3GT allele, and recloned. A further option is to arrive at the desired phenotype by interbreeding—for example, by mating an animal with α1,3GT substituted with α1,2FT on one allele with another animal having a similar genotype (or with just an inactivated α1,3GT allele).

Increasing Telomerase Activity in the Nuclear Donor

Donor cells for genetic manipulation according to this invention are typically nucleated cells of the desired species with a germ line genotype, selected to be easily maintained in culture. Exemplary are primary fibroblast cells, which are relatively easy to prepare from most species. For example, cells are collected from sheep or pig fetuses at about 35 days of gestation, and subjected to mild trypsin/EDTA solution, then cultured in a suitable culture medium. Except where explicitly directed otherwise, the techniques of this invention can be applied to any cell type without restriction, including embryonic cells, primary cells from a fetus, offspring, or adult, and established cell lines from any vertebrate.

The replicative capacity of the nuclear donor cell is increased by increasing telomerase activity. This assists the cells in maintaining telomere length, thereby expanding the replicative capacity (the number of cell doublings possible before reaching the Hayflick limit and entering crisis). Typically, telomerase activity is modified before inactivation of the target gene, but such modifications are also permitted at a later stage in the procedure.

Increasing telomerase activity can be accomplished by a number of strategies, including but not limited to the following:

a) genetically altering the cell with a nucleotide having an encoding region for telomerase reverse transcriptase (TERT);
b) artificially placing TERT protein or telomerase holoenzyme into the cell;
c) altering TERT expression from the endogenous gene; or
d) altering expression of a telomerase related protein, thereby effectively increasing telomerase activity.

A convenient method for increasing telomerase activity is to genetically alter the cells so that they express TERT, which is usually the limiting component of telomerase enzyme expression. A TERT gene can be cotransfected with a gene for the telomerase RNA component, or a TERT can be selected that is compatible with the RNA component already expressed by the cell.

It has been discovered that when cells from large mammals such as sheep and pigs are genetically altered with human TERT, they express increased telomerase activity, which indicates that the hTERT gene product can combine with endogenous RNA component to create a functional enzyme. It is a hypothesis of this invention that combinations of mammalian TERT into the cells of other mammals will often be effective.

The human TERT gene sequence is provided in U.S. Pat. No. 6,166,178, which also describes the use of TERT to increase replicative capacity of various cell types. The mouse TERT sequence is provided in International Patent Application WO 99/27113. Other publications with telomerase-related sequences include International Patent Application WO 98/21343 (Amgen); WO 98/37181 (Whitehead); WO 98/07838A1 (Mitsubishi); WO 99/01560 (Cambia), and U.S. Pat. No. 5,583,016 (Geron Corp.). U.S. Pat. No. 5,968,506 describes purified telomerase and methods for obtaining it. When TERT is referred to in this description, it is understood to mean a polypeptide comprising a TERT sequence from any mammalian, vertebrate, or other species, with or without alterations, so long as the polypeptide has telomerase activity when associated with telomerase RNA component, as measured by TRAP assay (described below) in the cell line being treated.

Typically, the vector will comprise a TERT encoding region under control of a heterologous transcription control element that promotes transcription in the intended undifferentiated or differentiated cell line. Sequences that can drive expression of the TERT coding region include viral LTRs, enhancers, and promoters (such as MPSV, SV40, MoLV, CMV, MSCV, HSV TK), eukaryotic promoters (such as β-actin, ubiquitin, elongation factors exemplified by EF1α, and PGK) or combinations thereof (for example, the CMV enhancer combined with the β-actin promoter). Expression of a marker gene can optionally be driven by the same promoter that's driving the TERT gene, either as a separate expression cassette, as part of a polycistronic transcript (in which the coding regions of TERT and the marker gene are separated by an IRES sequence, allowing both individual proteins to be made from a single transcript driven by a single promoter), or as part of the same cassette (a fusion between the coding regions of both TERT and the marker gene, producing a protein that provides the functions of both TERT and the marker gene). Transfection and expression of telomerase in human cells is described in Bodnar et al., Science 279:349, 1998 and Jiang et al., Nat. Genet. 21:111, 1999.

An alternative strategy is to use a vector that substitutes or supplements the promoter in the endogenous TERT gene with a regulatory control element (such as those listed above) that increase expression in the cultured cells. Further illustration of the general strategy of replacing promoters in endogenous genes can be found in U.S. Pat. No. 6,063,630.

When the nucleus of the telomerized cell is transferred to another cell and used to produce a cloned animal or embryo, the tissue will contain alterations to the genome of the donor cell. The presence of a recombinant TERT gene in a donor cell may have other consequences. Accordingly, it may be desirable to provide a mechanism for removing or otherwise inactivating the recombinant TERT gene once the telomeres have been elongated but before nuclear transfer.

This can be accomplished by flanking the TERT gene and/or the transcription control element on both sides with recognition sequences for a site-specific recombinase. Suitable are lox sites recognized by Cre recombinase (U.S. Pat. No. 4,959,317), and frt sites recognized by Flp recombinase (U.S. Pat. No. 5,929,301). Other site-specific recombinases include XerC (Becker et al., Curr. Microbiol. 32:232, 1996), XerD (Subramanya et al., EMBO J. 16:5178, 1997), xisF (Genes Dev. 8:75, 1994), and Int recombinase (Kolot et al., Mol. Biol. Reprod. 36:207, 1999; Tirumalai et al., Proc. Natl. Acad. Sci. USA 94:6104, 1997). After all the genetic modifications are made to obtain the desired cell-surface carbohydrate antigens, the cell is treated with the corresponding recombinase (or an expression vector for the recombinase) to excise the TERT cassette before nuclear transfer.

Also contemplated are vectors in which a particular gene (such as a selectable marker) is flanked by one type of recombinase recognition site, and the TERT gene or control element is flanked with another type of recognition site. An example is the following:

5'arm-loxP-frt-neopA-frt-pGK promoter-hTERTpA-LoxP-3'arm

This allows the drug resistance marker (neo) to be removed from the line after selection using the first recombinase (Flp), while retaining TERT. Further genetic manipulation can then be performed—for example, targeting the other allele of the same gene, possibly using the same vector and selecting for neo again. After all manipulation is complete, the TERT encoding region can be removed using the second recombinase (Cre).

Another way of obtaining cells with genomic modifications that do not include TERT is to increase telomerase activity without integrating a TERT gene into the genome. For example, TERT can be transiently expressed using a suitable expression system such as adenovirus, or by introducing TERT protein (or the telomerase holoenzyme) directly into the cell. The TERT will be diluted out as the cell divides, but extension of telomeres in the parent cell should increase replicative capacity of the cell line by several doublings.

Another alternative is to upregulate TERT expression from the endogenous gene by upregulating expression of trans-activating transcriptional regulators. The TERT promoter contains a number of regulator recognition sequences, such as c-Myc, SP1, SRY, HNF-3β, HNF-5, TFIID-MBP, E2F and c-Myb. See International Patent Publication WO 00/46355.

A further alternative is not to increase TERT expression, but enhance the effective activity of telomerase already present in the cell. This can be done in cells that have an endogenous level of TERT expression, such as in bone marrow progenitor cells and gonadal tissue. For example, TRF1 and TRF2 are proteins that bind to telomere repeats and regulate access of telomerase (Smogorzewska et al., Mol. Cell Biol. 20:1659, 2000). Decreasing expression of such factors may enhance the ability of telomerase to increase telomere length, thereby increasing replicative capacity of the cell.

Evidence of increased telomerase expression can be obtained by a variety of techniques, including but not limited to determining gene transcript levels (for example, by Northern or RT-PCR analysis), protein expression (for example, by immunocytochemistry), or telomerase activity (for example, by primer extension assay). Extended lifespan or replicative capacity of the treated cells, while often desirable, need not be positively demonstrated for the invention to be put into practice, except where explicitly required.

Telomerase activity can be determined, for example, by TRAP assay (Kim et al., Science 266:2011, 1997; Weinrich et al., Nature Genetics 17:498, 1997), or other suitable technique (e.g., U.S. Pat. No. 5,741,677). Evaluation of hTERT expression by RT-PCR or immunoassay can be done by standard methods, using the sequences disclosed in U.S. Pat. No. 6,166,178. The following assay kits are available commercially for research purposes: TRAPeze® XK Telomerase Detection Kit (Cat. s7707; Intergen Co., Purchase N.Y.); TeloTAGGG Telomerase PCR ELISAplus (Cat. 2,013,89; Roche Diagnostics, Indianapolis Ind.); and Light-Cycler TeloTAGGG hTERT quantification kit (Cat. 3,012,344).

Figure 5:
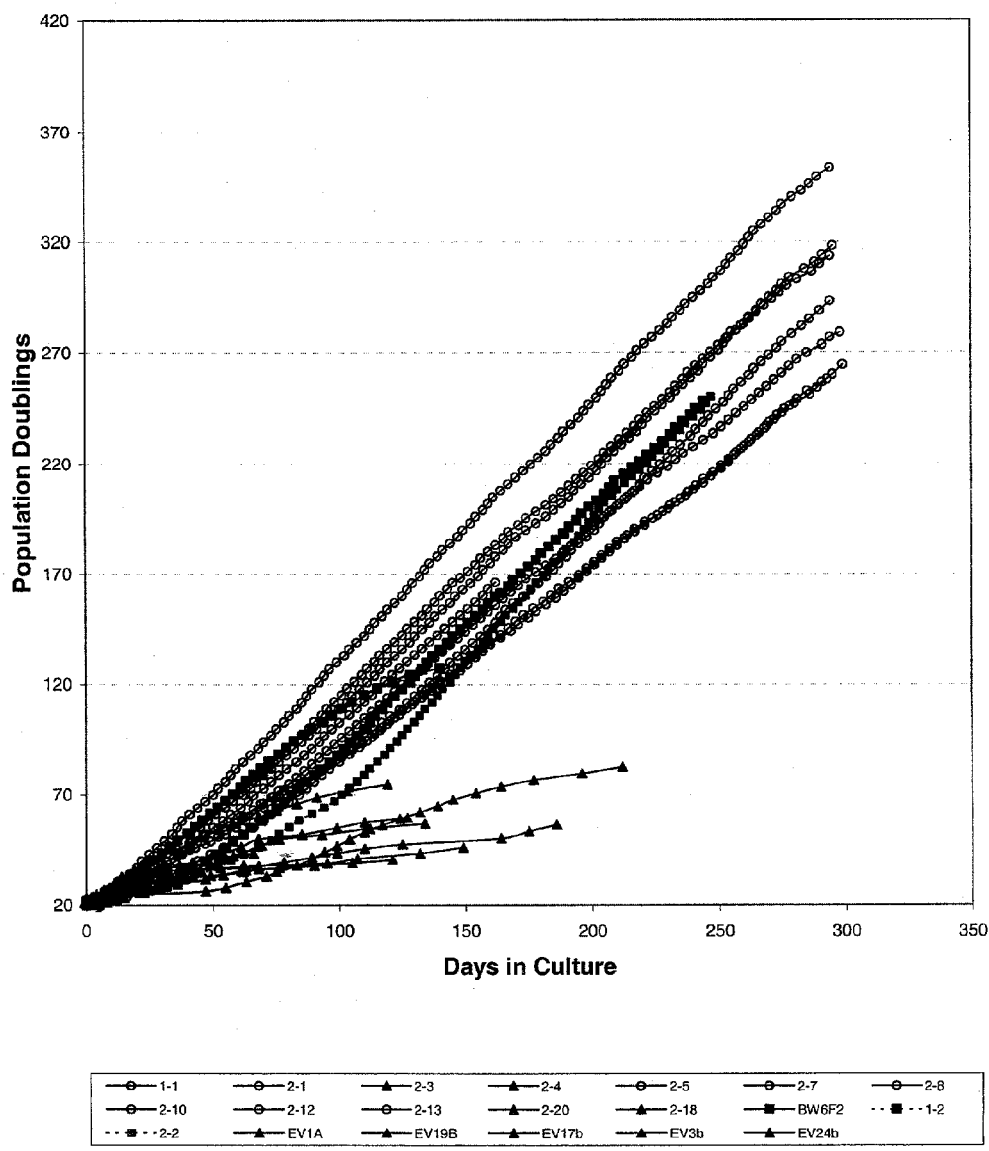
FIG. 5 is a graph of the growth profile for primary sheep fibroblasts transduced to express telomerase reverse transcriptase. Each line is a single clone, except BW6F23, which is the parental (untransfected) fibroblast line. ●=telomerase-expressing clones; ▲=telomerase-negative clones; □=clones that were telomerase-negative initially, but became positive later.

The cells can also be characterized as to their replicative capacity by passaging cells and monitoring the number of cell doublings. Unmodified fetal fibroblasts will typically grow through a number of doublings until they reach the Hayflick limit, and then enter into senescence. As illustrated in FIG. 5, cells may grow indefinitely if TERT continues to be expressed.

Modifying the Galactosyltransferase Gene

Once the cell line has been obtained and established in culture, genetic manipulations can be performed to: a) eliminate expression of the endogenous α1,3GT gene; and b) provide for expression of α1,2FT to fucosylate the same N-acetyl lactosamine acceptor.

There is a variety of ways the endogenous α1,3GT gene can be inactivated. For example, a control element that regulates transcription (such as a promoter or transcription start sequence) can be altered or deleted. Alternatively, the gene can be adapted so that any gene product that is produced lacks the essential features of a glycosyltransferase. The encoding region can be interrupted with stop codons, the encoding region can be placed out-of-phase, or critical portions of the protein may be missing, such as a structural component or a signal peptide for secretion. In another alternative, the gene can be adapted so that the protein product lacks the specificity of α1,3GT—either because the catalytic site is removed, or because substrate binding specificity has been sufficiently altered so that the enzyme is incapable of synthesizing the Galα1,3Gal linkage.

The α1,3GT gene can be targeted by homologous recombination, using a vector comprising nucleotide sequence identical or nearly identical to a portion of the gene of interest, linked to another structure capable of introducing the alteration. Such vectors typically have two regions flanking a region of the genome intended for deletion. Between the flanking regions, there is often an additional segment that becomes inserted in the gene in place of the region that is excised.

The insert region can include a selectable marker, so that targeted cells can rapidly be separated from untargeted cells. U.S. Pat. No. 5,614,396 describes a method for obtaining a cell containing a desired sequence in the cell's genome, by using a targeting vector having two regions homologous to the targeting sequence, flanking a sequence that is to be inserted, and having a selectable marker. The DNA undergoes homologous recombination at the target site, and recombined cells are recovered under selective culture conditions.

Positive selection markers include the neo gene, selectable using G418 or kanamycin; the hyg gene, selectable using hygromycin; the pac gene, selectable using puromycin; the gpt gene, selectable using xanthine; and hypoxanthine-phosphoribosyltransferase (HPRT), selectable using hypoxanthine. Negative selection markers include thymidine kinase (tk), selectable using acyclovir or ganciclovir; HPRT, selectable using 6-thioguanine; and cytosine deaminase, selectable using 5-fluoro-cytosine. Markers can also have an intrinsic label, like green fluorescent protein or β-galactosidase, which permit clones of targeted cells to be identified and selected.

Further methodology for homologous recombination is described in the published literature. U.S. Pat. Nos. 5,464,764 and 5,631,153 provide a double-selection strategy, in which two sequences homologous to the gene target flank a positive selection marker, and a negative selection marker is attached to the 3' terminal of the second flanking region. Homologous integration retains the positive selection marker, but eliminates the negative selection marker, whereas random integration usually retains both markers. Thus, by screening for both markers sequentially or together, cells that have been correctly targeted will be positively selected, and those that have been incorrectly targeted are selected out. U.S. Pat. No. 5,789,215 reports the use of homologous recombinant targeting vectors for modifying the cell genome of mouse embryonic stem cells. See also U.S. Pat. Nos. 5,589,369 and 5,776,774.

Example 1 illustrates targeting vectors that are capable of inactivating the sheep α1,3GT gene (SEQ. ID NOs:3 & 4) via homologous recombination. Vectors p0054, p0079, and p0063 (Example 1, FIG. 2) are targeted to eliminate Exon 4, which contains the α1,3GT translation start codon. Other vectors have been obtained that target Exon 8 or Exon 9, which is thought to encode at least part of the α1,3GT catalytic site. The α1,3GT gene in other species can be targeted in a similar fashion, using probes having flanking sequence for the α1,3GT of that species. The bovine and porcine α1,3GT cDNA sequences are provided in SEQ. ID NOs:5–8.

The vectors comprise flanking regions identical to the targeted α1,3GT sequence, one side being about 1 kb, the other being at least 1 or 2 kb, in either order. In between the flanking regions is a selectable marker such as neo, designed to replace one of the Exons in the α1,3GT coding sequence. The selectable marker genes are not provided with their own promoter, and require continued translation through the upstream α1,3GT sequence in order to be expressed. This helps the marker select for properly integrated vector, because vector inserted at a random site will probably not link the marker gene to a suitable promoter, and resistance to the selector drug will not be conferred. In cells that normally express a high level of α1,3GT and the Galα(1,3)Gal epitope, the α1,3GT promoter will be highly active and the drug resistance marker will be strongly expressed. Thus, a higher concentration of selector drug can be used to select out cells that have the vector inserted elsewhere.

The insert region of the targeting vector can also contain an encoding region for α1,2FT. This way, inactivation of the endogenous α1,3GT gene and integration of the α1,2FT will occur simultaneously with a successful targeting event. The α1,2FT gene can be placed in the targeting vector linked to its own promoter, or the targeting vector can be constructed in such a way that the α1,2FT gene will be placed under control of the endogenous α1,3GT promoter once integrated.

Larsen et al. (Proc. Natl. Acad. Sci. USA 86:8227, 1989) describe the molecular cloning, sequence, and expression of human GDP-L-fucose: β-D-galactoside 2-α-L-fucosyltransferase cDNA that can form the H blood group antigen (i.e., α1,2FT). The nucleic acid sequence and encoded protein sequence is shown in SEQ. ID NOs:9 and 10. Wagner, et al. (Transfusion 37:284, 1997) provide allotypic variants of the human α1,2FT. Apoil et al. (Mol. Biol. Evol. 17:337, 2000) describe evolution of the α1,2FT gene in primates, and provide encoding sequences from *Gorilla gorilla, Pan troglodytes, Macaca mulatta*, and other higher primates. Any fucosyltransferase can be used if it converts the N-acetyl lactosamine acceptor to a determinant that is immunologically equivalent to H substance.

Vectors for replacing the α1,3GT encoding region in sheep and pigs with the human α1,2FT are shown in FIG. 6 (Example 4). The target cells are contacted with the targeting vector in such a manner that the vector gets entry into the cell nucleus and effects the intended change. Any suitable method of transfection can be used, such as electroporation and lipofection. The vector can also be truncated for insertion into a viral particle (such as an adenovirus vector) that can then be used to transduce the cells. Examples 2 and 5 illustrate the use of targeting constructs on sheep fibroblast cultures suitable for nuclear transfer.

As an alternative to homologous recombination, a target gene can be inactivated using triplex-forming oligonucleotides that induce intrachromosomal gene conversion (Luo et al., Proc. Natl. Acad. Sci. USA 97:9003, 2000; Barre et al., Proc. Natl. Acad. Sci. USA 97:3084, 2000). Other techniques and reagents can be found in Inonue et al., J. Virol. 73:7376, 1999; Cole-Strauss et al., Science 273:1386, 1996; Hasty et al., Mol. Cell Biol. 11: 4509, 1991; and International Patent Publication WO 98/48005.

In instances where the α1,3GT gene has been inactivated without integrating an α1,2FT encoding region into the genome, a separate manipulation is required to confer the full phenotype. A vector is made for introducing the α1,2FT region, typically under control of a promoter that is active in an appropriate tissue distribution, such as the native α1,2FT promoter, or one of the model promoters listed earlier. The expression cassette can then be integrated into the genome at any location by any appropriate technique, such as homologous recombination, or transduction with a retroviral or DNA viral vector.

Selection and Characterization of Targeted Cells

Each genetic manipulation can be selected and verified according to genotypic and phenotypic markers.

Where cells have been transfected with a vector bearing a drug resistance marker, successfully targeted clones can be selected by culturing in a medium containing the corresponding drug. Modification of one or both alleles can be confirmed by PCR of genomic DNA, using primers from flanking endogenous α1,3GT sequence, showing that the segment length has changed, or using a primer for the inserted sequence in combination with an α1,3GT primer, showing that the sequence is integrated in the correct region. Southern analysis using probes for flanking endogenous α1,3GT sequence will show altered restriction analysis, and probes for the inserted sequence will confirm the presence and orientation of the insert. In-situ hybridization of genomic DNA can be used to verify the correct location of the modification.

Targeted clones can also be selected and verified based on gene transcripts and the resulting cell phenotype. mRNA can be characterized by Northern analysis or RT-PCR. Cells where the α1,3GT gene has been inactivated on both alleles will not express the Galα(1,3)Gal epitope. The determinant can be identified using a specific antibody or lectin. Purified antibody can be obtained from pooled human serum by adsorbing on an affinity column of Synsorb™ 115 (Chem-BioMed, Alberta, Canada) or D(+) melibiose (Sigma). An alternative is the "IB4" lectin from *Bandeiraea* (*Griffonia*) *simplicifolia* (Sigma Cat. L 3019) which is specific for α-D-galactosyl residues (Hayes et al., J Biol. Chem. 25:1904, 1976), and binds both the Galα(1,3)Gal epitope, and B blood group substance.

Antibody to Galα(1,3)Gal can be used to select for homozygous knockouts by complement lysis. Targeted cells are combined with a source of the antibody (such as human serum), and a source of complement, (such as fresh plasma from the same species as the cells, or commercially available guinea pig complement). The mixture is incubated at 37° C. for a sufficient period to lyse cells expressing Galα(1,3)Gal (or halt their growth), using untargeted cells as a control. Surviving cells should have α1,3GT inactivated on both alleles. Specific antibody or lectin can also be used to isolate homozygous knockout cells by affinity techniques, such as panning, affinity adsorption, or fluorescent-activated cell sorting.

Incorporation and expression of the α1,2FT encoding region can be determined using antibody or lectin specific for H substance. Ulex Europaeus agglutinin I (UEA-1) is a lectin with affinity for the terminal L-fucose on H substance (Matsumoto et al., Biochim. Biophys. Acta 194:180, 1969). The lectin can be used for immunoseparation of cells in which α1,2FT is active. Most mature pig and sheep cells do not normally bind UEA-1 (Spencer et al., J. Histochem. Cytochem. 40:1937, 1992; K. J. Fahey, Aust. J. Exp. Biol. Med. Sci. 58:557, 1980). UEA-1 is available from Sigma Chemical Co. or Vector Labs in purified form, labeled with fluorescein or biotin, or insolubilized on beaded agarose. Conrad-Lapostolle et al. (Cell. Biol. Toxicol. 12:189, 1996) describe optimization of UEA-1 magnetic beads for endothelial cell isolation. UEA-1 labeled with a fluorescent tag can be used to separate targeted cells by fluorescence-activated cell sorting.

Using specific antibody and lectin in appropriate combination, it is possible to select cells with the full α1,3GT negative, α1,2FT positive phenotype without having drug resistance labels in the targeting vectors. For example, the cells can be targeted with a vector that substitutes α1,2FT for α1,3GT on one allele, and selected by positive adsorption to UEA-1. The selected cells are expanded, and then targeted with a similar vector to knock out the second allele. The targeted cells are then subject to complement lysis using antibody to the Galα(1,3)Gal determinant in human serum, or depleted of cells binding IB4 lectin. Surviving cells are again expanded, cloned, and analyzed for correct genotype, expression of α1,2FT mRNA, lack of expression of α1,3GT mRNA, and correct expression of cell surface oligosaccharide determinants. Of course, drug selection, affinity selection, and selection by other criteria can be combined in any effective combination to obtain the phenotype desired.

ABO Transferases and Other Transgenes

Group H substance formed by α1,2FT in turn can be used as an acceptor for the human ABO histo blood group transferases, to create the allotypic markers characteristic of a particular ABO blood type. Blood group A-transferase adds GalNAc to the Gal residue on Fucα(1,2)Gal-GlcNAc, to form GalNAcα(1,3)[Fucα(1,2)]Gal-GlcNAc (A substance). Blood group B-transferase adds Gal instead to form Galα(1,3)[Fucα(1,2)]Gal-GlcNAc (B substance).

Certain embodiments of the invention provide animal tissue that not only expresses H substance, but also has at least some of it converted to A or B substance. To provide tissue of the human A blood group, the cells express blood group A-transferase in one or more copies. To provide tissue of the human B blood group, the cells express blood group B-transferase. To provide tissue of the human AB blood group, the cells express both A-transferase and B-transferase.

The nucleotide and protein sequence of human A-transferase and B-transferase are provided in SEQ. ID NOs: 11–14. See also U.S. Pat. Nos. 5,068,191 and 5,326,857. ABO transferase enzymes of other primate species can be found in Sumiyama et al., Gene 259:75, 2000. The transferase encoding sequence is placed in a vector suitable for introducing a transgene into the cell, for example by homologous recombination or retrovirus transduction. The sequence is linked to transcription control elements that promote expression in the appropriate cell types, such as the homologous transferase promoter, the α1,3GT promoter, or the α1,2FT promoter. Cells are then selected for successful targeting, and characterized according to whether they express A or B substance (for example, using antibody from human blood group B or A serum, respectively).

If desired, the cells can be adapted with other genetic modifications to enhance its suitability for the ultimate purpose. Xenocompatibility can be enhanced by increasing expression of complement inhibitor such as CD59, DAF or MCP (International Patent Application WO 97/12035). It is also believed that tissues or organs containing cells that are genetically modified to render them incapable of expressing CD40 antigen have lower risk of chronic xenograft rejection (International Patent Application WO 00/39294). Other xenogeneic antigens, such as that identified in WO 00/57912 or histocompatibility markers, can also be deleted or humanized to increase immunocompatibility.

Carbohydrate Tags as a Selection System for Homologous Recombination

Surface carbohydrate-based cell selection (as described above and illustrated in Example 5) was conceived and developed as a general system for identifying targeted homologous recombination events in any context. The advantages of using carbohydrate determinants as selection markers are multiple:

A change in carbohydrate determinant can be generated either by introduction of a new carbohydrate modulating enzyme, or by inactivation of carbohydrate modulating enzyme expressed from an endogenous gene. Where a new transgene is introduced into the cell, it can be a close homolog to a naturally occurring enzyme, thereby minimizing antigenic complications from the protein itself.

The strategy of sorting by inactivation of an endogenous carbohydrate modifying enzyme is particularly attractive, because the change is effected only by integration of the vector into the correct locus. This is important, because the frequency of integration into random (non-target) sites can be 10-fold higher than the frequency of correct homologous recombination.

Many glycosyltransferases (such as those that create the blood group antigens) are expressed in a wide variety of cell types from the endogenous promoter (Ravn et al., APMIS 108:1, 2000), meaning that inactivation screening can be designed that is not cell-type restricted.

A wide variety of lectins is available for robust separation of the cells either by adsorption or fluorescent tagging techniques. Elution of the selected cells can be accomplished under gentle conditions using carbohydrate competitor ligand.

Since cell-surface carbohydrate determinants are modulated by enzymes such as a glycosyltransferase or a glycosidase, the density of surface determinants is catalytically (not stochiometrically) related to the amount of protein translation. Increased antigen density may enhance the likelihood of successful antibody or lectin-based separation.

Negative selection according to this system can be accomplished by designing the targeting vector to interrupt the encoding sequence for the target carbohydrate modulating enzyme with a sequence that prevents transcription or translation of the functional gene product. The targeting vector may optionally include other elements to be introduced into the target site, such as a transgene or recognition sequence for a site-specific recombinase.

Positive selection according to this system can be accomplished by including in the targeting vector a glycosyltransferase or glycosidase that is not endogenous to the species or phenotype of the cell being targeted. After the targeting reaction, cells are selected for the determinant created by the encoded modulating enzyme, and then checked for proper integration of the vector. Putting the modulating enzyme into the cell need not be the ultimate objective of targeting, it can just piggyback on the vector as a way of following the reaction. The ultimate objective of targeting could be to inactivate an endogenous gene (which may but need not encode another carbohydrate modulating enzyme). It could also be to introduce another genetic element into a particular locus—such as a different transgene (powered by a different promoter or separated from the enzyme encoding region by an IRES sequence), or a recognition sequence for a site-specific recombinase. Where the enzyme encoding region is present in the targeting vector only for use as selection tag, it can optionally be removed after the targeted cell line is established—for example, by site specific recombination.

Carbohydrate binding means that detect modulations in carbohydrate determinants include specific antibody (anti-A, present in blood group B serum; anti-B, present in blood group A serum; and anti-Galα(1,3)Gal, present in virtually all human serum). Also included are specific lectins. The following are available commercially: H-specific lectins from *Anguilla anguilla, Tetragonolobus pupureas*, and *Ulex europaeus* UEA-1, which of course also binds Galα(1,3) Gal. A-specific lectins from *Helix pomatia, Dolichos biflori, Helix aspersa, Phaseolus limensis*, and *Bandeiraea simplicifolia* (IA4). B-specific lectin: *Ptilota plumosa*, and *Bandeiraea simplicifolia* (IB4).

Methods of separation can involve adhering the antibody or lectin to a solid surface, contacting the surface with the cells, and collecting cells that adhere or do not adhere to the solid surface. Other methods of separation involve conjugating the antibody or lectin with a flurescent, phosphorescent, or other labeling means, contacting the cells with the labeled tag, and then separating tagged from non-tagged cells, for example, in a fluorescence-activated cell sorter. Another seperation method involves using antibody to bind the distinguishing determinant on the cells, thereby opsonizing them for complement-mediated lysis.

In principle, this selection system can be used in any eukaryotic cell capable of expressing distinguishable carbohydrate determinants on the cell surface. As illustrated at various places in this disclosure, the system can be employed on cells of most vertebrate or mammalian species.

An illustrative example of the use of this system is the modification of pluripotent stem cells, such as human embryonic stem cells or germ cells (U.S. Pat. Nos. 6,200, 806 and 6,331,406; International Patent Publications WO 99/20741 and WO 01/51616) or their derivatives (WO 01/81549; WO 01/88104). The cells are first genotyped for ABO blood group by PCR amplification (Lee et al., Forensic Sci. Int. 82:227, 1996). Cells that are AO or BO genotype have the advantage that knocking out the single enzymatically active allele will change the surface phenotype of the cell.

The ABO locus is then targeted with a vector containing a genetic element to be introduced into the genome of the cell, flanked on either side by portions of the A- or B-transferase genomic sequence. Cells that are successfully targeted are separated by their ability to bind the *Helix pomatia* lectin for A-substance, or the IB4 lectin for B-substance. Accuracy of the targeting can be confirmed, for example, by PCR amplification or Southern analysis of genomic DNA. An advantage of this strategy is not only the effective selection of the targeted cells, but the fact that the ABO blood group enzyme is inactivated as a consequence—giving the cells the blood group O phenotype, which makes them universal donor cells with respect to ABO blood group.

In a variation of this example, positive rather than negative selection is used to follow gene targeting. Cells are selected that have the OO genotype, and targeted at the ABO locus by a vector that introduces A- or B-transferase flanked on each side by site-specific recombinase recognition sequences. Cells are positively selected for binding to *Helix pomatia* or IB4 lectin. Then the cells are transfected to transiently express the corresponding recombinase enzyme. As a result, the active transferase is excised, and the cells revert to the blood group O phenotype, leaving a single recombinase recognition sequence in the locus. This then can be used to introduce a variety of transgenes into the line by site-specific recombination. It is a theory of this invention that since ABO blood determinants are expressed on most nucleated cells, this site will facilitate stable expression of the transgene—since it may be immune to inactivation that might occur elsewhere in the genome as the cells proliferate and proceed down the differentiation pathway.

A second illustration of the carbohydrate mediated selection system is the use of fluorescently labeled lectins and single-cell sorting to rapidly obtain cells in which the α1,3GT gene has been replaced with α1,2FT.

Early passage animal cells are transfected by electroporation with 10 µg NotI linearized p0090 (a promoterless vector that targets the α1,3GT locus and inserts α1,2FT; Example 4). Only cells that integrate the α1,2FT sequences downstream and in-frame to an active promoter will express α1,2FT protein, and hence present H substance on the cell surface. Following transfection, a period of 24 hours of growth in complete medium is sufficient to allow expression of α1,2FT and synthesis of H substance on the cell surface (FIG. 7).

Cells expressing α1,2FT and synthesizing H substance are isolated by their ability to bind UEA-1 lectin as follows. The transfected culture is washed with HEPES buffer (0.15 M NaCl, p.01 M HEPES, pH 7.5) and then incubated for 30 min with rhodamine conjugated UEA-1 lectin (Vector Labs), diluted 1:50 in HEPES buffer. Excess lectin is removed by three washes with HEPES buffer. Cells binding the lectin are separated by FACS analysis (Becton Dickenson) such that individual fluorescent cells deposited into single wells of a 96-well plate—thereby avoiding cultures that contain mixed populations of targeted and non-targeted cells. As an alternative to the single-cell sorting technique, the targeted cell population can be seeded at a density of ~50 cells in a 10 cm dish. After growth and expansion, the resulting colonies (>100 cells per colony) are ring-cloned and deposited to 96-well plates for DNA analysis.

The cells are allowed to proliferate in complete growth medium until cultures are subconfluent. At this time, the cells are replica plated; one plate for cryopreservation and later recovery, and the other plate for DNA analysis by PCR. Wild type and targeted α1,3GT alleles are detected using sense (399010, 5'-CAGCTGTGTG GGTATGGGAG GG-3'; SEQ. ID NO:27) and antisense (499006, 5'-CTGAACTGAA TGTTTATCCA GGCCATC-3'; SEQ. ID NO:28) PCR primers, yielding products of 3.0-kb and 2.4-kb, respectively. A second PCR screen with primers 399010 (SEQ. ID NO:27) and 399111 (5'-TGACGATGGC TCCGGAGCCA CAT-3'; SEQ. ID NO:40) produces a fragment of 1.7-kb only in clones that are correctly targeted. Successful targeting can be confirmed by Southern blot analysis.

The genetically altered cells can then be used for nuclear transfer, establishing additional cell lines, or for any other desirable purpose.

Nuclear Transfer

Cells that have been successfully targeted and selected according to this invention can be used as nuclear donors by transferring into an enucleated recipient cell.

Suitable recipient cells include oocytes or any other pluripotent cell that is capable of developing into a fertile embryo after transfer and activation. International Patent Application WO 97/07669 (Roslin Institute) describes quiescent cell populations for nuclear transfer. International Patent Application WO 97/07668 (Roslin Institute) describes inactivated oocytes as cytoplast recipients for nuclear transfer. For purposes of prosecution in the U.S., these patents and patent applications are hereby incorporated herein by reference in their entirety.

Nuclear transfer methods are particularly effective if the nucleus of the donor cell is quiescent, which can be achieved by culturing the donor cell in a serum-free medium (WO 97/07669). In an exemplary method, the nucleus of a donor cell is transferred into an oocyte that is arrested in the metaphase of the second meiotic division, and subsequently activating the reconstituted cell. Briefly, unfertilized metaphase II oocytes are collected as follows: Female animals are synchronized using progestagen sponges for ~14 days, and induced to superovulate with single injections of follicle-stimulating hormone on two successive days. Ovulation is induced or synchronized with a suitable dose of gonadotrophin-releasing hormone or an analog thereof (e.g., ~8 mg GnRH Receptal™, Hoechst, UK) on the following day. The oocytes are recovered by flushing from the oviduct one day later, washed, and enucleated by treating with cytochalasin B and aspirating the nucleus using a glass pipette. Enucleated oocytes are then placed into contact with a single cell that acts as the nucleus donor.

Fusion of the donor nucleus into the enucleated recipient cell is effected by placing the couplet in a fusion chamber and aligning it between the electrodes. Electrical pulses are then applied to induce fusion, typically a low-voltage AC pulse for several seconds, followed by a plurality of very short high-voltage DC pulses. Following an incubation period, activation is induced by application of an additional electrical pulse. The reconstructed zygote is then cultured for a time before engrafting into a surrogate female. Further details and alternative procedures are described in the patent publications cited above.

Estrus in the surrogate female is typically synchronized artificially using a suitable combination of inducing agents. Cameron et al. (Aust. Vet. J. 66:314, 1989) discuss synchronization methods and other practical aspects for commercial embryo transfer in pigs. Blum-Reckow et al. (J. Anim. Sci. 69:3335, 1991) report experiments relating to transfer of pig embryos after long-term in vitro culture. Replacing medium every 12 h during culture improved survival, and pregnancy rate improved if the sexual cycle of recipients was 24 h behind that of the donor.

The embryos are introduced into the uterus of the recipient female using any suitable technique, including devices adapted for the purpose, or appropriate surgical methods. For example, U.S. Pat. No. 4,326,505 describes surgical procedures for embryo transplants in animals, in which the uterine horn is positioned in the peritoneal cavity proximate to the vaginal wall, a cannula is inserted through the vaginal wall and into the uterine horn, and the embryo is introduced through the cannula. Non-surgical methods include using a suitable device to manipulate the injection port through the folds of the cervix to the bifurcation of the uterus. For example, devices and techniques for porcine non-surgical embryo transfer are reported by Li et al. (J. Anim. Sci. 74:2263, 1996). Wallenhorst et al. (J. Anim. Sci. 77:2327, 1999) describe the effect of transferring pig embryos to different uterine sites.

Preparation and use of Tissue Expressing ABO Blood Group Determinants

Once an animal has been obtained that has the desired genetic alterations, tissue can be harvested and characterized.

The genomic features of the α1,3GT locus, and expression of α1,3GT or α1,2FT transcripts can be verified using criteria already described. Density of Galα(1,3)Gal and H substance on the cell surface can be determined using specific antibody or lectin in immunocytochemistry or fluorescence labeled flow quantitation methods. Susceptibility of the cells to complement lysis can be determined as follows. Tissue cells from the animal are suspended and labeled with $^{51}$Cr. The labeled targets are combined with diluted human serum as a source of both antibody and complement, and then incubated for several hours at 37° C. Release of the $^{51}$Cr label correlates with density of Galα(1,3)Gal on the surface of the target cells. For further details of assays for α1,3GT inactivation and Galα(1,3)Gal determination, the reader can consult U.S. Pat. No. 5,849,991.

If the animal is confirmed to be α1,3GT negative and α1,2FT positive, it can be used for investigational purposes, or as a source of any tissue type that is desired for xenotransplantation. Possible harvest tissue includes but is not limited to whole organs, such as kidney, liver, heart, lung, eyes, and pancreas; solid tissue, such as skin, cartilage, pancreatic islets, and vasculature of various types; and cell suspensions, such as progenitor cells for regeneration of neural tissue, hematopoietic tissue, hepatocytes, or other cell types.

If the animal has the α1,3GT gene replaced with α1,2FT on both chromosomes, the phenotype should breed true. However, if there is only one α1,2FT gene, then of course it will segregate in the progeny of the cloned animal according to mendelian genetics. The α1,2FT positive phenotype can be maintained by testing the phenotype of each offspring, in combination with an appropriate cross-breeding strategy. Alternatively, the α1,3GT negative α1,2FT positive parent can be cloned as needed to provide the required amount of tissues and organs for research and commercial use.

Cells and tissue harvested from α1,3GT inactivated, α1,2FT expressing tissue can be tested for compatibility according to standard protocols. Antigen expression can be determined by immunocytochemistry, using the IB4 lectin or antibody obtained from human serum. Compatibility with the potential recipient is assessed in part using recipient's serum to test the tissue for cytochemical staining, or in a cytotoxicity assay. Xenotransplantation can be modeled in non-human animals that do not normally express the Galα (1,3)Gal antigen, including GAL knockout mice (see Gock et al., Xenotransplantation 7:237, 2000) or cattharine non-human primates.

The Following Examples Provided as Further Non-limiting Illustrations of Particular Embodiments of the Invention.

EXAMPLES

Example 1

Construction of Vectors for Inactivating Galactosyltransferase

This example describes vectors that inactivate the α(1,3) galactosyltransferase (α1,3GT) gene by homologous recombination.

The sequence of the sheep cDNA for α1,3GT is shown in SEQ. ID NOs:3 & 4. To develop genomic constructs, DNA was isolated from Black Welsh Mountain fetal fibroblasts, and a λDASHII phage library was constructed. Sau3A partially digested genomic DNA was dephosphorylated and ligated to compatible BamHI vector arms (Stratagene). The ligation products were packaged to produce recombinant phage, which were propagated on spi selective XL1-Blue-MRA(P2) bacterial cells. The resulting library had a complexity of $1.4 \times 10^6$ recombinants, and was subsequently amplified once. Six phage clones were isolated that spanned Exon-4, Exon-6–7 and Exon-9.

Recombinant phage designated B, C and G, have been deposited as a pooled sample with the National Collections of Industrial and Marine Bacteria Limited (NCIMB), Aberdeen, U.K, under Accession No. NCIMB 41056. The phage can be separated using the oligonucleotide probes 5'-GG-GAGGAAGC GAAGGTGCA-3' (SEQ. ID NO:15), 5'-CT-TGATGGGT TTATCCAGAA CA-3' (SEQ. ID NO:16) and 5'-TGATAATCCC AGCAGTATTC-3' (SEQ. ID NO:17), respectively. Each recombinant phage has also been deposited separately with the NCIMB under the following Accession numbers: Clone B, No. 41059; Clone C, No. 41060; and Clone G, No. 41061.

Figure 1:
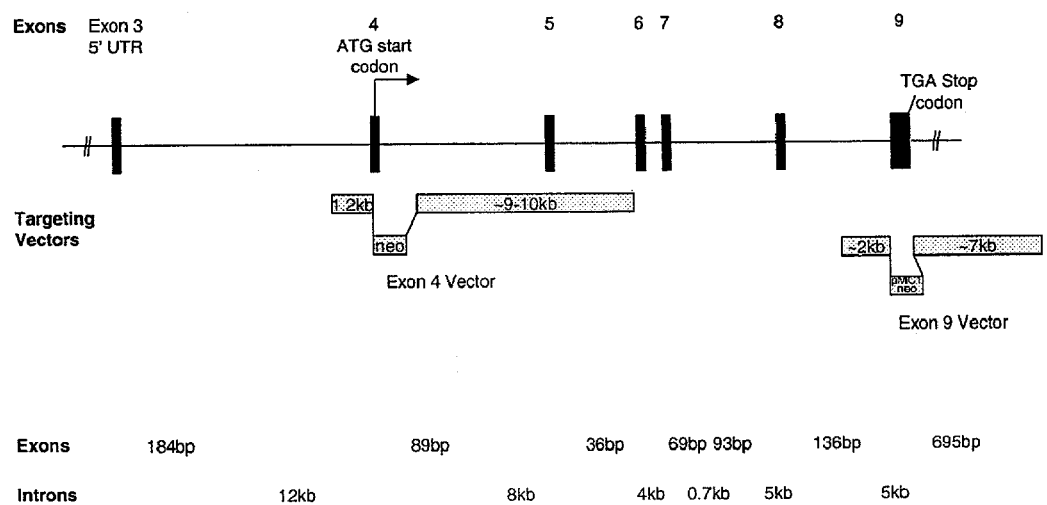

FIG. 1 maps the sequenced intron regions of α1,3GT to their positions in the gene. Exon 4 contains the translation start codon. Also shown are designs for exemplary targeting vectors that disrupt gene expression by excising Exons 4 and 9 by homologous recombination.

Several recombinant vectors were constructed for targeting Exon 4 of the sheep α1,3GT gene. The vector comprises two regions that are complementary to genomic sequence; α1.2-kb 5' arm, which includes sequence from Intron 3 leading up to and including the start codon in Exon 4, and a ~9-kb 3' arm that initiates 1.5-kb into Intron 4, continuing to Intron 5. Separating these regions is $neo^R$-polyA sequence. After homologous recombination, the vector confers neomycin phosphotransferase resistance to the cells and deletes 1.5-kb of genomic sequence, including the first coding exon of α1,3GT gene. The entire cassette was cloned into pBlueScript™ for propagation in DHα bacterial cells.

Figure 2:
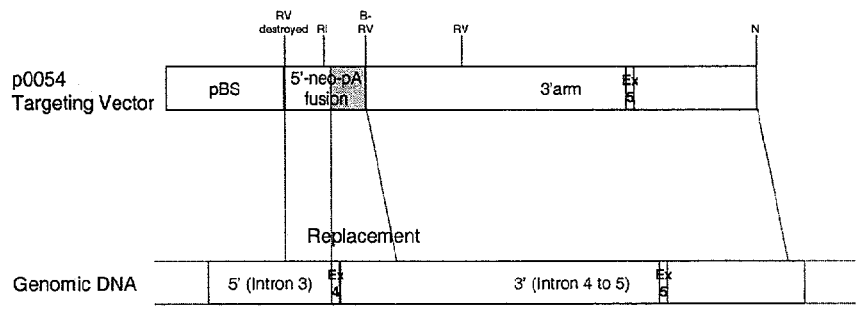
Figure 2:
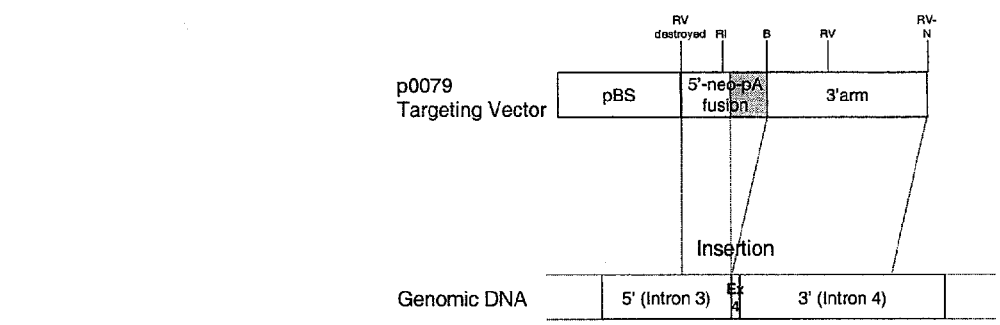
Figure 2:
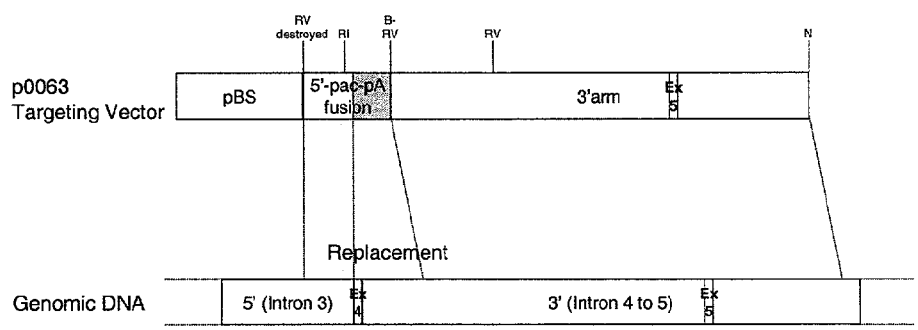

FIG. 2, Top Panel, shows the vector designated p0054. It was constructed by amplifying a truncated left arm (300 bp, includes EcoRI site) (using primers 199001, 5'-ACGTG-GCTCC AAGAATTCTC CAGGCAAGAG TACTGG-3', SEQ. ID NO:18; and 199006, 5'-CATCTTGTTC AATGGC-CGAT CCCATTATTT TCTCCTGGGA AAAGAAAAG-3', with tail complementary to the start of neo coding sequence, SEQ. ID NO:19), and a neo-polyA sequence obtained from Stratagene (using primers 199005, 5'-CTTTTCTTTT CCCAGGAGAA AATAATGGGA TCGGCCATTG AAC-MGATG-3', SEQ. ID NO:20, with tail complementary to left arm; and 199004, 5'-CAGGTCGACG GATCCGAACA AAC-3', SEQ. ID NO:21). These fragments were used to prime from each other to give a 1.2-kb fusion product. This was ligated to Intron 3 sequence, to extend the left arm, and to ~9-kb of 3' sequence to create the right arm, which initiates 1.5-kb into Intron 4, continuing to Intron 5.

FIG. 2, Middle Panel, shows the promoterless neopolyA insertion vector designated plasmid p0079. This vector contains the same left arm-neo-polyA fusion as in vector p0054, but with a modified right arm of 3.9-kb. The 3' region comprises a 1.5-kb fragment, generated by PCR (using primers 200011, 5'-CAGATCTMC GAGGATTCAATGTC-MAGGA AAAGTGATTC TGTCAAT-3', SEQ. ID NO:22; and 499006, 5'-CTGAACTGAA TGTTTATCCA GGC-CATC-3', SEQ. ID NO:23), which extends from the second codon in Exon 4 into Intron 4, replacing the sequence deleted in p0054. The 3' arm was extended by ligation to a 2.4-kb EcoRV downstream fragment.

FIG. 2, Lower Panel, shows the promoterless pac-polyA replacement vector designated plasmid p0063, also directed towards Exon 4. Construction of this vector was similar as for p0054, except that it contains the pac gene, which codes for puromycin N-acetyltransferase, rather than the neo gene. The pac sequence is available in plasmid pPUR from ClonTech. The oligonucleotide primers used to generate the 5'-pac-polyA fusion were, for the 5' region, 199001 (SEQ. ID NO:18) and 699002 (5'-GCGCACCGTG GGCTTG-TACT CGGTCATTAT TTTCTCCTGG GAAAAGAAAA G-3', SEQ. ID NO:24), with tail complementary to the start of pac coding sequence; and, for pac-polyA, 699004 (5'-GAGMAATAA TGACCGAGTA CAAGCCCACG GTGC-3' SEQ. ID NO:25), with tail complementary to left arm, and 699005 (5'-CTGGGGATCC AGACATGATA AGATAC-3'SEQ. ID NO:26).

Example 2

Targeting the Galactosvltransferase Gene

Electroporation conditions were optimized using a β-galactosidase marker plasmid, pCMV-Sport-βgal (Gibco). Using a 0.4 cm cuvette with $3 \times 10^5$ cells (0.8 mL, 6 μg plasmid DNA) and a setting of 250 μF: 400 Volts (Gene Pulser, BioRad), 10–30% of the surviving fibroblasts stained positive for β-gal expression.

For targeting the α1,3GT gene, 10, 25 or 100 μg of NotI linearized p0054 vector was mixed with $1 \times 10^7$ early passage Black Welsh Mountain fetal fibroblasts and pulsed. Cells were grown on tissue culture plastic for 24 h before G418 (300 μg/mL) was applied. After 10–14 days, colonies were isolated.

Figure 3:
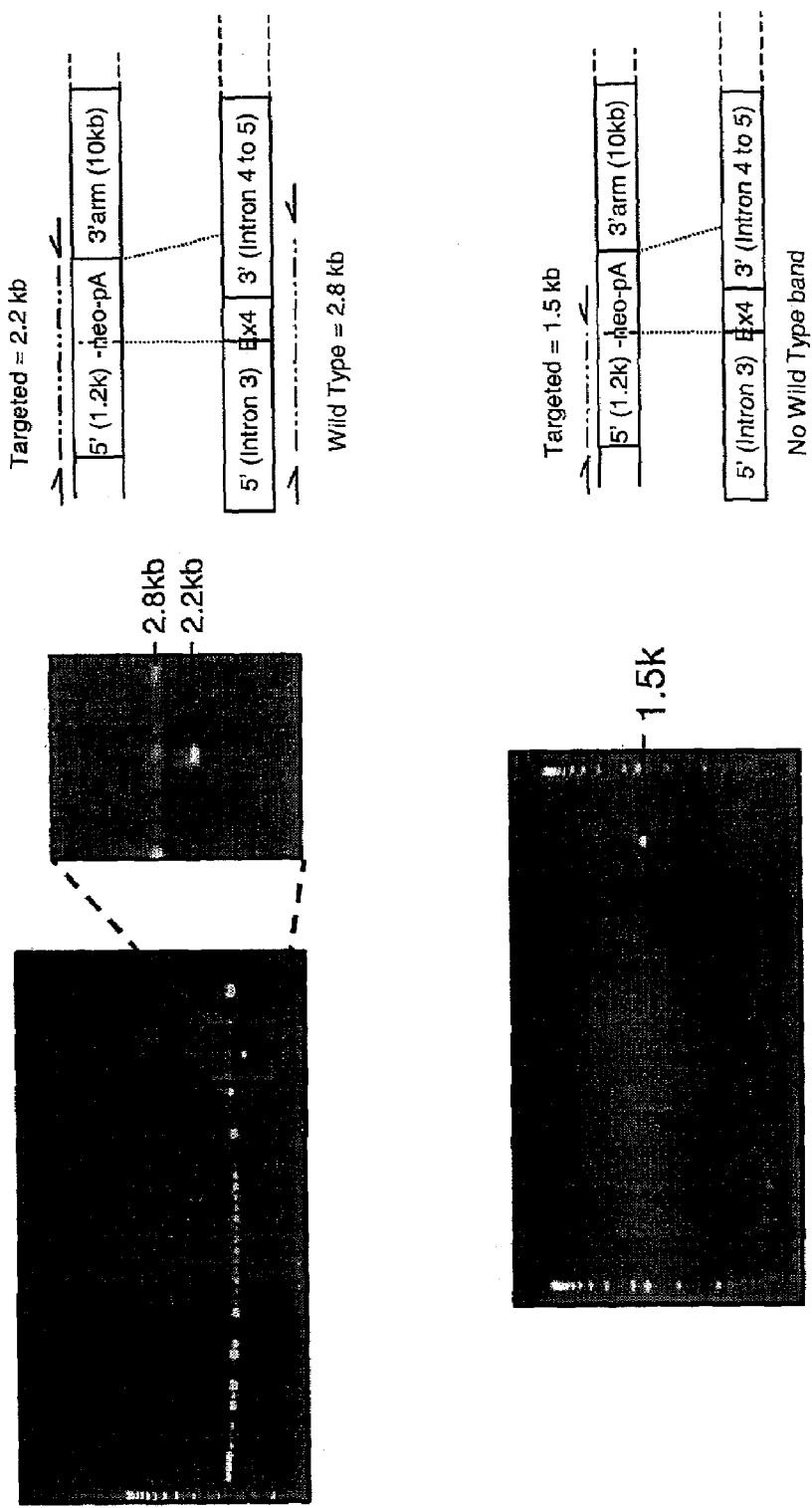

FIG. 3 shows the results of site specific recombination detected by PCR amplification. Wild type and targeted α1,3GT alleles were detected using sense (399010, 5'-CAGCTGTGTG GGTATGGGAG GG-3'; SEQ. ID NO:27) and antisense (499006, 5'-CTGAACTGAA TGTT-TATCCA GGCCATC-3'; SEQ. ID NO:28) PCR primers, yielding products of 2.8-kb and 2.2-kb, respectively. A second PCR screen with primers 399010 (SEQ. ID NO:29) and 399005 (5'-AGCCGATTGT CTGTTGTGCC CAGT-CAT-3'; SEQ. ID NO:30) produced a fragment of 1.5-kb only in clones that were correctly targeted. The frequency of site-specific recombination was 1 in 52 (6 in 312) clones in the 1 μg experiment or 1 in 88 (10 in 877) from all electroporations.

In parallel experiments, sheep fibroblasts were targeted with a vector designed to inactivate the prion protein (PrP) gene. This gene is heavily implicated in disease pathology of spongiform diseases such as scrapie, bovine spongiform encephalopathy, and Creutzfeldt-Jakob disease (CJD). The sheep PrP gene sequence is provided in Goldmann et al., Proc. Natl. Acad. Sci. USA 87:2476, 1990.

The frequency of site-specific recombination observed in these experiments is shown in Table 1:

TABLE 1

Gene Targeting Efficiency in Primary Sheep Fibroblast Cultures

| Parental culture | Target locus | Drug resistant colonies | Targeting events detected | Colonies suitable for nuclear transfer |
|---|---|---|---|---|
| Black Welsh | α1, 3GT | 877 | 10 (1.1%) | 0 (0%) |
| Black Welsh | PrP | 533 | 55 (10.3%) | 1 (0.2%) |
| Finn Dorset | α1, 3GT | 568 | 35 (6.2%) | 2 (0.4%) |

Nuclear transfer is typically conducted as follows. Oocytes are harvested from adult female breeding sheep treated with an analogue of gonadotrophin releasing hormone (Buserelin™, given 24 h after sponge removal). The oocytes are stripped of cumulus cells by triturating with a pipette and incubating with hyaluronidase. They are then enucleated by removing the first polar body and metaphase plate. A single targeted nuclear donor cell is introduced under the zona of each oocyte. The cell combination is subject to simultaneous electrofusion and activation (0.25 kV cm$^{-1}$ AC for 5 sec. to align oocyte and donor cell, followed by 3 pulses of 1.25 kV cm$^{-1}$ DC for 80 μsec to fuse and activate the reconstructed embryo). The activated cell is maintained in culture overnight at 39° C. Next day, the cells are embedded in agar chips to protect from macrophages, and then transferred to the ligated oviduct of a temporary recipient.

Estrous is controlled in the temporary recipient by treatment with intravaginal progestagen sponge for 11 to 16 days, with or without subcutaneous or intramuscular injection of 500 i.u. of PMSG. The timing brings the temporary recipients to estrus ~3 days before the oocyte donors. Cells are collected under general anesthesia using barbiturate followed by gaseous anesthetics. The reproductive tract is exposed by midventral laparotomy; placing ligatures of silk at each uterotubal junction, and embryos are transferred through the fimbriated end of the oviduct. The laparotomy is then closed, and a long-acting antibiotic is administered. The embryos are flushed from the temporary recipient after 6 days, and developing embryos are removed from the agar chip.

Blastocysts and morula are then transferred into the recipients that will carry the embryo to term. Estrus is controlled by treatment with an intravaginal progestagen sponge for 11 to 16 days, bringing the final recipients to estrus simultaneously with the oocyte donor. The permanent recipients are anesthetized by intravenous barbiturate and gaseous anesthetics, the reproductive tract is exposed by mid-ventral laparotomy, and the oviduct or uterus is temporarily cannulated for transfer of the embryos. Alternatively, three small puncture incisions are made anterior to the udder, and a laparoscope, manipulating forceps and needle are inserted for manipulation of the uterus. The oviduct or uterus is temporarily cannulated for transfer of the embryos, and the incision is sutured closed.

Recipients of oocytes with a targeted nucleus, engrafted in the manner outlined, were monitored for the status of their pregnancy by subcutaneous ultrasonic scanning on a weekly basis. For animals maintaining their pregnancy, the progress of the fetus is monitored regularly by ultrasound, and brought to term. Results are shown in Table 2. The longest-lived animal born with a PrP knockout survived 12 days.

TABLE 2

Nuclear Transfer from Gene Targeted Primary Cells

| | Nuclear donor cell | | |
|---|---|---|---|
| Stage of Animal Cloning | Parental Finn Dorset | α1, 3GT targeted | PrP targeted |
| Reconstructions | 126 | 142 | 454 |
| Morula and blastocyst | 33 | 21 | 43 |
| Fetuses at day 60 | 5 | 5 | 8 |
| Lambs at birth; live (dead) | 0 (2) | 0 | 3 (1) |
| Lambs alive at 1 week | 0 | 0 | 1 |

Example 3

Telomerizing Nuclear Donor Cells

A vector containing an expression cassette for telomerase reverse transcriptase was found to increase functional telomerase activity and replicative capacity in sheep fibroblasts suitable for nuclear transfer.

Figure 4:
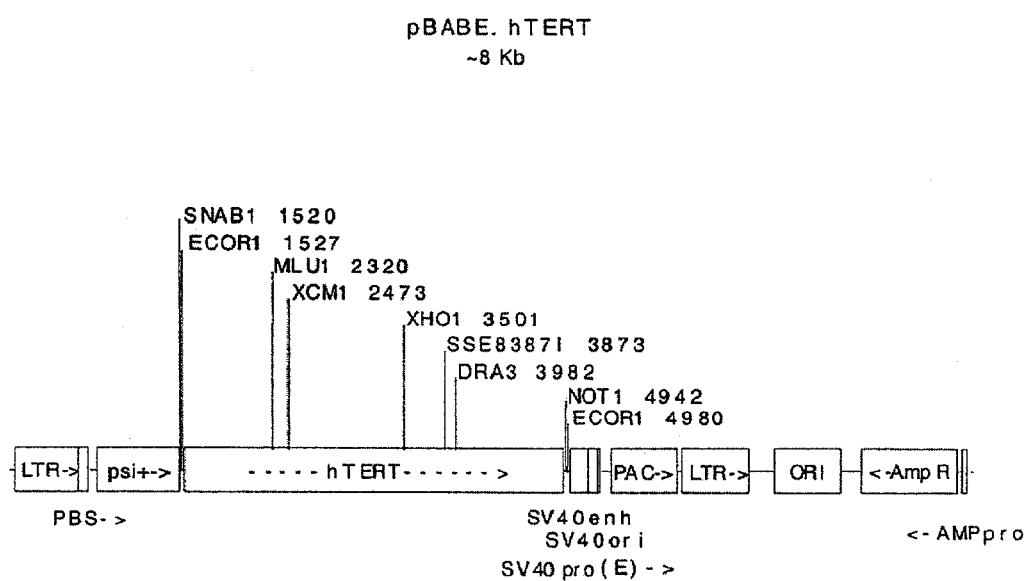
FIG. 4 is a map of plasmid pGRN145, which causes cells to express telomerase reverse transcriptase (abbreviated here as hTRT), the limiting component of telomerase activity in most mammalian cells. Transcription is under control of the myeloproliferative sarcoma virus (MPSV) promoter.

FIG. 4 is a map of plasmid pGRN145. It contains sequences encoding telomerase reverse transcriptase (abbreviated here as hTRT) with a consensus Kozak sequence downstream of the myeloproliferative sarcoma virus (MPSV) promoter. It also contains puromycin and hygromycin resistant gene sequences and allows drug selection of the transfected clones.

Primary sheep fibroblast cell line designated BW6F2 (passage 6, obtained from a Black Welsh sheep) was transfected with linearized pGRN145. The cells were plated in 96 well plates, and selected using puromycin at 1 μg/mL. PCR screening with puromycin primers showed that all but one of the selected clones contained the vector sequence.

Fourteen of the clones were developed into cell lines. hTERT expression was measured in the cloned sheep fibroblasts by Western blot and by immunocytology. Functional telomerase activity was measured by TRAP assay, and was found to be positive in 10 of these clones, compared with the original BW6F2 line.

In order to determine the replicative capacity of the cloned fibroblast cell lines, the cells were passaged continuously using standard culture conditions.

FIG. 5 shows the growth curves for these cells. Each line represents a single clone designation, except BW6F23, which is the parental (untransfected) line. The solid circles represent telomerase-expressing clones, and the solid triangles represent telomerase-negative clones. Open squares represent clones that were telomerase-negative initially, but became positive later. All telomerase-negative clones became senescent towards the end of the growth curve, as did the parental BW6F2 cells.

The clones expressing hTERT have been grown through at least 260 population doublings (PDs) and still grow like young cells. Cells transfected with a control plasmid without hTERT cDNA or the transfected cells not expressing hTERT grew less than 83 PDs. The parental cells only replicate through 127 PDs, when they become senescent.

The hTERT expressing sheep fibroblasts were also analyzed to determine whether or not the hTERT expressing cells showed signs of transformation to a malignant phenotype by karyotype analysis, response to serum starvation (0.1% serum for 7 days, followed by resynchronization for 24 h in 10% serum). Telomere length was assessed by extracting DNA from cloned cells using a blotting assay. The DNA was digested with RsaI and HinfI, separated on 0.7% agarose, blotted onto a nylon membrane, and probed with $^{32}$P-labeled (TTAGGG)$_3$ oligonucleotide.

It was found that by passage ~150, some clones have telomere shortening(GRN 1-1,2-7 and 2-8), while others show no change (GRN 2-1,2-5 and 2-10), or show elongated telomeres (GRN 2-2). Clones with higher hTERT expression levels (detected by Western blot and immunostaining with 1A4 antibody) maintained their telomere length, while clones with lower hTERT expression levels were typically the ones showing shortened telomeres.

A summary of results from these experiments is shown in Table 3.

Example 4

Vectors for Substituting the Galactose Transferase Gene with Fucosyltransferase

Vectors for substituting the encoding sequence for α1,2FT into the α1,3GT behind the endogenous promoter have been made by modifying the knockout vectors for neo (p0054) and puro (p0063).

FIG. 6, Top Panel, shows a map of the sheep α1,2FT substitution vector. A 1 kb RV-RI fragment was cloned into KpnI-RI cleaved modified pBS (pBluescript™, Stratagene), hence destroying the original RV site as follows. The 5' arm (gal)-FT fusion, which lacks a polyA site, was produced by PCR. The 5' arm was amplified with primers 199001 (5'-ACGTGGCTCCA AGAATTCTCCA GGCAAGAGTAC TGG-3', SEQ. ID NO:18) and 700001 (5'-CTG ACG ATG GCT CCG GAG CCA CAT TAT TTT CTC CTG GGA AAA GAA AAG-3', SEQ. ID NO:31), the latter having complementarity to human α1,2FT.

The human α1,2FT sequence (GenBank accession NM000148, SEQ. ID NO:9) was amplified from mRNA prepared from the 293 cell line (a permanent line of primary human embryonal kidney transformed by human adenovirus type 5 DNA; ATCC Accession No. CRL-1573). The following primers were used: 700002 (5'-ATA ATG TGG CTC CGG AGC CAT CGT CA-3'; SEQ. ID NO:32) and 700003 (5'-AAA GGA TCC TCA AGG CTT AGC CAA TGT CCA GAG T-3'; SEQ. ID NO:33). The products of 0.3 kb and 1.1 kb, respectively, were mixed in a PCR reaction in which they primed from each other to give a 1.4 kb fragment that was cloned into RI-BHI cut vector from above. This fusion has been sequenced and is correct.

TABLE 3

Characteristics of Telomerized Sheep Fibroblast Clones

| Designation | PCR for puromycin gene | TRAP assay (telomerase activity) | Population doublings observed | Response to serum starvation | Contact inhibition | Karyotype |
|---|---|---|---|---|---|---|
| GRN 1-1 | + | − | 354 | Normal (p54–56) | Normal (p72) | Normal (p14, p49) |
| GRN 1-2 | + | − → + | 289 | Normal (p50) | Normal (p47) | Normal (p8, p35) |
| GRN 2-1 | + | + | 264 | Normal (p50) | Normal (p43) | Normal (p13, p80) |
| GRN 2-2 | + | − → + | 294 | Normal (p48) | Normal (p52) | Normal (p30) Abnormal (p90) |
| GRN 2-3 | + | − | 37[a] | n.d. | n.d. | n.d. |
| GRN 2-4 | + | − | 75[a] | n.d. | n.d. | n.d. |
| GRN 2-5 | + | + | 279 | Normal (p54) | Normal (p46) | Normal (p12, p86) |
| GRN 2-7 | + | + | 314 | Normal (p62) | Normal (p64) | Normal (p15, p97) |
| GRN 2-8 | + | + | 318 | Normal (p60) | Normal (p52–53) | Normal (p15) |
| GRN 2-10 | + | + | 166[b] | n.d. | n.d. | Abnormal (p13) |
| GRN 2-12 | + | + | 293 | Normal (p50) | Normal (p51–53) | n.d. |
| GRN 2-13 | + | + | 258 | Normal (p47) | Normal (p48–49) | Normal (p16) |
| GRN 2-18 | − | − | 83[a] | Abnormal (p18) | n.d. | n.d. |
| GRN 2-20 | + | − → ? | 113[b] | n.d. | n.d. | n.d. |

[a]Cells became senescent
[b]Growth curve stopped

A fragment containing the SV40 poly A site, produced from synthetic oligos (700004, 5'-GAT CCG GGG ATC GGC AAT AAA AAG ACA GAA TAA AAC GCA CGG GTG TTG GGT CGT TTG TTC CTC GAG GTC GAC GAT-3', SEQ. ID NO:34; 700005, 5'-ATC GTC GAC CTC GAG GAA CAA ACG ACC CAA CAC CCG TGC GTT TTA TTC TGT CTT TTT ATT GCC GAT CCC CG -3', SEQ. ID NO:35), was ligated 3' of the FT coding sequence between BHI and RV sites. Finally, to complete the 3' arm of the vector, two separate fragments (a ~7 kb RV-NotI then a 2.4 kb RV) were added. The vector was designated p0090.

FIG. 6 also shows construction of a pig promoterless α1,2FT substitution vector. The middle panel of the figure shows pPAGTarget1, a vector comprising porcine α1,3GT sequence for inactivating α1,3GT in pig cells. The vector is digested with StuI/NsiI to release a small amount of 5 and 3' α1,3GT sequence, and also the neopA cassette. The NsiI site is blunt ended with DNA polymerase. A PCR fragment fusing 5' pig α1,3GT with α1,2FT-polyA is then made. Oligonucleotides galF (CCTATGCAAA TTAAGGTAG AACGCAC, SEQ. ID NO:36) and galR (5'-CTGAC-GATGG CTCCGGAGCC ACATTATTTT CTCCTGGGA AAAGAAAAG-3', SEQ. ID NO:37), with part of the latter being complementary to the α1,2FT sequence, produce a 200 bp fragment. Oligonucleotides FTF (5'-ATAATGTGG CTCCGGAGC CATCGTCA-3', SEQ. ID NO:38) and FTR (5'-CTCGAGGAA CAAACGACCC AACACCCGTG-3', SEQ. ID NO:39), directed to SV40 poly-A, produce a 1.2 kb α1,2FT poly-A fragment.

These fragments are fused by PCR, polished with T4 DNA polymerase, 5' phosphorylated, and ligated into the StuI/NsiI polished vector, to produce the targeting vector shown at the bottom of FIG. 5. The vector is linearized with NotI or SalI when used for targeting.

Example 5

α1,2FT Gene Expression in Telomerized Fibroblasts

Primary Black Welsh fibroblasts (designation BW6F2) were transfected with the hTERT gene as described in Example 3. The characteristics of telomerized clone GRN1.1 are described in Example 3.

GRN1.1 cells at passage 5 or 25 were resuscitated into T175 flasks and grown to subconfluency. Cells ($2.8 \times 10^6$, passage 5; $8.3 \times 10^6$, passage 25) were electroporated with 10 μg of NotI linearized p0054 targeting vector, using a setting of 125 μF: 350 V in Flowgen™ 0.4 cm /800 μl cuvettes. Diluted cells were plated to 20×96 well plates. The next day, G418 (600 μg /mL) as added to the medium to begin the selection process. Cell death appeared after 8–10 days in G418, much longer than when using parental BW6F2 cells. Colonies were observed after ~2 weeks and replica plated (41 colonies from passage 5 cells; 2 colonies from passage 25 cells) on day 20 of selection.

PCR analysis was conducted on DNA isolated from selected colonies. One correct targeting event (clone B9) was detected from the passage 5 electroporation. This clone and eight non-targeted clones were resuscitated in 24 well plates. All clones grew to confluency. The B9 (correctly targeted) cell line, and the C9 cell line (one of the eight containing randomly integrated α1,3GT) grew fastest. Clones B9 and C9 have been karyotyped, and both are 54XY.

Thus, telomerized sheep fibroblasts were successfully targeted with the promoterless neo α1,3GT targeting vector, p0054. The targeted clone (B9) has been expanded, and retains a stable karyotype. This clone exists as a pure population of targeted cells and continues to grow at passage 17 (~80 doublings). Successfully targeted clones can be used for replacing the α1,3GT gene on the other allele with α1,2FT, using the targeting vectors obtained in Example 4.

To ensure that the α1,2FT encoding sequence in the fusion vector produces functional enzyme, the α1,2FT sequence was PCR'ed and subcloned between the NheI and BamHI sites of pEGFP-C1 (ClonTech), thereby replacing the GFP sequence in the vector to form a pCMV-α1,2FT-pA cassette. This plasmid was designated p105. The vector was transfected into the B9 and C9 telomerized α1,3GT-targeted lines by lipofection. After 48 h, the cells were washed in PBS and fixed in cold acetone for 10 min at 4° C. Samples were washed in Hepes buffer (0.15 M NaCl, 0.01 M Hepes, pH 7.5) and incubated with UEA-1 rhodamine (Vector Labs) diluted 1:50 in Hepes buffer. After washing in Hepes buffer, the samples were mounted in DAPI containing Vector Shield™.

FIG. 7 shows the results. Normally, sheep fibroblasts do not stain with the UEA-1 lectin, since they do not bear H substance. Staining of human 293 cells is shown here as a positive control. As a result of transfection, both the B9 and C9 sheep cell lines now specifically bind UEA-1, showing that expression of the human α1,2FT gene in sheep fibroblasts does indeed cause synthesis of H substance carbohydrate on the cell surface.

The compositions and procedures provided in the description can be effectively modified by those skilled in the art without departing from the spirit of the invention embodied in the claims that follow.

TABLE 4

Sequences listed in this Disclosure

| SEQ. ID NO: | Designation | Reference |
|---|---|---|
| 1 | Human Telomerase Reverse Transcriptase cDNA sequence | GenBank Accession NM 003219<br>U.S. Patent 6,166,178 |
| 2 | Human Telomerase Reverse Transcriptase amino acid sequence | GenBank Accession NM 003219<br>U.S. Patent 6,166,178 |
| 3 | Sheep α1,3GT cDNA sequence | This Disclosure. |
| 4 | Sheep α1,3GT amino acid sequence | This Disclosure. |
| 5 | Bovine α1,3GT cDNA sequence | GenBank Accession J04989<br>Joziasse et al. "Bovine α1->3-galactosyltransferase" J. Biol. Chem. 264, 14290 (1989) |

TABLE 4-continued

Sequences listed in this Disclosure

| SEQ. ID NO: | Designation | Reference |
|---|---|---|
| 6 | Bovine α1,3GT amino acid sequence | GenBank Accession P14769<br>Joziasse et al. (1989), supra. |
| 7 | Pig α1,3GT cDNA sequence | GenBank Accession L36152<br>Sus scrofa alpha-1,3-galactosyltransferase mRNA.<br>Strahan et al. "cDNA sequence and chromosome localization of pig α1,3 galactosyltransferase" Immunogenetics 41, 101 (1995)<br>See also GenBank Accession L36535<br>Sandrin et al. "Characterization of cDNA clones for porcine a(1,3)galactosyltransferase" Xenotransplantation (1994) |
| 8 | Pig α1,3GT amino acid sequence | GenBank Accession L36152<br>Strahan et al., supra. |
| 9 | Human α1,2FT (FUT1) cDNA sequence | Larsen, et al. "Molecular cloning, sequence, and expression of a human GDP-L-fucose:beta-D-galactoside 2-alpha-L-fucosyltransferase cDNA that can form the H blood group antigen" Proc. Natl. Acad. Sci. USA 87,6674 (1990)<br>GenBank Accession NM 000148 |
| 10 | Human α1,2FT (FUT1) amino acid sequence | Larsen, et al., supra.<br>GenBank Accession NM 000148 |
| 11 | Human Fuc-α1,2Gal-α1,3GalNAc (Blood Group A) transferase cDNA sequence | Yamamoto, et al. "Cloning and characterization of DNA complementary to human UDP-GalNAc: Fuc-α1,2Gal-α1,3GalNAc transferase" J. Biol. Chem. 265:1146–1151 (1989)<br>GenBank Accession J05175 |
| 12 | Human Blood Group A-transferase amino acid sequence | Yamamoto, et al., supra.<br>GenBank Accession J05175 |
| 13 | Human Fuc-α1,2Gal-α1,3Gal (Blood Group B) transferase cDNA sequence | Yamamoto. "*Homo sapiens*B-specific alpha 1->3 galactosyltransferase (ABO) mRNA, ABO-*B101 allele, complete cds." (direct submission)<br>GenBank Accession AF134414 |
| 14 | Human Blood Group B-transferase amino acid sequence | Yamamoto, supra.<br>GenBank Accession AF134414 |
| 15 to 40 | Probes and PCR primers | This Invention. |

```
gcagcgctgc gtcctgctgc gcacgtggga agccctggcc ccggccaccc ccgcgatgcc     SEQ. ID NO:1 gcgcgctccc cgctgccgag ccgtgcgctc cctgctgcgc agccactacc gcgaggtgct gccgctggcc acgttcgtgc ggcgcctggg gccccagggc tggcggctgg tgcagcgcgg ggacccggcg gctttccgcg cgctggtggc ccagtgcctg gtgtgcgtgc cctgggacgc acggccgccc cccgccgccc cctccttccg ccaggtgtcc tgcctgaagg agctggtggc ccgagtgctg cagaggctgt gcgagcgcgg cgcgaagaac gtgctggcct tcggcttcgc gctgctggac ggggcccgcg ggggcccccc cgaggccttc accaccagcg tgcgcagcta cctgcccaac acggtgaccg acgcactgcg ggggagcggg gcgtgggggc tgctgctgcg ccgcgtgggc gacgacgtgc tggttcacct gctggcacgc tgcgcgctct ttgtgctggt ggctcccagc tgcgcctacc aggtgtgcgg gccgccgctg taccagctcg cgctgccac tcaggcccgg cccccgccac acgctagtgg accccgaagg cgtctgggat gcgaacgggc ctggaaccat agcgtcaggg aggccggggt ccccctgggc ctgccagccc cgggtgcgag gaggcgcggg ggcagtgcca gccgaagtct gccgttgccc aagaggccca ggcgtggcgc tgcccctgag ccggagcgga cgcccgttgg gcaggggtcc tgggcccacc cgggcaggac gcgtggaccg agtgaccgtg gtttctgtgt ggtgtcacct gccagacccg ccgaagaagc cacctctttg gagggtgcgc tctctggcac gcgccactcc cacccatccg tgggccgcca gcaccacgcg ggccccccat ccacatcgcg gccaccacgt ccctgggaca cgccttgtcc
```

```
cccggtgtac gccgagacca agcacttcct ctactcctca ggcgacaagg agcagctgcg gccctccttc ctactcagct ctctgaggcc cagcctgact ggcgctcgga ggctcgtgga gaccatcttt ctgggttcca ggccctggat gccagggact ccccgcaggt tgccccgcct gccccagcgc tactggcaaa tgcggcccct gtttctggag ctgcttggga accacgcgca gtgcccctac ggggtgctcc tcaagacgca ctgcccgctg cgagctgcgg tcacccagc agccggtgtc tgtgcccggg agaagcccca gggctctgtg gcggccccg aggaggagga cacagacccc cgtcgcctgg tgcagctgct ccgccagcac agcagcccct ggcaggtgta cggcttcgtg cgggcctgcc tgcgccggct ggtgccccca ggcctctggg ctccaggca caacgaacgc cgcttcctca ggaacaccaa gaagttcatc tccctgggga agcatgccaa gctctcgctg caggagctga cgtggaagat gagcgtgcgg gactgcgctt ggctgcgcag gagcccaggg gttggctgtg ttccggccgc agagcaccgt ctgcgtgagg agatcctggc caagttcctg cactggctga tgagtgtgta cgtcgtcgag ctgctcaggt ctttcttta tgtcacggag accacgtttc aaaagaacag gctcttttc taccggaaga gtgtctggag caagttgcaa agcattggaa tcagacagca cttgaagagg gtgcagctgc gggagctgtc ggaagcagag gtcaggcagc atcgggaagc caggcccgcc ctgctgacgt ccagactccg cttcatcccc aagcctgacg ggctgcggcc gattgtgaac atggactacg tcgtgggagc cagaacgttc cgcagagaaa agagggccga gcgtctcacc tcgagggtga aggcactgtt cagcgtgctc aactacgagc gggcgcggcg ccccggcctc ctgggcgcct ctgtgctggg cctggacgat atccacaggg cctggcgcac cttcgtgctg cgtgtgcggg cccaggaccc gccgcctgag ctgtactttg tcaaggtgga tgtgacgggc gcgtacgaca ccatccccca ggacaggctc acggaggtca tcgccagcat catcaaaccc cagaacacgt actgcgtgcg tcggtatgcc gtggtccaga aggccgccca tgggcacgtc cgcaaggcct tcaagagcca cgtctctacc ttgacagacc tccagccgta catgcgacag ttcgtggctc acctgcagga gaccagcccg ctgagggatg ccgtcgtcat cgagcagagc tcctccctga atgaggccag cagtggcctc ttcgacgtct tcctacgctt catgtgccac cacgccgtgc gcatcagggg caagtcctac gtccagtgcc agggatccc gcagggctcc atcctctcca cgctgctctg cagcctgtgc tacggcgaca tggagaacaa gctgtttgcg gggattcggc gggacgggct gctcctgcgt ttggtggatg atttcttgtt ggtgacacct cacctcaccc acgcgaaaac cttcctcagg accctggtcc gaggtgtccc tgagtatggc tgcgtggtga acttgcggaa gacagtggtg aacttccctg tagaagacga ggccctgggt ggcacggctt tgttcagat gccggcccac ggcctattcc cctggtgcgg cctgctgctg gataccgga ccctggaggt gcagagcgac tactccagct atgcccggac ctccatcaga gccagtctca ccttcaaccg cggcttcaag gctgggagga acatgcgtcg caaactcttt ggggtcttgc ggctgaagtg tcacagcctg tttctggatt tgcaggtgaa cagcctccag acggtgtgca ccaacatcta caagatcctc ctgctgcagg cgtacaggtt tcacgcatgt gtgctgcagc tcccatttca tcagcaagtt tggaagaacc ccacattttt cctgcgcgtc atctctgaca cggcctccct ctgctactcc atcctgaaag ccaagaacgc agggatgtcg ctgggggcca agggcgccgc cggccctctg ccctccgagg ccgtgcagtg gctgtgccac caagcattcc tgctcaagct gactcgacac cgtgtcacct acgtgccact cctggggtca ctcaggacag cccagacgca gctgagtcgg aagctcccgg ggacgacgct gactgccctg gaggccgcag ccaacccggc
```

```
actgccctca gacttcaaga ccatcctgga ctgatggcca cccgcccaca gccaggccga gagcagacac cagcagccct gtcacgccgg gctctacgtc ccagggaggg aggggcggcc cacacccagg cccgcaccgc tgggagtctg aggcctgagt gagtgtttgg ccgaggcctg catgtccggc tgaaggctga gtgtccggct gaggcctgag cgagtgtcca gccaagggct gagtgtccag cacacctgcc gtcttcactt ccccacaggc tggcgctcgg ctccacccca gggccagctt ttcctcacca ggagcccggc ttccactccc cacataggaa tagtccatcc ccagattcgc cattgttcac ccctcgccct gccctccttt gccttccacc cccaccatcc aggtggagac cctgagaagg accctgggag ctctgggaat ttggagtgac caaaggtgtg ccctgtacac aggcgaggac cctgcacctg gatggggtc cctgtgggtc aaattggggg gaggtgctgt gggagtaaaa tactgaatat atgagttttt cagttttgaa aaaaa
```

MPRAPRGRAVRSLLRSHYREVLPLATFVRRLGPQGWRLVQRGDP  SEQ. ID NO:2

AAFRALVAQCLVGVPWDARPPPAAPSFRQVSCLKELVARVLQRLCERGAKNVLAFGFA

LLDGARGGPPEAFTTSVRSYLPNTVTDALRGSGAWGLLLRRVGDDVLVHLLARCALFV

LVAPSCAYQVGGPPLYQLGAATQARPPPHASGPRRRLGCERAWNHSVREAGVPLGLPA

PGARRRGGSASRSLPLPKRPRRGAAPEPERIPVGQGSWAHPGRTRGPSDRGFCVVSPA

RPAEEAISLEQALSGTRHSHPSVGRQhHAGPPSTSRPPRPWDIPCPPVYAEIKHFLYS

SGDKEQLRPSFLLSSLRPSLTGARRLVETIFLGSRPWMPGTPRRLPRLPQRYWQMRPL

FLELLGNHAQCPYGVLLKTHCPLRAAVTPAAGVCAREKPQGSVAAPEEEDTDPRRLVQ

LLRQHSSPWQVYGFVRACLRRLVPPGLWGSRHNERRFLRNTKKFISLGKHAKLSLQEL

TWKMSVRDGAWLRRSPGVGCVPAAEHRLREEILAKFLHWLMSVYVVELLRSFFYVTET

TFQKNRLFFYRKSVWSKLQSIGIRQHLKRVQLRELSEAEVRQHREARPALLTSRLRFI

PKPDGLRPIVNMDYVVGARTFRREKRAERLTSRVKALFSVLNYERARRPGLLGASVLG

LDDIHRAWRTFVLRVRAQDPPPELYFVKVDVTGAYDTJPQDRLTEVIASIIKPQNTYC

VRRYAVVQKAAHGHVRKAFKSIIVSTLTDLQPYMRQFVAHLQETSPLRDAVVIEQSSSL

NEASSGLFDVFLRFMCHHAVRIRGKSYVQGQGIPQGSILSTLLGSLGYGDMENKLFAG

IRRDGLLLRLVDDFLLVTPHLIHAKTFLRTLVRGVPEYGCVVNLRKTVVNFPVEDEAL

GGTAFVQMPAHGLFPWCGLLLDTRTLEVQSDYSSYARTSIRASLTFNRGFKAGRNMRR

KLFGVLRLKCHSLFLDLQVNSLQTVCTNIYKILLLQAYRFHACVLQLPFHQQVWKNPT

FFLRVISDTASLCYSILKAKNAGMSLGAKGAAGPLPSEAVQWLCHQAFLLKLTRHRVT

YVPLLGSLRTAQTQLSRKLPGTTLTALEAAANPALPSDFKTILD

AGCCGAGGACGCCGCCGGGAGCCGAGGCTCCGGCCAGCCCCCAGCGCGCCCAGCTTCTG  SEQ. ID NO:3

CAGATCAGG

AGTCAGAACGCTGCAC

CTTCGCTTCCTCCCAGCCCTGCCTCCTTCTGCAAAACGGAGCTCAATAGAACTTGGTACT

TTTGCCTTTTACTCTGGGAGGAGAGAAGCAGACGATGAGGAGAAAATA

[beginning of coding sequence]
ATGAATGTCAAA

GGAAAAGTGATTCTGTCAATGCTGGTTGTCTCAACTGTCATTGTTGTGTTTTGGGAATAT

ATCCACAGCCCAGAAGGCTCTTTGTTCTGGATAAACCCATCAAGAAACCCAGAAGTCAGT

GGCGGCAGCAGCATTCAGAAGGGCTGGTGGTTTCCGAGATGGTTTAACAATGGTTACCAA

-continued

```
GAAGAAGATGAAGACGTAGACGAAGAAAAGGAACAAAGAAAGGAAGACAAAAGCAAGCTT
AAGCTATCGGACTGGTTCAACCCATTTAAACGCCCTGAGGTTGTGACTATGACAGATTGG
AAGGCACCCGTGGTGTGGGAAGGCACTTACAACAGAGCCGTCTTAGACGATTACTACGCC
AAGCAGAAAATTACCGTCGGCCTGACGGTTTTCGCCGTCGGAAGATACATTGAGCATTAC
TTGGAGGAGTTCTTAACGTCTGCTAATAAGCACTTCATGGTTGGCCACCGAGTCATCTTT
TACGTCATGGTGGACGACGTCTCCAGGATGCCTTTGATAGAGCTGGGCCCTCTGCGCTCC
TTCAAAGTGTTTGAGGTCAAGCCTGAGAGGAGGTGGCAGGACGTCAGCATGGTGCGCATG
AAGACCATCGGGGAGCACATCGTGGCCCACATCCAGCGTGAGGTTGACTTCCTCTTCTGC
ATGGACGTGGACCAGGTCTTCCAAGACGAGTTCGGGGTGGAGACCCTGGGTGAGTCGGTG
GCCCAGCTACAGGCCTGGTGGTACAAGGCAGATCCCGATGAGTTTACCTACGAGAGGCGC
AAGGAGTCTGCAGCATACATTCCCTTCGGCGAAGGGGATTTTTATTACCACGCAGCCATT
TTTGGGGGAACACCCACTCAGGTCCTTAACATCACCCAGGAATGCTTCAAAGGAATCCTC
AAGGACAAGAAAAATGACATAGAAGCCCAATGGCATGATGAGAGCCATCTAAACAAGTAT
TTCCTTCTCAACAAACCCACTAAAATCTTATCCCCGGAATACTGCTGGGATTATCATATA
GGCCTACCTGCGGATATTAAGCTTGTCAAGATGTCTTGGCAGACAAAAGAGTATAATGTG
GTTAGAAATAACGTCTGA
[end of coding sequence]
```

```
MNVKGKVILS MLVVSTVIVV FWEYIHSPEG SLFWINPSRN PEVSGGSSIQ       SEQ. ID NO:4
KGWWFPRWFN NGYQEEDEDV DEEKEORKED KSKLKLSDWF NPFKRPEVVT
MTDWKAPVVW EGTYNRAVLD DYYAKQKITV GLTVFAVGRY JEHYLEFELT
SANKHFMVGH RVIFYVMVDD VSRMPLIELG PLRSFKVFEV KPERRWQDVS
MVRMKTIGEH IVAHIQREVD FLFCMDVDQV FQDEFGVETL GESVAQLQAW
WYKADPDEFT YERRKESAAY IPFGEGDFYY HAAIFGGTPT QVLNIIQECF
KGILKDKKND IEAQWHDESH LNKYFLLNKP TKILSPEYCW DYHIGLPADI
KLVKMSWQTK EYNVVRNNV*
```

```
CCGGGGGCCGGGCCGAGCTGGGAGCGTCGAGCCCGCTGCCCAGCGCCCGCCGGCTCCCTC    SEQ. ID NO:5
GCGCCCCTGCCCGCCGCCCCGGAGGAGCGCCCGGCGGCCGGCCGACGGGAGCGCAGCGGC
ACACCCCGCCCCGGCACGCCCGCGGGGCTCGGGAGGAGGCAGCGCGCCGACTGTTCCGGC
AGCCGAGGACGCCGCCGGGGAGCCGAGGCGCCGGCCAGCCCCCAGCGCGCCCAGCTTCTG
CGGATCAGGGAAACCACGTGTCCTCAAGTGGCCAGCCAGCTGTCCCCAAGAGGAACTTGC
CTGGCATTTGCACGGAAAGACGAGACACTTCACAAAATCAACGGAGTCAGAAGGCTGCAC
CTTCGCTTCCTCCCAGCCCTGCCTCCTTCTGCAGAACGGAGCTCAGTAGAACTTGGTACT
TTTGCCTTTTACTCTAGGAGGAGAGAAGCAGACGATGAGGAGAAAATAATGAATGTCAAA
GGAAAAGTGATTCTGTCAATGCTGGTTGTCTCAACTGTCATTGTTGTGTTTTGGGAATAT
ATCCACAGCCCAGAAGGCTCTTTGTTCTGGATAAACCCATCAAGAAACCCAGAAGTT
GGTGGCAGCAGCATTCAGAAGGGCTGGTGGCTTCCGAGATGGTTTAACAATGGTTACCAT
GAAGAAGATGGAGACATAAACGAAGAAAAGGAACAAAGAAACGAAGACGAAAGCAAGCTT
AAGCTATCGGACTGGTTCAACCCATTTAAACGCCCCGAGGTTGTGACCATGACGAAGTGG
AAGGCTCCAGTGGTGTGGGAAGGCACTTACAACAGAGCCGTCTTAGACAATTATTATGCC
AAGCAGAAAATTACCGTCGGCCTGACGGTTTTCGCCGTCGGAAGATACATTGAGCATTAC
TTGGAGGAGTTCTTAACGTCTGCTAATAAGCACTTCATGGTGGGCCACCCAGTCATCTTT
```

-continued

```
TATATCATGGTAGATGATGTCTCCAGGATGCCTTTGATAGAGTTGGGTCCTCTGCGCTCC
TTCAAAGTGTTTAAGATCAAGCCTGAGAAGAGGTGGCAGGACATCAGCATGATGCGCATG
AAGACTATCGGGGAGCACATTGTGGCCCACATCCAGCATGAGGTTGACTTCCTTTTCTGC
ATGGATGTGGACCAGGTCTTCCAAGACAAGTTTGGGGTGGAGACCCTGGGCGAGTCGGTG
GCCCAGCTACAAGCCTGGTGGTACAAGGCAGATCCCAATGACTTCACCTACGAGAGGCGG
AAGGAGTCTGCAGCATACATTCCCTTCGGCGAAGGGGATTTTTATTACCATGCAGCCATT
TTTGGGGGAACACCCACTCAGGTCCTTAACATCACCCAGGAATGCTTCAAAGGAATCCTC
AAGGACAAGAAAAATGACATAGAAGCCCAATGGCATGATGAAAGCCATCTAAACAAGTAT
TTCCTTCTCAACAAACCTACTAAAATCTTATCCCCGGAATACTGCTGGGATTATCACATA
GGCCTACCTGCGGATATTAAGCTTGTCAAGATGTCTTGGCAGACAAAAGAGTATAATGTG
GTTAGAAATAATGTCIGACTTTGTGCCAGTACATTTCTGAATTTGAGAGAGTATTATTCT
```

MNVKGKVILS MLVVSTVIVV FWEYIHSPEG SLFWINPSRN PEV.GGSSIQ        SEQ. ID NO:6
KGWWLPRWFN NGYHEEDGDI NEEKEQRNED ESKLKLSDWF NPFKRPEVVT
MTKWKAPVVW EGTYNRAVLD NYYAKQKITV GLTVFAVGRY IEHYLEEFLT
SANKHFMVGH PVIFYIMVDD VSRMPLIELG PLRSFKVFKI KPEKRWQDIS
MMRMKTJGEH IVAHIQHEVD FLFCMDVDQV FQDKFGVETL GESVAQLQAW
WYKADPNDFT YERRKESAAY IPFGEGDFYY HAAIFGGTPT QVLNITQECF
KGILKDKKND IEAQWHDESH LNKYFLLNKP TKILSPEYCW DYHIGLPADI
KLVKMSWQTK EYNVVRNNV*

```
   1 catgaggaga aaataatgaa tgtcaaagga agagtggttc tgtcaatgct gcttgtctca   SEQ. ID NO:7
  61 actgtaatgg ttgtgttttg ggaatacatc aacagcccag aaggttcttt gttctggata
 121 taccagtcaa aaacccaga agttggcagc agtgctcaga ggggctggtg gtttccgagc
 181 tggtttaaca atgggactca cagttaccac gaagaagaag acgctatagg caacgaaaag
 241 gaacaaagaa aagaagacaa cagaggagag cttccgctag tggactggtt taatcctgag
 301 aaacgcccag aggtcgtgac cataaccaga tggaaggctc cagtggtatg ggaaggcact
 361 tacaacagag ccgtcttaga taattattat gccaaacaga aaattaccgt gggcttgacg
 421 gttttttgctg tcggaagata cattgagcat tacttggagg agttcttaat atctgcaaat
 481 acatacttca tggttggcca caaagtcatc ttttacatca tggtggatga tatctccagg
 541 atgcctttga tagagctggg tcctctgcgt tcctttaaag tgtttgagat caagtccgag
 601 aagaggtggc aagacatcag catgatgcgc atgaagacca tcgggagca tcctggcc
 661 cacatccagc acgaggtgga cttcctcttc tgcatggacg tggatcaggt cttccaaaac
 721 aactttgggg tggagaccct gggccagtcg gtggctcagc tacaggcctg gtggtacaag
 781 gcacatcctg acgagttcac ctacgagagg cggaaggagt ccgcagccta cattccgttt
 841 ggccaggggg attttttatta ccacgcagcc atttttgggg aacacccac tcaggttcta
 901 aacatcactc aggagtgctt caagggaatc ctccaggaca aggaaaatga catagaagcc
 961 gagtggcatg atgaaagcca tctaaacaag tatttccttc tcaacaaacc cactaaaatc
1021 ttatccccag aatactgctg ggattatcat ataggcatgt ctgtggatat taggattgtc
1081 aagatagctt ggcagaaaaa agagtataat ttggttagaa ataacatctg actttaaatt
1141 gtgccagcag tttctgaat ttgaaagagt attactctgg ctacttctcc agagaagtag
```

-continued

```
1201 cacttaattt taacttttaa aaaaatacta acaaaatacc aacacagtaa gtacatatta 1261 ttcttccctt
```

```
MNVKGRVVLSMLLVSTVMVVFWEYINSPEGSLFWIYQSKNPEVG                         SEQ. ID NO:8
SSAQRGWWFPSWFNNGTHSYHEEEDAIGNEKEQRKEONRGELPLVDWFNPEKRPEVVT
ITRWKAPVVWEGTYNRAVLQNYYAKQKITVGLTVFAVGRYIEHYLEEFLISANTYFMV
GHKVIFYIMVDDISRMPLIELGPLRSFKVFEIKSEKRWQDISMMRMKTIGEHILAHIQ
HEVDFLFCMDVDQVFQNNFGVETLGQSVAQLQAWWYKAHPDEFTYERRKESAAYIPFG
QGDFYYHAAIFGGTPTQVLNITQECFKGILQDKENDIEAEWHDESHLNKYFLLNKPTK
ILSPEYCWDYHIGMSVDIRIVKIAWQKKEYNLVRNNI
```

```
   1 gcctggcgtt ccaggggcgg ccggatgtgg cctgcctttg cggagggtgc gctccggcca    SEQ. ID NO:9
  61 cgaaaagcgg actgtggatc tgccacctgc aagcagctcg gccatgtggc tccggagcca
 121 tcgtcagctc tgcctggcct tcctgctagt ctgtgtcctc tctgtaatct tcttcctcca
 181 tatccatcaa gacagctttc acatggcct aggcctgtcg atcctgtgtc cagaccgccg
 241 cctggtgaca cccccagtgg ccatcttctg cctgccgggt actgcgatgg ccccaacgc
 301 ctcctcttcc tgtccccagc accctgcttc cctctccggc acctggactg tctaccccaa
 361 tggccggttt ggtaatcaga tgggacagta tgccacgctg ctggctctgg cccagctcaa
 421 cggccgccgg gcctttatcc tgcctgccat gcatgccgcc ctggcccgg tattccgcat
 481 caccctgccc gtgctggccc cagaagtgga cagccgcacg ccgtggcggg agctgcagct
 541 tcacgactgg atgtcggagg agtacgcgga cttgagagat cctttcctga agctctctgg
 601 cttcccctgc tcttggactt tcttccacca tctccgggaa cagatccgca gagagttcac
 661 cctgcacgac caccttcggg aagaggcgca gagtgtgctg ggtcagctcc gcctgggccg
 721 cacaggggac cgcccgcgca cctttgtcgg cgtccacgtg cgccgtgggg actatctgca
 781 ggttatgcct cagcgctgga agggtgtggt gggcgacagc gcctacctcc ggcaggccat
 841 ggactggttc cgggcacggc acgaagcccc cgttttcgtg gtcaccagca acggcatgga
 901 gtggtgtaaa gaaaacatcg acacctccca gggcgatgtg acgtttgctg gcgatggaca
 961 ggaggctaca ccgtggaaag actttgccct gctcacacag tgcaaccaca ccattatgac
1021 cattggcacc ttcggcttct gggctgccta cctggctggc ggagacactg tctacctggc
1081 caacttcacc ctgccagact ctgagttcct gaagatcttt aagccggagg cggccttcct
1141 gcccgagtgg gtgggcatta atgcagactt gtctccactc tggacattgg ctaagccttg
1201 agagccaggg agactttctg aagtagcctg atctttctag agccagcagt acgtggcttc
1261 agaggcctgc catcttctgg agaagcttgt ggtgttcctg aagcaaatgg gtgcccgtat
1321 ccagagtgat tctagttggg agagttggag agaagggga cgtttctgga actgtctgaa
1381 tattctagaa ctagcaaaac atcttttcct gatggctggc aggcagttct agaagccaca
1441 gtgcccacct gctcttccca gcccatatct acagtacttc cagatggctg cccccaggaa
1501 tggggaactc tccctctggt ctactctaga agaggggtta cttctcccct gggtcctcca
1561 aagactgaag gagcatatga ttgctccaga gcaagcattc accaagtccc cttctgtgtt
1621 tctggagtga ttctagaggg agacttgttc tagagaggac caggtttgat gcctgtgaag
1681 aaccctgcag ggcccttatg gacaggatgg ggttctggaa atccagataa ctaaggtgaa
1741 gaatcttttt agttttttttt tttttttttt ggagacaggg tctcgctctg ttgcccaggc
1801 tggagtgcag tggcgtgatc ttggctcact gcaacttccg cctcctgtgt tcaagcgatt
```

-continued

```
1861 ctcctgtctc agcctcctga gtagatggga ctacaggcac aggccattat gcctggctaa
1921 tttttgtatt tttagtagag acagggtttc accatgttgg ccgggatggt ctcgatctcc
1981 tgaccttgtc atccacctgt cttggcctcc caaagtgctg ggattactgg catgagccac
2041 tgtgcccagc ccggatattt ttttttaatt atttatttat ttatttattt attgagacgg
2101 agtcttgctc tgtagcccag gccagagtgc agtggcgcga tctcagctca ctgcaagctc
2161 tgcctcccgg gttcatgcca ttctgcctca gcctcctgag tagctgggac tacaggcgcc
2221 cgccaccacg cccggctaat ttttttttgta ttttagtag agacggggtt tcatcgtgtt
2281 aaccaggatg gtctcgatct cctgacctcg tgatctgccc acctcggcct cccacagtgc
2341 tgggattacc ggcgtgagcc accatgcctg gcccggataa tttttttttaa tttttgtaga
2401 gacgaggtct tgtgatattg cccaggctgt cttcaactc ctgggctcaa gcagtcctcc
2461 caccttggcc tcccagaatg ctgggtttat agatgtgagc cagcacaccg gccaagtga
2521 agaatctaat gaatgtgcaa cctaattgta gcatctaatg aatgttccac cattgctgga
2581 aaaattgaga tggaaaacaa accatctcta gttggccagc gtcttgctct gttcacagtc
2641 tctggaaaag ctggggtagt tggtgagcag agcgggactc tgtccaacaa gccccacagc
2701 ccctcaaaga cttttttttg tttgttttga gcagacaggc taaaatgtga acgtggggtg
2761 agggatcact gccaaaatgg tacagcttct ggagcagaac tttccaggga tccagggaca
2821 cttttttttta aagctcataa actgccaaga gctccatata ttgggtgtga gttcaggttg
2881 cctctcacaa tgaaggaagt tggtctttgt ctgcaggtgg gctgctgagg gtctgggatc
2941 tgttttctgg aagtgtgcag gtataaacac accctctgtg cttgtgacaa actggcaggt
3001 accgtgctca ttgctaacca ctgtctgtcc ctgaactccc agaaccacta catctggctt
3061 tgggcaggtc tgagataaaa cgatctaaag gtaggcagac cctggaccca gcctcagatc
3121 caggcaggag cacgaggtct ggccaaggtg acggggttg tcgagatctc aggagcccct
3181 tgctgttttt tggagggtga agaagaaac cttaaacata gtcagctctg atcacatcCC
3241 ctgtctactc atccagaccc catgcctgta ggcttatcag ggagttacag ttacaattgt
3301 tacagtactg ttcccaactc agctgccacg ggtgagagag caggaggtat gaattaaaag
3361 tctacagcac taa
```

MWLRSHRQLCLAFLLVGVLSVIFFLHIHQDSFPHGLGLSILCPD  SEQ.ID NO:10
RRLVTPPVAIFCLPGTAMGPNASSSGPQHPASLSGTWTVYPNGRFGNQMGQYATLLAL
AQLNGRRAFILPAMHAALAPVFRITLPVLAPEVDSRTPWRELQLHDWMSEEYADLRDP
FLKLSGFPCSWTFFHHLREQIRREFTLHDHLREEAQSVLGQLRLGRTGDRPRTFVGVH
VRRGDYLQVMPQRWKGVVGDSAYLRQAMDWFRARHEAPVFVVISNGMEWCKENIDTSQ
GDVTFAGDGQEATPWKDFALLTQCNHTIMTIGTFGFWAAYLAGGDTVYLANFTLPDSE
FLKIFKPEAAFLPEWVGINADLSPLWTLAKP

```
  1 atggccgagg tgttgcggac gctggccgga aaaccaaaat gccacgcact cgacctatg   SEQ. ID NO:11
 61 atccttttcc taataatgct tgtcttggtc ttgtttggtt acgggtcct aagcccaga
121 agtctaatgc caggaagcct ggaacggggg ttctgcatgg ctgttaggga acctgaccat
181 ctgcagcgcg tctcgttgcc aaggatggtc taccccagc caaaggtgct gacaccgtgg
241 aaggatgtcc tcgtggtgac cccttggctg ctcccattg tctgggaggg cacattcaac
301 atcgacatcc tcaacgagca gttcaggctc cagaacacca ccattgggtt aactgtgttt
361 gccatcaaga aatacgtggc tttcctgaag ctgttcctgg agacggcgga gaagcacttc
```

-continued

```
 421 atggtgggcc accgtgtcca ctactatgtc ttcaccgacc agctggccgc ggtgccccgc
 481 gtgacgctgg ggaccggtcg gcagctgtca gtgctggagg tgcgcgccta caagcgctgg
 541 caggacgtgt ccatgcgccg catggagatg atcagtgact tctgcgagcg cgcttcctc
 601 agcgaggtgg attacctggt gtgcgtggac gtggacatgg agttccgcga ccacgtgggc
 661 gtggagatcc tgactccgct gttcggcacc ctgcaccccg gcttctacgg aagcagccgg
 721 gaggccttca cctacgagcg ccggcccag tcccaggcct acatcccaa ggacgagggc
 781 gatttctact acctgggggg gttcttcggg gggtcggtgc aagaggtgca gcggctcacc
 841 agggcctgcc accaggccat gatggtcgac caggccaacg gcatcgaggc cgtgtggcac
 901 gacgagagcc acctgaacaa gtacctgctg cgccacaaac ccaccaaggt gctctccccc
 961 gagtacttgt gggaccagca gctgctgggc tggcccgccg tcctgaggaa gctgaggttc
1021 actgcggtgc caagaacca ccaggcggtc cggaacccgt ga
```

MAEVLRTLAGKPKCHALRPMILFLIMLVLVLFGYGVLSPRSLMP         SEQ. ID NO:12
GSLERGFCMAVREPDHLQRVSLPRMVYPQPKVLTPWKDVLVVTPWLAPIVWEGTFNID
ILNEQFRLQNTTIGLTVFAIKKYVAFLKLFLETAEKHFMVGHRVHYYVFTDQLAAVPR
VTLGTGRQLSVLEVRAYKRWQDVSMRRMEMISDFCERRFLSEVDYLVGVDVDMEFRDH
VGVEILTPLFGTLHPGFYGSSREAFTYERRPQSQAYIPKDEGDFYYLGGFFGGSVQEV
QRLTRACHQAMMVDQANGIEAVWHDESHLNKYLLRHKPTKVLSPEYLWDQQLLGWPAV
LRKLRFTAVPKNHQAVRNP

```
atggccgagg tgttgcggac gctggccgga aaaccaaaat gccacgcact tcgacctatg    SEQ. ID NO:13
atccttttcc taataatgct tgtcttggtc ttgtttggtt acggggtcct aagcccaga
agtctaatgc caggaagcct ggaacggggg ttctgcatgc ctgttaggga acctgaccat
ctgcagcgcg tctcgttgcc aaggatggtc tacccccagc caaaggtgct gacaccgtgt
aggaaggatg tcctcgtggt gacccttgg ctggctccca ttgtctggga gggcacgttc
aacatcgaca tcctcaacga gcagttcagg ctccagaaca ccaccattgg gttaactgtg
tttgccatca agaaatacgt ggcttttctg aagctgttcc tggagacggc ggagaagcac
ttcatggtgg ccaccgtgt ccactactat gtcttcaccg accagccggc cgcggtgccc
cgcgtgacgc tggggaccgg tcggcagctg tcagtgctgg aggtgggcgc ctacaagcgc
tggcaggacg tgtccatgcg ccgcatggag atgatcagtg acttctgcga gcgcgcttc
ctcagcgagg tggattacct ggtgtgcgtg gacgtggaca tggagttccg cgaccatgtg
ggcgtggaga tcctgactcc gctgttcggc accctgcacc ccagcttcta cggaagcagc
cgggaggcct tcacctacga gcgccggccc cagtcccagg cctacatccc caaggacgag
ggcgatttct actacatggg ggcgttcttc gggggtcgg tgcaagaggt gcagcggctc
accagggcct gccaccaggc catgatggtc gaccaggcca acggcatcga ggccgtgtgg
cacgacgaga gccacctgaa caagtaccta ctgcgccaca aacccaccaa ggtgctctcc
cccgagtact gtgggacca gcagctgctg ggctggcccg ccgtcctgag gaagctgagg
ttcactgcgg tgcccaagaa ccaccaggcg gtccggaacc cgtga
```

MAEVLRTLAGKPKCHALRPMILFLIMLVLVLFGYGVLSPRSLMP         SEQ. ID NO:14
GSLERGFCMAVREPDHLQRVSLPRMVYPQPKVLTPCRKDVLVVTPWLAPIVWEGTFNI
DILNEQFRLQNTTIGLTVFAIKKYVAFLKLFLETAEKHFMVGHRVHYYVFTDQPAAVP
RVTLGTGRQLSVLEVGAYKRWQDVSMRRMEMJSDFCERRFLSEVDYLVCVDVDMEFRD

HVGVEILTPLFGTLHPSFYGSSREAFTYERRPQSQAYIPKDEGDFYYMGAFFGGSVQE

VQRLTRACHQAMMVDQANGIEAVWHDESHLNKYLLRHKPTKVLSPEYLWDQQLLGWPA

VLRKLRFTAVPKNHQAVRNP

---

What is claimed as the invention is:

1. A transgenic pig whose genome comprises a homozygous inactivation of the α1,3GT gene, and wherein said genome further comprises a DNA sequence encoding α1,2FT, operably linked to a promoter and expressed wherein cells, tissue, or organs of said pig exhibit reduced hyperacute rejection.

2. The pig of claim 1, wherein at least part of the DNA sequence of the α1,3GT gene are replaced with the DNA sequence encoding α1,2FT.

3. The pig of claim 1, wherein the DNA sequence encoding α1,2FT is placed under the control of an endogenous α1,3GT gene promoter.

4. The pig of claim 1, wherein the genome further comprises a DNA sequence encoding a blood group A- or B-transferase.

5. An isolated porcine cell whose genome comprises a homozygous inactivation of the α1,3GT gene, and wherein said genome further comprises a DNA sequence encoding α1,2FT, operably linked to a promoter and expressed wherein said cell exhibits reduced hyperacute rejection.

6. The cell of claim 5, wherein at least part of the DNA sequence of the α1,3GT gene is replaced with the DNA sequence encoding α1,2FT.

7. The cell of claim 6, wherein the DNA sequence encoding α1,2FT is placed under the control of an endogenous α1,3GT gene promoter.

8. The cell of claim 6, wherein the genome further comprises a DNA sequence encoding a blood group A- or B-transferase.

9. Isolated porcine tissue comprising a porcine cell whose genome comprises a homozygous inactivation of the α1,3GT gene, and wherein said genome further comprises a DNA sequence encoding α1,2FT, operably linked to a promoter and expressed wherein said tissue exhibits reduced hyperacute rejection.

10. The tissue of claim 9, wherein at least part of the DNA sequence of the α1,3GT gene is replaced with the DNA sequence encoding α1,2FT.

11. The tissue of claim 9, wherein the DNA sequence encoding α1,2FT is placed under the control of an endogenous α1,3GT gene promoter.

12. The tissue of claim 9, wherein the genome further comprises a DNA sequence encoding a blood group A- or B-transferase.

13. The tissue of claim 9, wherein the tissue is lung tissue, kidney tissue, liver tissue, cardiac tissue, pancreatic tissue, or ocular tissue.

14. A method for making the tissue of claim 9 comprising:
  a) obtaining a porcine fibroblast cell whose genome comprises a homozygous inactivation of the α1,3GT gene, and wherein said genome further comprises a DNA sequence encoding α1,2FT operably linked to a promoter;
  b) transferring the nucleus of the cell to an enucleated porcine oocyte to produce an embryo;
  c) engrafting the embryo into the uterus of a host pig;
  d) obtaining a cloned pig from the engrafted embryo; and
  e) harvesting the tissue from the cloned pig or its progeny.

15. A method for making the tissue of claim 9 comprising:
  a) obtaining a telomerized porcine cell whose genome comprises a homozygous inactivation of the α1,3GT gene, and wherein said genome further comprises a DNA sequence encoding α1,2FT operably linked to a promoter;
  b) transferring the nucleus of the cell to an enucleated porcine oocyte to produce an embryo;
  c) engrafting the embryo into the uterus of a host pig;
  d) obtaining a cloned pig from the engrafted embryo; and
  e) harvesting the tissue from the cloned pig or its progeny.

* * * * *